(12) United States Patent
Movassaghi et al.

(10) Patent No.: US 10,918,627 B2
(45) Date of Patent: Feb. 16, 2021

(54) CONVERGENT AND ENANTIOSELECTIVE TOTAL SYNTHESIS OF COMMUNESIN ANALOGS

(71) Applicant: Massachusetts Institute of Technology, Cambridge, MA (US)

(72) Inventors: Mohammad Movassaghi, Lincoln, MA (US); Stephen Paul Lathrop, San Mateo, CA (US); Matthew W. Pompeo, Cambridge, MA (US); Wen-Tau Timothy Chang, Billerica, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/592,090

(22) Filed: May 10, 2017

(65) Prior Publication Data

US 2017/0333405 A1    Nov. 23, 2017

Related U.S. Application Data

(60) Provisional application No. 62/334,826, filed on May 11, 2016.

(51) Int. Cl.
| | | |
|---|---|---|
| *C07D 487/22* | (2006.01) | |
| *A61K 31/437* | (2006.01) | |
| *A61K 31/407* | (2006.01) | |
| *A61K 31/55* | (2006.01) | |
| *A61K 45/06* | (2006.01) | |

(52) U.S. Cl.
CPC .......... *A61K 31/437* (2013.01); *A61K 31/407* (2013.01); *A61K 31/55* (2013.01); *A61K 45/06* (2013.01); *C07D 487/22* (2013.01); *Y02A 50/30* (2018.01)

(58) Field of Classification Search
CPC .................................................. C07D 487/22
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 4,906,562 A | 3/1990 | Hellström et al. | |
| 4,935,495 A | 6/1990 | Hellström et al. | |
| 4,940,726 A | 7/1990 | Pettit et al. | |
| 4,946,778 A | 8/1990 | Ladner et al. | |
| 4,996,237 A | 2/1991 | Pettit et al. | |
| 5,225,539 A | 7/1993 | Winter et al. | |
| 5,242,824 A | 9/1993 | Hellström et al. | |
| 5,338,845 A | 8/1994 | Barrow et al. | |
| 5,409,953 A | 4/1995 | Pettit et al. | |
| 5,423,753 A | 6/1995 | Fowles et al. | |
| 5,430,062 A | 7/1995 | Cushman et al. | |
| 5,475,092 A | 12/1995 | Chari et al. | |
| 5,504,074 A | 4/1996 | D'Amato et al. | |
| 5,525,632 A | 6/1996 | Obsumi et al. | |
| 5,545,806 A | 8/1996 | Lonberg et al. | |
| 5,561,122 A | 10/1996 | Pettit | |
| 5,569,786 A | 10/1996 | Pettit et al. | |
| 5,569,825 A | 10/1996 | Lonberg et al. | |
| 5,585,089 A | 12/1996 | Queen | |
| 5,625,126 A | 4/1997 | Lonberg et al. | |
| 5,633,425 A | 5/1997 | Lonberg et al. | |
| 5,646,176 A | 7/1997 | Golik et al. | |
| 5,661,016 A | 8/1997 | Lonberg et al. | |
| 5,661,143 A | 8/1997 | D'Amato et al. | |
| 5,674,906 A | 10/1997 | Hatanaka et al. | |
| 5,731,353 A | 3/1998 | Ohsumi et al. | |

(Continued)

FOREIGN PATENT DOCUMENTS

| | | |
|---|---|---|
| CN | 105198885 A | 12/2015 |
| EP | 0105360 A | 4/1984 |

(Continued)

OTHER PUBLICATIONS

Crawley. Organic Letters, 2003, 5(18), 3169-71 (Year: 2003).*
Kerzaon. Rapid Communications in Mass Spectroscopy, 2009, 23, 3928-38 (Year: 2009).*
Adams, T. C. et al., "Concise Total Synthesis of (+)-Luteoalbusins A and B," *Org. Lett.* 2015, 17, pp. 4268-4271.
Andersen, B. et al., "*Penicillium* expansum: Consistent Production of Patulin, Chaetoglobosins, and Other Secondary Metabolites in Culture and Their Natural Occurrence in Fruit Products," *J. Agric. Food Chem.* 2004, 52, pp. 2421-2428.

(Continued)

*Primary Examiner* — Noble E Jarrell
(74) *Attorney, Agent, or Firm* — Wolf, Greenfield & Sacks, P.C.

(57) ABSTRACT

A highly convergent biomimetic synthesis of a complex polycyclic scaffold has been successfully implemented. From these efforts, compounds having a structure of Formula (I):

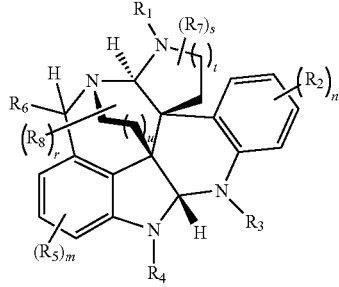

Formula (I)

or a pharmaceutically acceptable salt, tautomer or stereoisomer thereof, wherein $R^1$-$R^8$ and m, n, r, s, t, and u are as defined herein, is provided. Methods of making such compounds are also disclosed as are methods for the treatment of cancer, various infectious diseases, and abnormal cardiovascular function.

24 Claims, 5 Drawing Sheets

(56) References Cited

U.S. PATENT DOCUMENTS

| | | | |
|---|---|---|---|
| 5,821,337 | A | 10/1998 | Carter et al. |
| 5,877,158 | A | 3/1999 | Bosslet et al. |
| 5,886,025 | A | 3/1999 | Pinney |
| 5,892,069 | A | 4/1999 | D'Amato et al. |
| 5,929,211 | A | 7/1999 | Ashkenazi et al. |
| 5,985,837 | A | 11/1999 | Ritter et al. |
| 6,054,297 | A | 4/2000 | Carter et al. |
| 6,103,236 | A | 8/2000 | Suzawa et al. |
| 6,147,076 | A | 11/2000 | Danishefsky et al. |
| 6,150,407 | A | 11/2000 | Tusé et al. |
| 6,162,810 | A | 12/2000 | Carson et al. |
| 6,162,930 | A | 12/2000 | Pinney et al. |
| 6,169,104 | B1 | 1/2001 | Tusé et al. |
| 6,201,001 | B1 | 3/2001 | Wang et al. |
| 6,214,345 | B1 | 4/2001 | Firestone et al. |
| 6,232,327 | B1 | 5/2001 | Nickel et al. |
| 6,262,094 | B1 | 7/2001 | Hoefle et al. |
| 6,268,488 | B1 | 7/2001 | Barbas, III et al. |
| 6,271,220 | B1 | 8/2001 | Garst |
| 6,329,420 | B1 | 12/2001 | Uckun et al. |
| 6,335,364 | B1 | 1/2002 | Uckun et al. |
| 6,350,777 | B2 | 2/2002 | Pinney et al. |
| 6,358,957 | B1 | 3/2002 | Fukumoto et al. |
| 6,407,213 | B1 | 6/2002 | Carter et al. |
| 6,423,753 | B1 | 7/2002 | Dougherty |
| 6,433,012 | B1 | 8/2002 | Tusé et al. |
| 6,528,676 | B1 | 3/2003 | D'Amato et al. |
| 6,582,928 | B1 | 6/2003 | Ashkenazi et al. |
| 6,620,976 | B2 | 9/2003 | Sakanoue et al. |
| 6,639,055 | B1 | 10/2003 | Carter et al. |
| 6,677,435 | B2 | 1/2004 | Barbas, III et al. |
| 6,759,509 | B1 | 7/2004 | King et al. |
| 6,815,530 | B2 | 11/2004 | Ekwuribe et al. |
| 6,835,802 | B2 | 12/2004 | Ekwuribe et al. |
| 6,855,689 | B2 | 2/2005 | Firestone et al. |
| 6,858,580 | B2 | 2/2005 | Ekwuribe et al. |
| 6,870,033 | B1 | 3/2005 | Hsei et al. |
| 6,897,034 | B2 | 5/2005 | Bebbington et al. |
| 7,018,809 | B1 | 3/2006 | Carter |
| 7,030,082 | B2 | 4/2006 | Soltero et al. |
| 7,087,840 | B2 | 8/2006 | Herring et al. |
| 7,091,186 | B2 | 8/2006 | Senter et al. |
| 7,115,573 | B2 | 10/2006 | Pickford et al. |
| 7,119,162 | B2 | 10/2006 | Ekwuribe et al. |
| 7,122,636 | B1 | 10/2006 | Hsei et al. |
| 7,183,076 | B2 | 2/2007 | Arathoon et al. |
| 7,214,663 | B2 | 5/2007 | Bebbington et al. |
| 7,214,776 | B2 | 5/2007 | Hsei et al. |
| 7,223,837 | B2 | 5/2007 | de Groot et al. |
| 7,256,257 | B2 | 8/2007 | Doronina et al. |
| 7,304,032 | B2 | 12/2007 | Bebbington et al. |
| 7,319,139 | B2 | 1/2008 | Brasalawsky et al. |
| 7,375,078 | B2 | 5/2008 | Feng |
| 7,427,399 | B2 | 9/2008 | Jakobovits et al. |
| 7,479,544 | B2 | 1/2009 | Clark et al. |
| 7,494,646 | B2 | 2/2009 | Jakobovits et al. |
| 7,507,405 | B2 | 3/2009 | Hsei et al. |
| 7,521,541 | B2 | 4/2009 | Eigenbrot et al. |
| 7,541,442 | B2 | 6/2009 | Gudas et al. |
| 7,547,768 | B2 | 6/2009 | Dowd et al. |
| 7,553,816 | B2 | 6/2009 | Senter et al. |
| 7,585,834 | B2 | 9/2009 | Wender et al. |
| 7,595,379 | B2 | 9/2009 | Gudas et al. |
| 7,659,241 | B2 | 2/2010 | Senter et al. |
| 7,662,936 | B2 | 2/2010 | Kadkhodayan et al. |
| 7,691,962 | B2 | 4/2010 | Boyd et al. |
| 7,696,313 | B2 | 4/2010 | Pickford et al. |
| 7,705,045 | B2 | 4/2010 | de Groot et al. |
| 7,714,016 | B2 | 5/2010 | Gangwar et al. |
| 7,723,485 | B2 | 5/2010 | Junutula et al. |
| 7,745,394 | B2 | 6/2010 | Doronina et al. |
| 7,749,504 | B2 | 7/2010 | Cairns et al. |
| 7,750,116 | B1 | 7/2010 | Doronina et al. |
| 7,754,441 | B2 | 7/2010 | de Sauvage et al. |
| 7,754,681 | B2 | 7/2010 | Feng |
| 7,803,915 | B2 | 9/2010 | Cairns et al. |
| 7,811,565 | B2 | 10/2010 | Jakobovits et al. |
| 7,816,317 | B2 | 10/2010 | Bebbington et al. |
| 7,829,531 | B2 | 11/2010 | Senter et al. |
| 7,834,154 | B2 | 11/2010 | Koch et al. |
| 7,842,789 | B2 | 11/2010 | Hsei et al. |
| 7,846,893 | B2 | 12/2010 | Sinko et al. |
| 7,851,437 | B2 | 12/2010 | Senter et al. |
| 7,855,275 | B2 | 12/2010 | Eigenbrot et al. |
| 7,858,759 | B2 | 12/2010 | Brandt et al. |
| 7,888,536 | B2 | 2/2011 | Davis et al. |
| 7,893,023 | B2 | 2/2011 | Trouet et al. |
| 7,964,566 | B2 | 6/2011 | Doronina et al. |
| 7,964,567 | B2 | 6/2011 | Doronina et al. |
| 7,968,090 | B2 | 6/2011 | Raitano et al. |
| 7,989,434 | B2 | 8/2011 | Feng |
| 7,989,595 | B2 | 8/2011 | Dennis et al. |
| 8,012,978 | B2 | 9/2011 | Zhao et al. |
| 8,158,590 | B2 | 4/2012 | Beusker et al. |
| 8,337,856 | B2 | 12/2012 | Blättler et al. |
| 9,353,150 | B2 | 5/2016 | Movassaghi et al. |
| 9,434,736 | B2 | 9/2016 | Movassaghi et al. |
| 9,464,093 | B2 | 10/2016 | Tun et al. |
| 9,962,383 | B2 | 5/2018 | Movassaghi et al. |
| 10,220,099 | B2 | 3/2019 | Movassaghi et al. |
| 2003/0096743 | A1 | 5/2003 | Senter et al. |
| 2003/0130189 | A1 | 7/2003 | Senter et al. |
| 2003/0149003 | A1 | 8/2003 | Chaplin et al. |
| 2005/0143429 | A1 | 6/2005 | Danishefsky et al. |
| 2008/0050310 | A1 | 2/2008 | Ebens et al. |
| 2008/0267981 | A1 | 10/2008 | Janda et al. |
| 2009/0068202 | A1 | 3/2009 | Chen et al. |
| 2009/0203584 | A1 | 8/2009 | Cuthbertson et al. |
| 2009/0280056 | A1 | 11/2009 | Dennis et al. |
| 2010/0125065 | A1 | 5/2010 | Moon et al. |
| 2010/0210543 | A1 | 8/2010 | Rabuka et al. |
| 2010/0215669 | A1 | 8/2010 | Chen et al. |
| 2011/0118480 | A1 | 5/2011 | Vijayaraghavan et al. |
| 2011/0124844 | A1 | 5/2011 | Davis et al. |
| 2011/0135667 | A1 | 6/2011 | Chen et al. |
| 2011/0137017 | A1 | 6/2011 | Eigenbrot et al. |
| 2011/0142859 | A1 | 6/2011 | Ebens, Jr. et al. |
| 2011/0195021 | A1 | 8/2011 | Deckert et al. |
| 2011/0195022 | A1 | 8/2011 | Deckert et al. |
| 2011/0269972 | A1 | 11/2011 | Loh et al. |
| 2012/0183566 | A1 | 7/2012 | Barfield et al. |
| 2014/0187500 | A1 | 7/2014 | Movassaghi et al. |
| 2015/0080405 | A1 | 3/2015 | Movassaghi et al. |
| 2015/0274742 | A1 | 10/2015 | Tun et al. |
| 2016/0354483 | A1 | 12/2016 | Movassaghi et al. |
| 2017/0143708 | A1 | 5/2017 | Movassaghi et al. |
| 2017/0342077 | A1 | 11/2017 | Movassaghi et al. |
| 2018/0360830 | A1 | 12/2018 | Movassaghi et al. |
| 2019/0119286 | A1 | 4/2019 | Movassaghi et al. |
| 2019/0255187 | A1 | 8/2019 | Movassaghi et al. |

FOREIGN PATENT DOCUMENTS

| | | |
|---|---|---|
| EP | 0171496 A2 | 2/1986 |
| EP | 0173494 A2 | 3/1986 |
| EP | 0184187 A2 | 6/1986 |
| EP | 0217577 B1 | 4/1987 |
| EP | 0375562 A | 6/1990 |
| WO | WO 1983/03679 A1 | 10/1983 |
| WO | WO 1986/01533 A1 | 3/1986 |
| WO | WO 1987/02671 A1 | 5/1987 |
| WO | WO 1988/03145 A2 | 5/1988 |
| WO | WO 1991/00295 A1 | 1/1991 |
| WO | WO 1992/016486 A1 | 10/1992 |
| WO | WO 1993/08829 A1 | 5/1993 |
| WO | WO 1994/04690 A1 | 3/1994 |
| WO | WO 1994/14787 A1 | 7/1994 |
| WO | WO 1995/04535 A1 | 2/1995 |
| WO | WO 1997/34631 A1 | 9/1997 |
| WO | WO 1998/039323 A1 | 9/1998 |
| WO | WO 1999/02166 A1 | 1/1999 |
| WO | WO 1999/02514 A2 | 1/1999 |
| WO | WO 1999/034788 A1 | 7/1999 |
| WO | WO 1999/035150 A1 | 7/1999 |

(56) References Cited

FOREIGN PATENT DOCUMENTS

| | | |
|---|---|---|
| WO | WO 1999/35164 A1 | 7/1999 |
| WO | WO 1999/048495 A1 | 9/1999 |
| WO | WO 1999/051224 A1 | 10/1999 |
| WO | WO 1999/051246 A1 | 10/1999 |
| WO | WO 2000/00514 A2 | 1/2000 |
| WO | WO 2000/41669 A2 | 1/2000 |
| WO | WO 2000/006556 A1 | 2/2000 |
| WO | WO 2000/26229 A1 | 5/2000 |
| WO | WO 2000/035865 A2 | 6/2000 |
| WO | WO 2000/40529 A1 | 7/2000 |
| WO | WO 2000/048590 A1 | 8/2000 |
| WO | WO 2000/048591 A1 | 8/2000 |
| WO | WO 2000/073264 A1 | 12/2000 |
| WO | WO 2001/009103 A2 | 2/2001 |
| WO | WO 2001/012579 A2 | 2/2001 |
| WO | WO 2001/019794 A2 | 3/2001 |
| WO | WO 2001/022954 A2 | 4/2001 |
| WO | WO 2001/024763 A2 | 4/2001 |
| WO | WO 2001/30803 A1 | 5/2001 |
| WO | WO 2001/40268 A2 | 6/2001 |
| WO | WO 2001/40309 A2 | 6/2001 |
| WO | WO 2001/068654 A2 | 9/2001 |
| WO | WO 2001/081288 A1 | 11/2001 |
| WO | WO 2001/081355 A1 | 11/2001 |
| WO | WO 2001/082909 A2 | 11/2001 |
| WO | WO 2001/084929 A1 | 11/2001 |
| WO | WO 2001/092224 A2 | 12/2001 |
| WO | WO 2002/04434 A1 | 1/2002 |
| WO | WO 2002/06267 A2 | 1/2002 |
| WO | WO 2002/08213 A1 | 1/2002 |
| WO | WO 2002/012228 A1 | 2/2002 |
| WO | WO 2002/014329 A1 | 2/2002 |
| WO | WO 2002/016429 A2 | 2/2002 |
| WO | WO 2002/16581 A2 | 2/2002 |
| WO | WO 2002/022576 A2 | 3/2002 |
| WO | WO 2002/022626 A1 | 3/2002 |
| WO | WO 2002/42319 A2 | 5/2002 |
| WO | WO 2002/043661 A2 | 6/2002 |
| WO | WO 2002/47604 A2 | 6/2002 |
| WO | WO 2002/050007 A2 | 6/2002 |
| WO | WO 2002/060872 A1 | 8/2002 |
| WO | WO 2002/088172 A2 | 11/2002 |
| WO | WO 2002/098883 A1 | 12/2002 |
| WO | WO 2003/000113 A2 | 1/2003 |
| WO | WO 2003/024392 A2 | 3/2003 |
| WO | WO 2003/026577 A2 | 4/2003 |
| WO | WO 2003/043583 A2 | 5/2003 |
| WO | WO 2003/068144 A2 | 8/2003 |
| WO | WO 2003/106621 A2 | 12/2003 |
| WO | WO 2004/005470 A2 | 1/2004 |
| WO | WO 2004/010957 A2 | 2/2004 |
| WO | WO 2004/013093 A2 | 2/2004 |
| WO | WO 2004/016225 A2 | 2/2004 |
| WO | WO 2004/016801 A2 | 2/2004 |
| WO | WO 2004/032828 A2 | 4/2004 |
| WO | WO 2004/043344 A2 | 5/2004 |
| WO | WO 2004/043493 A1 | 5/2004 |
| WO | WO 2004/045516 A2 | 6/2004 |
| WO | WO 2004/050867 A1 | 6/2004 |
| WO | WO 2004/090113 A2 | 10/2004 |
| WO | WO 2004/106343 A2 | 12/2004 |
| WO | WO 2004/110498 A2 | 12/2004 |
| WO | WO 2005/001038 A2 | 1/2005 |
| WO | WO 2005/009369 A2 | 2/2005 |
| WO | WO 2005/037992 A2 | 4/2005 |
| WO | WO 2005/070026 A2 | 8/2005 |
| WO | WO 2005/077090 A2 | 8/2005 |
| WO | WO 2005/081711 A2 | 9/2005 |
| WO | WO 2005/082023 A2 | 9/2005 |
| WO | WO 2005/084390 A2 | 9/2005 |
| WO | WO 2006/044643 A2 | 4/2006 |
| WO | WO 2006/055578 A2 | 5/2006 |
| WO | WO 2006/065533 A2 | 6/2006 |
| WO | WO 2006/086733 A2 | 8/2006 |
| WO | WO 2006/113909 A2 | 10/2006 |
| WO | WO 2006/128103 A2 | 11/2006 |
| WO | WO 2006/132670 A2 | 12/2006 |
| WO | WO 2007/008603 A1 | 1/2007 |
| WO | WO 2007/008848 A2 | 1/2007 |
| WO | WO 2007/011968 A2 | 1/2007 |
| WO | WO 2007/019232 A2 | 2/2007 |
| WO | WO 2007/024222 A1 | 3/2007 |
| WO | WO 2007/024536 A2 | 3/2007 |
| WO | WO 2007/030642 A2 | 3/2007 |
| WO | WO 2007/062138 A2 | 5/2007 |
| WO | WO 2007/075326 A2 | 7/2007 |
| WO | WO 2007/089149 A2 | 8/2007 |
| WO | WO 2007/103288 A2 | 9/2007 |
| WO | WO 2007/137170 A2 | 11/2007 |
| WO | WO 2008/025020 A2 | 2/2008 |
| WO | WO 2008/070593 A2 | 6/2008 |
| WO | WO 2008/078109 A2 | 7/2008 |
| WO | WO 2009/017394 A2 | 2/2009 |
| WO | WO 2009/048967 A1 | 4/2009 |
| WO | WO 2009/052431 A2 | 4/2009 |
| WO | WO 2009/080830 A1 | 7/2009 |
| WO | WO 2009/080831 A1 | 7/2009 |
| WO | WO 2009/080832 A1 | 7/2009 |
| WO | WO 2009/117531 A1 | 9/2009 |
| WO | WO 2009/134870 A1 | 11/2009 |
| WO | WO 2009/134952 A2 | 11/2009 |
| WO | WO 2009/134976 A1 | 11/2009 |
| WO | WO 2009/134977 A1 | 11/2009 |
| WO | WO 2009/135181 A2 | 11/2009 |
| WO | WO 2010/008726 A1 | 1/2010 |
| WO | WO 2010/025272 A1 | 3/2010 |
| WO | WO 2010/128087 A2 | 5/2010 |
| WO | WO 2010/062171 A2 | 6/2010 |
| WO | WO 2010/081004 A1 | 7/2010 |
| WO | WO 2010/111018 A1 | 9/2010 |
| WO | WO 2011/038159 A2 | 9/2010 |
| WO | WO 2010/126551 A1 | 11/2010 |
| WO | WO 2010/126552 A1 | 11/2010 |
| WO | WO 2010/141566 A1 | 12/2010 |
| WO | WO 2011/100403 A1 | 2/2011 |
| WO | WO 2011/106528 A1 | 2/2011 |
| WO | WO 2011/112978 A1 | 3/2011 |
| WO | WO 2011/050180 A1 | 4/2011 |
| WO | WO 2011/130613 A1 | 4/2011 |
| WO | WO 2011/091286 A1 | 7/2011 |
| WO | WO 2011/100398 A1 | 8/2011 |
| WO | WO 2011/133039 A2 | 10/2011 |
| WO | WO 2011/162933 A1 | 12/2011 |
| WO | WO 2012/019024 A2 | 2/2012 |
| WO | WO 2012/047724 A1 | 4/2012 |
| WO | WO 2012/054748 A2 | 4/2012 |
| WO | WO 2012/149412 A2 | 4/2012 |
| WO | WO 2012/058592 A2 | 5/2012 |
| WO | WO 2012/061590 A1 | 5/2012 |
| WO | WO 2012/078688 A2 | 6/2012 |
| WO | WO 2012/112687 A1 | 8/2012 |
| WO | WO 2012/112708 A1 | 8/2012 |
| WO | WO 2012/128868 A2 | 9/2012 |
| WO | WO 2012/135517 A2 | 10/2012 |
| WO | WO 2012/135522 A2 | 10/2012 |
| WO | WO 2012/135675 A2 | 10/2012 |
| WO | WO 2012/135740 A2 | 10/2012 |
| WO | WO 2012/138537 A2 | 10/2012 |
| WO | WO 2012/138749 A2 | 10/2012 |
| WO | WO 2012/145112 A2 | 10/2012 |
| WO | WO 2012/177837 A2 | 12/2012 |
| WO | WO 2013/049410 A1 | 4/2013 |
| WO | WO 2013/055990 A1 | 4/2013 |
| WO | WO 2013/055993 A1 | 4/2013 |
| WO | WO 2014/059314 A1 | 4/2014 |

OTHER PUBLICATIONS

Behenna, D. C. et al., "Confirmation of the absolute configuration of (−)-aurantioclavine," *Tetrahedron Lett.* 2011, 52, pp. 2152-2154.

Belmar, J. et al., "Total Synthesis of (±)-Communesin F via a Cycloaddition with Indol-2-one," *J. Am. Chem. Soc.* 2012, 134, pp. 16941-16943.

(56) References Cited

OTHER PUBLICATIONS

Belmar, J., "Total Synthesis of (±)-Isophellibiline and (±)-Communesin F, and Design, Synthesis and Pharmacological Evaluation of Dihydro-β-Erythroidine (DHβE) Analogs," Dec. 2012, pp. 1-179.

Benkovics, T. et al., "Oxaziridine-Mediated Oxyamination of Indoles: An Approach to 3-Aminoindoles and Enantiomerically Enriched 3-Aminopyrrolo-indolines," *Angew. Chem. Int. Ed.* 2010, 49, pp. 9153-9157.

Boyer, N. et al., "Concise total synthesis of (+)-gliocladins B and C," *Chem. Sci.* 2012, 3, pp. 1798-1803.

Brak, K. et al., "Total Synthesis of (−)-Aurantioclavine," *Org. Lett.* 2010, 12, pp. 2004-2007.

Cogan, D. A. et al., "Asymmetric Synthesis of Chiral Amines by Highly Diastereoselective 1,2-Additions of Organometallic Reagents to N-tert-Butanesulfinyl Imines," *Tetrahedron* 1999, 55, pp. 8883-8904.

Cordell, G. A. et al., "Bisindole Alkaloids," *The Alkaloids: Chemistry and Pharmacology*, Manske, R. H. F; Rodrigo, R. G., Eds., Academic Press: New York 1981, vol. 20, pp. 3-295.

Corey, E. J. et al., "Enantioselective Total Synthesis of Ecteinascidin 743," *J. Am. Chem. Soc.* 1996, 118, pp. 9202-9203.

Crich, D. et al., "Chemistry of the Hexahydropyrrolo[2,3-b]indoles: Configuration, Conformation, Reactivity, and Applications in Synthesis," *Acc. Chem. Res.* 2007, 40, pp. 151-161.

Dalsgaard, P. W. et al., "Communesins G and H, New Alkaloids from the Psychrotolerant Fungus *Penicillium rivulum*," *J. Nat. Prod.* 2005, 68, pp. 258-261.

Davis, F. A. et al., "Adventures in Sulfur-Nitrogen Chemistry," *J. Org. Chem.* 2006, 71, pp. 8993-9003.

Davis, F. A. et al., "Asymmetric synthesis of amino acids using sulfinimines (thiooxime S-oxides)," *Chem. Soc. Rev.* 1998, 27, pp. 13-18.

DePorter, S. M. et al., "N-Nosyl oxaziridines as terminal oxidants in copper(II)-catalyzed olefin oxyaminations," *Tetrahedron* 2010, 51, pp. 5223-5225.

Fan, Y.-Q. et al., "Alkaloids with Cardiovascular Effects from the Marine-Derived Fungus *Penicillium expansum* Y32," *Mar. Drugs* 2015, 13, pp. 6489-6504.

Fuchs, J. R. et al., "Total Synthesis of (±)-Perophoramidine," *J. Am. Chem. Soc.* 2004, 126, pp. 5068-5069.

Guéritte-Voegelein, F. et al., "Alkaloids From *Psychotria Oleoides* with Activity on Growth Hormone Release," *J. Nat. Prod.* 1992, 55, pp. 923-930.

Han, S.-J. et al., "A Diastereodivergent Synthetic Strategy for the Syntheses of Communesin F and Perophoramidine," *Org. Lett.* 2014, 16, pp. 3316-3319.

Hayashi, H. et al., "New Insecticidal Compounds, Communesins C, D and E, from Penicillium expansum Link MK-57," *Biosci. Biotechnol. Biochem.* 2004, 68, pp. 753-756.

Hegedus, L. S. et al., "Palladium-Catalyzed Reactions in the Synthesis of 3- and 4-Substituted Indoles. 3. Total Synthesis of (±)-Aurantioclavine," *J. Org. Chem.* 1987, 52, pp. 3319-3322.

Hendrickson, J. B. et al., "Total Synthesis of the Calycanthaceous Alkaloids," *Tetrahedron* 1964, 20, pp. 565-579.

Herzon, S. B. et al., "Enantioselective Synthesis of Stephacidin B," *J. Am. Chem. Soc.* 2005, 127, pp. 5342-5344.

Hino, T. et al., "Chemistry and Reactions of Cyclic Tautomers of Tryptamines and Tryptophans," *The Alkaloids: Chemistry and Pharmacology*, Brossi, A., Ed., Academic Press: New York 1988, vol. 34, pp. 1-75.

Hoffmann, S. et al., "A Powerful Bronsted Acid Catalyst for the Organocatalytic Asymmetric Transfer Hydrogenation of Imines," *Angew. Chem. Int. Ed.* 2005, 44, pp. 7424-7427.

International Search Report and Written Opinion dated Aug. 11, 2017 from International Application No. PCT/US17/320470, 12 pages.

Jadulco, R. C., "Isolation and Structure Elucidation of Bioactive Secondary Metabolites from Marine Sponges and Sponge-derived Fungi," 2002, 88 pages.

Jadulco, R. et al., "New Communesin Derivatives from the Fungus *Penicillium* sp. Derived from the Mediterranean Sponge *Axinella verrucosa*," *J. Nat. Prod.* 2004, 67, pp. 78-81.

Kim, J. et al., "Concise Total Synthesis and Stereochemical Revision of (+)-Naseseazines A and B: Regioselective Arylative Dimerization of Diketopiperazine Alkaloids," *J. Am. Chem. Soc.* 2011, 133, pp. 14940-14943.

Kitir, B. et al., "Total synthesis and structural validation of cyclodepsipeptides solonamide A and B," *Tetrahedron* 2014, 70, pp. 7721-7732.

Kozlovskii, A. G. et al., *Dokl. Akad. Nauk SSSR* 1981, 260, pp. 230-233, Machine Translation.

Krishnan, S. et al., "Pd-Catalyzed Enantioselective Aerobic Oxidation of Secondary Alcohols: Applications to the Total Synthesis of Alkaloids," *J. Am. Chem. Soc.* 2008, 130, pp. 13745-13754.

Ksander, G. et al., "Chemie der α-Aminonitrile," *Helvetica Chimica Acta* 1987, 70, pp. 1115-1172, English language Abstract.

Lathrop, S. P. et al., "Application of diazene-directed fragment assembly to the total synthesis and stereochemical assignment of (+)-desmethyl-meso-chimonanthine and related heterodimeric alkaloids," *Chem. Sci.* 2014, 5, pp. 333-340.

Lathrop, S. P. et al., "Radical-mediated Dimerization and Oxidation Reactions for the Synthesis of Complex Alkaloids," *Chimia* 2012, 66, pp. 389-393.

Lebsack, A. D. et al., "Enantioselective Total Synthesis of Quadrigemine C and Psycholeine," *J. Am. Chem. Soc.* 2002, 124, pp. 9008-9009.

Lin, H.-C. et al., "Elucidation of the Concise Biosynthetic Pathway of the Communesin Indole Alkaloids," *Angew. Chem. Int. Ed.* 2015, 54, pp. 3004-3007.

Lin, H.-C. et al., "P450-Mediated Coupling of Indole Fragments to Forge Communesin and Unnatural Isomers," *J. Am. Chem. Soc.* 2016, 138, pp. 4002-4005.

Liu, P. et al., "Total Synthesis of the Polycyclic Fungal Metabolite (±)-Communesin F," *Angew. Chem. Int. Ed.* 2010, 49, pp. 2000-2003.

Loach, R. P. et al., "Concise Total Synthesis of (+)-Asperazine, (+)-Pestalazine A, and (+)-iso-Pestalazine A. Structure Revision of (±)-Pestalazine A," *J. Am. Chem. Soc.* 2016, 138, pp. 1057-1064.

May, J. A. et al., "Biomimetic approach to communesin B (a.k.a. nomofungin)," *Tetrahedron Letters* 2003, 44, pp. 1203-1205.

May, J. A. et al., "The structural and synthetic implications of the biosynthesis of the calycanthaceous alkaloids, the communesins, and nomofungin," *Tetrahedron* 2006, 62, pp. 5262-5271.

Michaelis, D. J. et al., "Oxaziridine-mediated enantioselective aminohydroxylation of styrenes catalyzed by copper(II) bis(oxazoline) complexes," *Tetrahedron* 2009, 65, pp. 5118-5124.

Morton, D. et al., "Chiral non-racemic sulfinimines: versatile reagents for asymmetric synthesis," *Tetrahedron* 2006, 62, pp. 8869-8905.

Movassaghi, M. et al., "Concise Total Synthesis of (−)-Calycanthine, (+)-Chimonanthine, and (±)-Folicanthine," *Angew. Chem. Int. Ed.* 2007, 46, pp. 3725-3728.

Movassaghi, M. et al., "Directed Heterodimerization: Sterocontrolled Assembly via Solvent-Caged Unsymmetrical Diazene Fragmentation," *J. Am. Chem. Soc.* 2011, 133, pp. 13002-13005.

Myers, A. G. et al., "A Concise, Stereocontrolled Synthesis of (−)-Saframycin α by the Directed Condensation of α-Amino Aldehyde Precursors," *J. Am. Chem. Soc.*1999, 121, pp. 10828-10829.

Numata, A. et al., "Communesins, Cytotoxic Metabolites of a Fungus Isolated from a Marine Alga," *Tetrahedron Lett.* 1993, 34, pp. 2355-2358.

Overman, L. E. et al., "the Cyanomethyl Group for Nitrogen Protection and Iminium Ion Generation in Ring-Enlarging Pyrrolidine Annulations. A short Synthesis of the Amaryllidaceae Alkaloid d,1-Crinine," *Tetrahedron Lett.* 1982, 23, pp. 2741-2744.

Robak, M. T. et al., "Synthesis and Applications of tert-Butanesulfinamide," *Chem. Rev.* 2010, 110, pp. 3600-3740 (Parts 1 & 2).

Robinson, R. et al., "Calcycanthine and Calycanthidine," *Chem. Ind.* 1954, 27, pp. 783-784.

Roizen, J. L. et al., "Selective Intermolecular Amination of C-H Bonds at Tertiary Carbon Centers," *Angew. Chem. Int. Ed.* 2013, 52, pp. 11343-11346.

(56) References Cited

OTHER PUBLICATIONS

Schmidt. M. A. et al., "New Strategies for the Synthesis of Hexahydropyrroloindole Alkaloids Inspired by Biosynthetic Hypotheses," Synlett 2008, 3, pp. 0313-0324.
Senanayake, C. H. et al., "Enantiopure Sulfoxides and Sulfinamides: Recent Developments in Their Stereoselective Synthesis and Applications to Asymmetric Synthesis," Aldrichim. Acta 2005, 38, pp. 93-104.
Seo, J. H. et al., "Synthetic Studies on Perophoramidine and the Communesins: Construction of the Vicinal Quaternary Stereocenters," J. Org. Chem. 2006, 71, pp. 8891-8900.
Somei, M. et al., "A novel reductive amino-cyclization method and its application for the total syntheses of (±)-aurantio-clavine and (±)-lophocerine," Heterocycles 2007, 74, pp. 943-950.
Steven, A. et al., "Total Synthesis of Complex Cyclotryptamine Alkaloids: Stereocontrolled Construction of Quaternary Carbon Stereocenters," Angew. Chem. Int. Ed. 2007, 46, pp. 5488-5508.
Stork, G. S., "The sterospecific synthesis of reserpine," Pure & Appl. Chem. 1989, 61, pp. 439-442.
Suetsugu, S. et al., "Asymmetric Synthesis of (−)-Aurantioclavine via Palladium-Catalyzed Intramolecular Allylic Amination," Org. Lett. 2014, 16, pp. 996-999.
Trost, B. M. et al., "Recent Advances on the Total Syntheses of Communesin Alkaloids and Perophoramidine," Chem. Eur. J. 2015, 21, pp. 16318-16343.
Uraguchi, D. et al., "Catalytic Asymmetric Oxidation of N-Sulfonyl Imines with Hydrogen Peroxide-Trichloroacetonitrile System," J. Am. Chem. Soc. 2013, 135, pp. 8161-8164.
Verbitski, S. M. et al., "Isolation, Structure Determination, and Biological Activity of a Novel Alkaloid, Perophoramidine, from the Philippine Ascidian Perophora namei," J. Org. Chem. 2002, 67, pp. 7124-7126.
Wigley, L. J. et al., "Natural and directed biosynthesis of communesin alkaloids," Phytochemistry 2006, 67, pp. 561-569.
Williamson, K. S. et al., "Iron Catalyzed Asymmetric Oxyamination of Olefins," J. Am. Chem. Soc. 2012, 134, pp. 12370-12373.
Williamson, K. S. et al., "Iron-Catalyzed Aminohydroxylation of Olefins," J. Am. Chem. Soc. 2010, 132, pp. 4570-4571.
Woodward, R. B. et al., "Calycanthine: The Structure of the Alkaloid and its Degradation Product, Calycanine," Proc. Chem. Soc. 1960, pp. 76-78.
Xie, W. et al., "Highly Enantioselective Bromocyclization of Tryptamines and Its Application in the Synthesis of (−)-Chimonanthine," Angew. Chem. Int. Ed. 2013, 52, pp. 12924-12927.
Xu, J.-B. et al., "Studies on the Alkaloids of the Calycanthaceae and Their Syntheses," Molecules 2015, 20, pp. 6715-6738.
Xu, Z. et al., "Total Synthesis of Clavicipitic Acid and Aurantioclavine: Stereochemistry of Clavicipitic Acid Revisited," J. Org. Chem. 2010, 75, pp. 7626-7635.
Yamada, F. et al., "A Total and Practical Synthesis of Ergot Alkaloid, (±)-Aurantioclavine," Chem. Pharm. Bull. 1985, 33, pp. 2162-2163.
Yamada, K. et al., "Concise Synthesis of (±)-Aurantioclavine through a Base-Promoted Pictet-Spengler Reaction," Eur. J. Org. Chem. 2009, pp. 5752-5759.
Yang, J. et al., "Total Synthesis of (±)-Communesin F," J. Am. Chem. Soc. 2007, 129, pp. 13794-13795.
Zhou, P. et al., "Recent advances in asymmetric reactions using sulfinimines (N-sulfinyl imines)," Tetrahedron 2004, 60, pp. 8003-8030.
Zuo, Z. et al., "Enantioselective Total Syntheses of Communesins A and B," Angew. Chem. Int. Ed. 2011, 50, pp. 12008-12011.
Zuo, Z. et al., "Total Synthesis and Absolute Stereochemical Assignment of (−)-Communesin F," J. Am. Chem. Soc. 2010, 132, pp. 13226-13228.
U.S. Appl. No. 16/293,443, filed Mar. 5, 2019, Movassaghi et al.
U.S. Appl. No. 16/161,036, filed Oct. 15, 2018, Movassaghi et al.
PCT/US2017/032040, Nov. 22, 2018, International Preliminary Report on Patentability.
International Preliminary Report on Patentability for PCT/US2017/032040, dated Nov. 22, 2018

Accolla et al., "Monoclonal antibodies specific for carcinoembryonic antigen an produced by two hybrid cell lines." Proc Natl. Acad. Sci. USA 77:563-566.
Adam, W. et al., "Photochemistry of the Azoalkanes 2,3-Diazabicyclo[2.2.1]kept-2-ene and Spiro[cyclopropane-1, 7-[2,3]diazabicyclo[2.2.1]hept-2-ene]: On the Questions of One-Bond vs. Two-Bond Cleavage during the Denitrogenation, Cyclization vs. Rearrangement of the 1,3-Diradicals, and Double Inversion," J. Org. Chem. 1985, 50, pp. 3303-3312.
Adj I Bade, Y. et al., "In Vitro Cytotoxicity of Polyindolenine Alkaloids on Rat Hepatoma Cell Lines. Structure Activity Relationships," Journal of Ethnopharmacology 1990, 29, pp. 127-136.
Aleksandrzak et al., "Antimitotic activity of diaryl compounds with structural features resembling combretastatin A-4." Anticancer Drugs. Jul. 1998; 9(6):545-50.
Aliev et al., "A concise approach to the epidithiodiketopiperazine (ETP) core." Tetrahedron Lett. 2006; 47(14):2387-2390.
Amador, T. A. et al., "Antinociceptive Profile of Hodgkinsine," Planta Med 2000, 66, pp. 770-772.
Amir et al., "Self-immolative dendrimers." Angew Chem Int Ed Engl. Sep. 29, 2003; 42(37):4494-9.
Amsberry et al., "The lactonization of 2'-hydroxyhydrocinnamic acid amides: a potential prodrug for amines." J. Org. Chem. 1990; 55(23):5867-5877.
Anderson et al., "Studies on Total Synthesis of the Cytotoxic Marine Alkaloid Agelastatin A," J. Org. Chem., 63:7594-7595 (1998).
Anderson et al., Penicillium expansum: Consistent Production of Patulin, Chaetoglobosins, and Other Secondary Metabolites in Culture and Their Natural Occurrence in Fruit Products. J. Agric. Food Chem., 2004;52(8):2421-2428. DOI: 10.1021/jf035406k.
Andres et al., ""Combretatropones"—hybrids of combretastatin and colchicine. Synthesis and biochemical evaluation" Bioorganic. Med. Chem. Lett. 1993; 3(4):571-576.
Anet, E. F. L. J. et al., "Hodgkinsine, the Alkaloid of Hodgkinsonia Frutescens F. Muell," J. Chem. 1961, 14, pp. 173-174.
Anthon I, U. et al., "Naturally Occurring Cyclotryptophans and Cyclotryptamines," Alkaloids: Chemical and Biological Perspectives, Pelletier, S. W., Ed.; Pergamon: London, 1999; vol. 13, pp. 163-236.
Bacher et al., "D-24851, a novel synthetic microtubule inhibitor, exerts curative antitumoral activity in vivo, shows efficacy toward multidrug-resistant tumor cells, and lacks neurotoxicity." Cancer Res. Jan. 1, 2001; 61(1):392-9.
Bai et al., "Interaction of dolastatin 10 with tubulin: induction of aggregation and binding and dissociation reactions." Molecular Pharmacology May 1995; 47(5):965-976.
Baldwin, J. E. et al., "Azo Anions in Synthesis. Use of Trityl- and Diphenyl-4-Pyridylmenthylhydrazones for Reductive C-C Bond Formation," Tetrahedron 1986, vol. 42, No. 15, pp. 4235-4246.
Banwell et al., "Synthesis, X-Ray Crystal Structure and Tubulin-Binding Properties of a Benzofuran Analogue of the Potent Cytotoxic Agent Combretastatin A4." Australian Journal of Chemistry 1999; 52(8):767-774.
Barrow et al., "WIN 64821, a new competitive antagonist to substance P, isolated from an Aspergillus species: structure determination and solution conformation." J. Org. Chem. 1993; 58(22):6016-6021.
Baselga et al., "Phase II study of weekly intravenous recombinant humanized anti-p185HER2 monoclonal antibody in patients with HER2/neu-overexpressing metastatic breast cancer." J Clin Oncol. Mar. 1996; 14(3):737-44.
Bast et al., "Reactivity of a monoclonal antibody with human ovarian carcinoma." J Clin Invest. Nov. 1981; 68(5):1331-7.
Beck et al., "Mild Aerobic Oxidative Palladium (II) Catalyzed C—H Bond Functionalization: Regioselective and Switchable C—H Alkenylation and Annulation of Pyrroles." J. Am. Chem. Soc. 2006; 128(8):2528-2529.
Bedford et al., "Synthesis of water-soluble prodrugs of the cytotoxic agent Combretastatin A4." Bioorganic. Med. Chem. Lett. 1996; 6(2):157-160.
Beidler et al., "Cloning and high level expression of a chimeric antibody with specificity for human carcinoembryonic antigen." J Immunol Dec. 1, 1988; 141(11):4053-4060.

(56) References Cited

OTHER PUBLICATIONS

Beretz, A. et al., "Polyindolinic Alkaloids from Psychotria forsteriana. Potent Inhibitors of the Aggregation of Human Platelets," Planta Med. 1985, 51, pp. 300-303.
Bernardo et al., "A Novel Redox Mechanism for the Glutathione-dependent Reversible Uptake of a Fungal Toxin in Cells." J Biol. Chem. 2003; 278(47):46549-46555.
Bertling et al., "Candida albicans and its metabolite gliotoxin inhibit platelet function via interaction with thiols." Thromb Haemost. Aug. 2010;104(2):270-8.
Better et al., "*Escherichia coli* secretion of an active chimeric antibody fragment." Science May 20, 1988; 240(4855):1041-1043.
Bird et al., "Single-chain antigen-binding proteins." Science Apr. 28, 1989;244(4903):409.
Blokhin et al., "Characterization of the interaction of the marine cyanobacterial natural product curacin A with the colchicine site of tubulin and initial structure-activity studies with analogues." Molecular Pharmacology Sep. 1995; 48(3):523-531.
Boger et al., "Synthesis of the lower subunit of rhizoxin." J. Org. Chem.1992; 57(8):2235-2244.
Bowen et al., "Functional effects of CD30 on a large granular lymphoma cell line, YT. Inhibition of cytotoxicity, regulation of CD28 and IL-2R, and induction of homotypic aggregation." J Immunol Dec. 1, 1993; 151(11):5896-5906.
Boyer et al. Synthesis and Anticancer Activity of Epipolythiodiketopiperazine Alkaloids. Chem Sci. 2013;4(4):1646-1657. doi:10.1039/C3SC50174D.
Brak et al., Total Synthesis of (−)-Aurantioclavine. Org. Lett., 2010;12(9):2004-2007. DOI: 10.1021/o1100470g.
Brown et al., "Investigation of various N-heterocyclic substituted piperazine versions of 5/7-{ [2-(4-aryl-piperazin-1-yl)-ethyl]-propyl-amino }-5,6,7,8-tetrahydro-naphthalen-2-ol: effect on affinity and selectivity for dopamine D3 receptor." Bioorg Med Chem. Jun. 1, 2009;17(11):3923-33.
Bumol et al., "Unique glycoprotein-proteoglycan complex defined by monoclonal antibody on human melanoma cells." Proc Natl Acad Sci U S A. Feb. 1982; 79(4):1245-9.
Bundgaard, H., "(C) Means to enhance penetration: (1) Prodrugs as a means to improve the delivery of peptide drugs." Advanced Drug Delivery Revieivs. 1992; 8(1):1-38.
Canham, S. M. et al., "Stereocontrolled enantioselective total synthesis of the [2+2] quadrigeminealkaloids," Tetrahedron 2015, 71, pp. 6424-6436.
Carter et al., "High Level *Escherichia coli* Expression and Production of a Bivalent Humanized Antibody Fragment." Bio/Technology 10, 163-167 (1992).
Chaib et al., "Anti-leukemia activity of chaetocin via death receptor-dependent apoptosis and dual modulation of the histone methyl-transferase SUV39H1." Leukemia. Apr. 2012;26(4):662-74.
Chang, H.-H. et al., "Heterocyclic Compounds. Part 15. NN'-Di-t-Butylthiadiaziridine 1, 1-Dioxide:Synthesis and Reactions," J. Chem. Soc., Perkin Trans. 1, 1977, pp. 1601-1605.
Chen et al., "Ecology-based screen identifies new metabolites from a Cordyceps-colonizing fungus as cancer cell proliferation inhibitors and apoptosis inducers." Cell Prolif. Dec. 2009;42(6):838-47.
Cherblanc et al., "On the Determination of the Stereochemistry of Semisynthetic Natural Product Analogues using Chiroptical Spectroscopy: Desulfurization of Epidithiodioxopiperazine Fungal Metabolites." Chem.-Eur. J. 2011; 17(42):11868-11875.
Choi et al., "Agelastatin A (AgA), a Marine Sponge Derived Alkaloid, Inhibits Wnt/Beta-Catenin Signaling and Selectively Induces Apoptosis in Chronic Lymphocytic Leukemia Independently of p53," Blood (ASH Annual Meeting Abstracts), 118:Abstract1786, 2 pages (2011).
Chou et al., "Therapeutic Cure against Human Tumor Xenografts inNude Mice by a Microtubule Stabilization Agent,Fludelone, via Parenteral or Oral Route." Cancer Res. 2005; 65(20):9445-9454.
Codelli et al., "Enantioselective Total Synthesis of (−)-Acetylaranotin, a Dihydrooxepine Epidithiodiketopiperazine." J. Am. Chem. Soc. 2012; 134(4):1930-1933.

Coffen et al., "A short synthesis of aromatic analogues of the aranotins." J. Org. Chem. Mar. 18, 1977;42(6):948-52.
Coleman et al., "Antifungal activity of microbial secondary metabolites." PLoS One. 2011;6(9):e25321.
Collet, F. et al., "Catalytic C—H amination: recent progress and future directions," Chem. Commun. 2009, pp. 5061-5074.
Combeau et al., "RPR112378 and RPR115781: Two Representatives of a New Family of Microtubule Assembly Inhibitors." Molecular Pharmacology Mar. 2000; 57(3):553-563.
Cook et al., "Epidithiodiketopiperazines Block the Interaction between Hypoxia-inducible Factor-1α (HIF-1 α) and p300 by a Zinc Ejection Mechanism." J Biol. Chem. 2009; 284:26831-26838.
Coretese et al., "Podophyllotoxin as a probe for the colchicine binding site of tubulin." J Biol Chem. Feb. 25, 1977;252(4):1134-40.
Coste et al., Concise Total Synthesis of (+)-Bionectins A and C. Chem Sci. 2013;4(8):3191-3197. doi:10.1039/C3SC51150B.
Coussens et al., "Tyrosine kinase receptor with extensive homology to EGF receptor shares chromosomal location with neu oncogene." Science Dec. 6, 1985; 230(4730):1132-1139.
Crich et al., "Expedient Synthesis of threo-β-Hydroxy-α-amino Acid Derivatives: Phenylalanine, Tyrosine, Histidine, and Tryptophan." J. Org. Chem. 2006; 71(18):7106-7109.
Cushman et al., "Synthesis and evaluation of stilbene and dihydrostilbene derivatives as potential anticancer agents that inhibit tubulin polymerization." J. Med. Chem. 1991; 34(8):2579-2588.
Cushman et al., "Synthesis of Analogs of 2-Methoxyestradiol with Enhanced Inhibitory Effects on Tubulin Polymerization and Cancer Cell Growth." J. Med. Chem.1997; 40(15):2323-2334.
D'Ambrosia et al., "Agelastatin A, a New Skeleton Cytotoxic Alkaloid of the Oroidin Family. Isolation from the Axinellid Sponge Agelas dendromorpha of the Coral Sea," J. Chem. Soc., Chem. Commun., pp. 1305-1306 (1993).
D'Ambrosio et al., "The Active Centres of Agelastatin A, a Strongly Cytotoxic Alkaloid of the Coral Sea Axinellid Sponge Agelas dendromorpha, as Determined by Comparative Bioassays with Semisynthetic Derivatives," Helv. Chem. Acta, 79:727-735(1996).
De Groot et al., ""Cascade-release dendrimers" liberate all end groups upon a single triggering event in the dendritic core." Angew Chem Int Ed Engl. Sep. 29, 2003; 42(37):4490-4.
De Groot et al., "Design, Synthesis, and Biological Evaluation of a Dual Tumor-specific Motive Containing Integrin-targeted Plasmin-cleavable Doxorubicin Prodrug." Molecular Cancer Therapeutics 2002; 1(11):901-911.
De Groot et al., "Synthesis and Biological Evaluation of Novel Prodrugs of Anthracyclines for Selective Activation by the Tumor-Associated Protease Plasmin." J. Med. Chem. 1999; 42(25):5277-5283.
De Loera, D. et al., "Efficient Aziridine Synthesis in Metastable Crystalline Phases by Photoinduced Denitrogenation of Crystalline Triazolines," Org. Lett. 2012, vol. 14, No. 15, pp. 3874-3877.
De Loera, D. et al., "Photoinduced and Thermal Denitrogenation of Bulky Triazoline Crystals: Insights into Solid-to-Solid Transformation," J. Am. Chem. Soc. 2013, 135, pp. 6626-6632.
DeLorbe et al., "General Approach for Preparing Epidithiodioxopiperazines from Trioxopiperazine Precursors: Enantioselective Total Syntheses of (+)- and (−)-Gliocladine C, (+)-Leptosin D, (+)-T988C, (+)-Bionectin A, and (+)-Gliocladin A." J. Am. Chem. Soc. 2013; 135(10):4117-4128.
DeLorbe et al., Enantioselective Total Synthesis of (+)-Gliocladine C: Convergent Construction of Cyclotryptamine-Fused Polyoxopiperazines and a General Approach for Preparing Epidithiodioxopiperazines from Trioxopiperazine Precursors. J Am Chem Soc. Apr. 7, 2011;133(17):6549-52.
Denmark et al., "Palladium-Catalyzed Cross-Coupling Reactions of 2-Indolyldimethylsilanols with Substituted Aryl Halides." Org. Lett. 2004; 6(20):3649-3652.
Depew et al., "Total Synthesis of 5-N-Acetylardeemin and Amauromine: Practical Routes to Potential MDR Reversal Agents." J. Am. Chem. Soc.1999; 121(51):11953-11963.

(56) References Cited

OTHER PUBLICATIONS

Dippold et al., "Cell surface antigens of human malignant melanoma: definition of six antigenic systems with mouse monoclonal antibodies." Proc Natl Acad Sci U S A. Oct. 1980; 77(10): 6114-6118.
Dong et al., "Nematicidal epipolysulfanyldioxopiperazines from Gliocladium roseum." J Nat Prod. Oct. 2005;68(10):1510-3.
Dorr et al., "Antitumor activity of combretastatin-A4 phosphate, a natural product tubulin inhibitor." Invest. New Drugs Jun. 1996; 14(2):131-137.
Du Bois, J., "Rhodium-Catalyzed C—H Amination. An Enabling Method for Chemical Synthesis," Org. Process Res. Dev. 2011, 15, pp. 758-762.
Dubey et al., Direct organocatalytic coupling of carboxylated piperazine-2,5-diones with indoles through conjugate addition of carbon nucleophiles to indolenine intermediates. Tetrahedron Lett. 2010;51(4):609-612. doi:10.1016/j.tetlet.2009.11.068.
Dubowchik et al., "Monomethoxytrityl (MMT) as a versatile amino protecting group for complex prodrugs of anticancer compounds sensitive to strong acids, bases and nucleophiles." Tetrahedron Letters 1997; 38(30):5257-60.
Dubs et al., "Eine neue Methode zur Herstellung gemischter Disulfide. Vorläufige Mitteilung" Helv. Chim. Acta 1976; 59(4):1307-1311.
Ducki et al., "Potent antimitotic and cell growth inhibitory properties of substituted chalcones." Bioorg Med Chem Lett. May 5, 1998; 8(9):1051-6.
Engel, P. S. et al., "Thermolysis of Free-Radical Initiators: tert-Butylazocumene and Its 1,3- and 1,4-Bisazo and 1,3,5-Trisazo Analogues," J. Am. Chem. Soc. 2001, 123, pp. 3706-3715.
Engel, P. S., "Mechanism of the Thermal and Photochemical Decomposition of Azoalkanes," Chemical Reviews Apr. 1980, vol. 80, No. 2, 52 pages.
Engel, P. S., "Photochemistry of Aliphatic Azo Compounds in Solution," Accounts of Chemical Research 1973, vol. 6, pp. 275-281.
Espino, C. G. et al., "A Rh-Catalyzed C—H Insertion Reaction for the Oxidative Conversion of Carbamates to Oxazolidinones," Angew. Chem. Int. Ed. 2001, 40:3, pp. 598-600.
Espino, C. G. et al., "Expanding the Scope of C—H Amination through Catalyst Design," J. Am. Chem. Soc. 2004, 126, pp. 15378-15379.
Eto et al., Conformation of aromatic rings in isolable atropisomers of 2-arylindoline derivatives and kinetic evidences for π-π interaction. Tetrahedron Lett. Jan. 23, 2010;66(4):898-903.
Fang, C.-L. et al., "Dimerization of a 3-Substituted Oxindole at C-3 and Its Application to the Synthesis of (±)-Folicanthine," J. Am. Chem. Soc. 1994, 116, pp. 9480-9486.
Fink et al., "Mercaptoacyl Dipeptides as Orally Active Dual Inhibitors of Angiotensin-Converting Enzyme and Neutral Endopeptidase." J. Med. Chem.1996; 39(16):3158-3168.
Fiori, K. W. et al., "A mechanistic analysis of the Rh-catalyzed intramolecular C—H amination reaction," Tetrahedron 2009, 65, pp. 3042-3051.
Fiori, K. W. et al., "Catalytic Intermolecular Amination of C—H Bonds: Method Development and Mechanistic Insights," J. Am. Chem. Soc. 2007, 129, pp. 562-568.
Firouzabadi et al., "Bispyridinesilver permanganate[Ag(C5H5N)2]MnO4: an efficient oxidizing reagent for organic substrates." Tetrahedron Lett. 1982; 23(17): 1847-1850.
Flynn et al., "The synthesis and tubulin binding activity of thiophene-based analogues of combretastatin A-4." Bioorg Med Chem Lett. Sep. 3, 2001; 11(17):2341-3.
Foo, K. et al., "Total Synthesis-Guided Structure Elucidation of (+)-Psychotetramine," Angew. Chem. Int. Ed. Engl. 2011, 50(12), pp. 2716-2719.
Fotsis et al., "The endogenous oestrogen metabolite 2-methoxyoestradiol inhibits angiogenesis and suppresses tumour growth." Nature. Mar. 17, 1994; 368(6468):237-9.
Francisco et al., "Agonistic properties and in vivo antitumor activity of the anti-CD-40 antibody, SGN-14" Cancer Res. 2000; 60:3225-3231.
Frisch et al., "Synthesis of Short Polyoxyethylene-Based Heterobifunctional Cross-Linking Reagents. Application to the Coupling of Peptides to Liposomes." Bioconjugate Chem., 1996, 7(2), pp. 180-186.
Fukuyama et al., "A total synthesis of gliotoxin." J. Am. Chem. Soc. 1976; 98(21):6723-6724.
Fulmer et al., "NMR Chemical Shifts of Trace Impurities: Common Laboratory Solvents, Organics, and Gases in Deuterated Solvents Relevant to the Organometallic Chemist," Organometallics, 2010, 29 (9), pp. 2176-2179.
Furst, L. et al., "Total Synthesis of (+)-Gliocladin C Enabled by Visible-Light Photoredox Catalysis," Angew. Chem. Int. Ed. 2011, 50, pp. 9655-9659.
Gardiner et al., "The epipolythiodioxopiperazine (ETP) class of fungal toxins: distribution, mode of action, functions and biosynthesis." Microbiology. Apr. 2005; 151(Pt 4):1021-32.
Gardner et al., "Understanding C—H bond oxidations: H. and H-transfer in the oxidation of toluene by permanganate." Science. Sep. 29, 1995 269(5232):1849-51.
Gastpar et al., "Methoxy-Substituted 3-Formyl-2-phenylindoles Inhibit Tubulin Polymerization." J. Med. Chem.1998; 41(25):4965-4972.
Gerwick et al., "Structure of Curacin A, a Novel Antimitotic, Antiproliferative and Brine Shrimp Toxic Natural Product from the Marine Cyanobacterium Lyngbya majuscula." J. Org. Chem.1994; 59(6):1243-1245.
Getahun et al., "Synthesis of alkoxy-substituted diaryl compounds and correlation of ring separation with inhibition of tubulin polymerization: differential enhancement of inhibitory effects under suboptimal polymerization reaction conditions." J. Med. Chem. 1992; 35(6):1058-1067.
Gilow et al., "Sulfenylation of some pyrroles and indoles." J Heterocyclic Chem. 1991, 28(4):1025-1034.
Goldman et al., "Immunolocalization of neuroblastoma using radiolabeled monoclonal antibody UJ13A." J. Pediatr. 1984; 105:252-256.
Goldstraw et al., Non-small-cell lung cancer. Lancet 2011;378:1727-40.
Golitz, P. et al., "A New Method for the Introduction of Trifluoromethyl Groups," Angew. Chem. Int. Ed. Engl. 1977, 16, No. 12, pp. 854-855.
Govek, S. P. et al., "Total Synthesis of (+)-asperazine," Tetrahedron 2007, 63, pp. 8499-8513.
Greene, T. W. et al., "Greene's Protective Groups in Organic Synthesis," Fifth Edition, Wiley, New York, NY 2014, Chapter 7, "Protection for the Amino Group," 299 pages (Parts 1 & 2).
Greiner et al., "Identification of a specific inhibitor of the histone methyltransferase SU(VAR)3-9." Nat Chem Biol. Aug. 2005;1(3):143-5.
Gwaltney et al., "Novel sulfonate derivatives: potent antimitotic agents." Bioorg Med Chem Lett. Jul. 9, 2001; 11(13):1671-3.
Hadimani et al., "Synthesis, in vitro, and in vivo evaluation of phosphate ester derivatives of combretastatin A-4." Bioorg. Med. Chem. Lett. 2003; 13(9):1505-1508.
Hale et al., "Enantiospecific Formal Total Synthesis of the Tumor and GSK-3b Inhibiting Alkaloid, (−)-Agelastatin A," Org. Lett., 5(16):2927-2930 (2003).
Hall, E. S. et al., "Biogenetic-Type Synthesis of the Calycanthaceous Alkaloids," Tetrahedron 1967, 23, pp. 4131-4141.
Hamada et al., "Selective removal of electron-accepting p-toluene- and naphthalenesulfonyl protecting groups for amino function via photoinduced donor acceptor ion pairs with electron-donating aromatics." J. Am. Chem. Soc. 1986; 108(1):140-145.
Hammonds et al., "Studies to show that with podophyllotoxin the early replicative stages of herpes simplex virus type 1 depend upon functional cytoplasmic microtubules." J Med Microbiol. Sep. 1996; 45(3):167-72.
Han, S.-J. et al., "Evolution of a Unified, Sterodivergent Approach to the Synthesis of Communesin F and Perophoramidine," J. Org. Chem. 2015, 80, pp. 528-547.

(56) References Cited

OTHER PUBLICATIONS

Han et al., "Synthesis and Anticancer Activity of All Known (−)-Agelastatin Alkaloids," The Journal of Organic Chemistry, 78, p. 11970-11984 (2013).
Hansen et al., "A stereoselective synthetic approach to (2S,3R)-N-(1',1'-dimethyl-2',3'-epoxypropyl)-3-hydroxytryptophan, a component of cyclomarin A." Tetrahedron: Asymmetry 2006; 17(1):15-21.
Hatanaka et al., "Novel B-ring modified combretastatin analogues: syntheses and antineoplastic activity." Bioorg Med Chem Lett. Dec. 1, 1998; 8(23):3371-4.
Hay et al., "A 2-nitroimidazole carbate prodrug of 5-amino-1-(chloromethyl)-3-[(5,6,7-trimethoxyindol-2-yl)carbonyl]-1,2-dihydro-3H-benz[e]indole (amino-seco-CBI-TMI) for use with ADEPT and GDEPT." Bioorg. Med. Chem. Lett. 1999; 9:2237-2242.
He et al., Total Syntheses of (−)-Asperlicin and (−)-Asperlicin C. J Am Chem Soc. Jun. 11, 1998;120(25):6417-8.
Hellström et al., "Antitumor effects of L6, an IgG2a antibody that reacts with most human carcinomas." Proc Natl Acad Sci U S A. Sep. 1986; 83(18): 7059-7063.
Hendrickson, J. B. et al., "Total Synthesis of the Calycanthaceous Alkaloids. Chimonanthine," R. Proc. Chem. Soc. 1962, pp. 383-384.
Herscheid et al., "Biosynthesis of gliotoxin. Synthesis of sulfur-bridged dioxopiperazines from N-hydroxyamino acids." J. Org. Chem. 1980; 45(10):1885-1888.
Higuchi et al., First Total Synthesis of Hinckdentine A. Org Lett. 2009;11(1):197-9.
Higuchi et al., Preparation of 2,2-disubstituted 1,2-dihydro-3H-indol-3-ones via oxidation of 2-substituted indoles and Mannich-type reaction. Tetrahedron Lett. Feb. 6, 2010;66(6):1236-43.
Hino et al., "Synthesis of 3,6-diethoxycarbonyl-3,6-epipolythia-2,5-piperazinedione derivatives." Tetrahedron Lett. 1971; 12(33):3127-3129.
Hino, T. et al., "Oxidative Dimerization of Nb-Methoxycarbonyltryptamines by Dye-Sensitized Photooxygenation in Formic Acid. Synthesis of (±)-Folicanthine and (±)-Chimonanthine," Tetrahedron Letters 1978, 49, pp. 4913-4916.
Hino, T. et al., "Total Synthesis of (±)-Folicanthine," Tetrahedron Letters 1963, 25, pp. 1757-1760.
Hoijemberg, P. A. et al., "Photolysis of an asymmetrically substituted diazene in solution and in the crystalline state," Photochem. Photobiol. Sci. 2009, 8, pp. 961-969.
Holwell et al., "Anti-vascular effects of vinflunine in the MAC 15A transplantable adenocarcinoma model." Br. J. Cancer., 2001; 84:290-295.
Hoogenboom et al., "By-passing immunisation. Human antibodies from synthetic repertoires of germline VH gene segments rearranged in vitro." J Mol Biol. Sep. 20, 1992; 227(2):381-8.
Hossain, T. Md. et al., "Synthesis of Bisbicyclo[1.1.1]pentyldiazene. The Smallest Brigehead Diazene," J. Org. Chem. 2001, 66, pp. 6282-6285.
Hsieh et al., "Structure-activity and crystallographic analysis of benzophenone derivatives—the potential anticancer agents." Bioorg Med Chem Lett. 2002; 13(1):101-105.
Huang et al., "Diketopiperazines from Marine Organisms." Chem. Biodiv. 2010; 7(12):2809-2829.
Huard, K. et al., "N-Tosyloxycarbamates as Reagents in Rhodium-Catalyzed C—H Amination Reactions," Chem. Eur. J. 2008, 14, pp. 6222-6230.
Huston et al., "Protein engineering of antibody binding sites: recovery of specific activity in an anti-digoxin single-chain Fv analogue produced in Escherichia coli." Proc Natl Acad Sci U S A. Aug. 1988; 85(16):5879-5883.
Ikeda, H. et al., "Evidence for Significant Through-Space and Through-Bond Electronic Coupling in the 1,4-Diphenylcyclohexane-1,4-diyl Radical Cation Gained by Absorption Spectroscopy and OFT Calculations," Chem. Eur. J. 2007, 13, DD. 9207-9215.
Isham et al., "Chaetocin: a promising new antimyeloma agent with in vitro and in vivo activity mediated via imposition of oxidative stress." Blood. Mar. 15, 2007;109(6):2579-88.
Isham et al., "The anticancer effects of chaetocin are independent of programmed cell death and hypoxia, and are associated with inhibition of endothelial cell proliferation." Br J Cancer. Jan. 17, 2012;106(2):314-23.
Ishikawa, H. et al., "Dimerization of indole derivatives with hypervalent iodines(III): a new entry for the concise total synthesis of rac- and meso-chimonanthines," Tetrahedron Lett. 2002, 43, pp. 5637-5639.
Iwasa et al., "Total Synthesis of (+)-Chaetocin and its Analogues: Their Histone Methyltransferase G9a Inhibitory Activity." J. Am. Chem. Soc. 2010; 132(12):4078-4079.
Iwasa, E. et al., "Total Synthesis of (±)-Chaetocin and its Analogues: Their Histone Methyltransferase G9a Inhibitory Activity," J. Am. Chem. Soc. 2010, 132, pp. 4078-4079.
Iwasa, et al., "Epipolythiodiketopiperazine Alkaloids: Total Syntheses and Biological Activities." Isr. J Chem. 2011; 51(3-4):420-433.
Jamison, C. R. et al., "Enantioselective Synthesis of Polypyrroloindolines by Controlled Oligomerization," Nat. Chem. 2017, doi: 10.1038/nchem.2825, 1 page.
Janik et al., "Synthesis and antimicrobtubule activity of combretatropone derivatives." Bioorg. Med. Chem. Lett. 2002; 10:1895-1903.
Jannic, V. et al., Pyrrolidinoindoline alkaloids from Psychotria oleoides and Psychotria lyciiflora. J Nat Prod. Jun. 1999;62(6):838-43.
Jespers et al., "Guiding the selection of human antibodies from phage display repertoires to a single epitope of an antigen." Biotechnology (N Y). Sep. 1994; 12(9):899-903.
Jiang et al., "Disulfide- and Multisulfide-Containing Metabolites from Marine Organisms." Chem. Rev. 2012; 112(4):2179-2207.
Jiang et al., "Epipolythiodioxopiperazines from fungi: chemistry and bioactivities." Mini Rev Med Chem. Aug. 2011;11(9):728-45.
Jiang et al., "Synthesis and biological evaluation of 2-styrylquinazolin-4(3H)-ones, a new class of antimitotic anticancer agents which inhibit tubulin polymerization." J. Med. Chem.1990; 33(6):1721-1728.
Jones et al., "Replacing the complementarity-determining regions in a human antibody with hose from a mouse." Nature. May 29-Jun. 4, 1986;321(6069):522-5.
Jordan et al., "Fungal epipolythiodioxopiperazine toxins have therapeutic potential and roles in disease." Trends Pharmacol. Sci. 8, 144-149.
Jouanneau et al., "Derivatization of agelastatin A leading to bioactive analogs and a trifunctional probe," Bioorganic & Medicinal Chemistry Letters, 26, p. 2092-2097 (2016).
Kabat et al., "Origins of antibody complementarity and specificity—hypervariable regions and minigene hypothesis." J Immunol Sep. 1, 1980; 125(3):961-969.
Kakeya, et al., "Studies on Prodrugs of Cephalosporins. I. Synthesis and Biological Properties of Glycyloxybenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid." Chem. Pharm. Bull. 1984 32(2):692-698.
Kaneko et al., "New hydrazone derivatives of Adriamycin and their immunoconjugates—a correlation between acid stability and cytotoxicity." Bioconjugate Chem.1991; 2(3):133-141.
Kanoh et al., "(−)-Phenylahistin arrests cells in mitosis by inhibiting tubulin polymerization." J Antibiot (Tokyo). Feb. 1999; 52(2):134-41.
Kapoor, "Inhibition of osteopontin dependent carcinogenesis," J. Cancer Res. Clin. Oncol., 134, p. 927-928 (2008).
Karaman et al., "Preparation and properties of quaternary ammonium and phosphonium permanganates." J. Org. Chem.1984; 49(23):4509-4516.
Kennett et al., "Hybrid myelomas producing antibodies against a human neuroblastoma antigen present on fetal brain." Science ar. 16, 1979: 203(4385):1120-1121.
Kieffer, M. E. et al., "Copper-Catalyzed Diastereoselective Arylation of Tryptophan Derivatives: Total Synthesis of (+)-Naseseazines A and B," J. Am. Chem. Soc. 2013, 135(15), pp. 5557-5560.
Kim et al., "Alkylthiolation of allylic sulfides. [2,3] Sigmatropic rearrangement of thiosulfonium ions." J. Org. Chem. 1979; 44(12):1897-1904.

(56) References Cited

OTHER PUBLICATIONS

Kim et al., General approach to epipolythiodiketopiperazine alkaloids: total synthesis of (+)-chaetocins A and C and (+)-12,12'-dideoxychetracin A. J Am Chem Soc. Oct. 20, 2010;132(41):14376-8. doi: 10.1021/ja106869s.
Kim et al., Total synthesis of (+)-11, 11 '-dideoxyverticillin A, Science. 2009;324(5924):238-41.
Kim, H. et al., "Transition-Metal-Mediated Direct C—H Amination of Hydrocarbons with Amine Reactants: The Most Desirable but Challenging C—N Bond-Formation Approach," ACS Catal. 2016, 6, pp. 2341-2351.
Kim, J. et al., "Biogenetically-Inspired Total Synthesis of Epidithiodiketopiperazines," Acc. Chem. Res. 2015, 48, pp. 1159-1171.
King et al., "Facile synthesis of maleimide bifuntional linkers," Tetrahedron Lett. 2002; 43:1987-1990.
Kingsbury et al., "A novel peptide delivery system involving peptidase activated prodrugs as antimicrobial agents. Synthesis and biological activity of peptidyl derivatives of 5-fluorouracil." J. Med. Chem. 1984; 27:1447-1451.
Kingston et al., "The Chemistry of Taxol, a Clinically Useful Anticancer Agent." J. Nat. Prod. 1990; 53(1):1-12.
Kishi et al., "Total synthesis of dehydrogliotoxin." J. Am. Chem. Soc. 1973; 95(19):6492-6493.
Kishi et al., "Total synthesis of sporidesmin A." J. Am. Chem. Soc. 1973; 95(19):6493-6495.
Kobayashi et al., "Synthetic study on an antitumor antibiotic rhizoxin by using an enzymatic process on prochiral β-substituted glutarates." Pure Appl. Chem. 1992; 64(8):1121-1124.
Kodanko, J. J. et al., "Enantioselective Total Syntheses of the Cyclotryptamine Alkaloids Hodgkinsine and Hodgkinsine B," Angew. Chem. Int. Ed. 2003, 42, pp. 2528-2531.
Kodanko, J. J. et al., "Synthesis of All Low-energy Stereoisomers of the Tris(pyrrolidinoindoline) Alkaloid Hodgkinsine and Preliminary Assessment of Their Antinociceptive Activity," J. Org. Chem. 2007, 72, pp. 7909-7914.
Köhler et al., "Continuous cultures of fused cells secreting antibody of predefined specificity." Nature 256, 495-497 (1975).
Kosower, E. M., "Monosubstituted Diazenes (Diimides). Suprising Intermediates," Accounts ofChemical Research 1971, vol. 1, No. 6, pp. 193-198.
Kozbor, Immunology Today, vol. 4, 1983, pp. 72-79.
Kricheldorf, H.R. "Synthese von Isothiocyanatocarbonsäurechloriden aus Lactamen." Angew. Chem. 1975; 87(14):517.
Kroutil et al., "First preparative biocatalytic hydrolysis and S-methylation of cyclic trithiocarbonates." Tetrahedron 2002; 58(13):2589-2592.
Kung et al., "Small molecule blockade of transcriptional coactivation of the hypoxia-inducible factor pathway." Cancer Cell. Jul. 2004;6(1):33-43.
Kurokawa, T. et al., "Synthesis of 1,3-Diamines Through Rhodium-Catalyzed C—H Insertion," Angew. Chem. Int. Ed. 2009, 48, pp. 2777-2779.
Kyoizumi et al., "Monoclonal antibodies to human squamous cell carcinoma of the lung and their application to tumor diagnosis." Cancer Res. Jul. 1985; 45(7):3274-81.
Laguzza et al., "New antitumor monoclonal antibody-vinca conjugates LY203725 and related compounds: design, preparation, and representative in vivo activity." J. Med. Chem. 1989; 32(3):548-555.
Langer, R., "New methods of drug delivery," Science Sep. 28, 1990: vol. 249, Issue 4976, pp. 1527-1533.
Lavielle et al., "New .alpha.-amino phosphonic acid derivatives of vinblastine: chemistry and antitumor activity." J. Med. Chem.1991; 34(7):1998-2003.
Lawrence et al., "The interaction of chalcones with tubulin." Anticancer Drug Des. Apr. 2000; 15(2):135-41.
Lee et al., "Antihepatoma activity of chaetocin due to deregulated splicing of hypoxia-inducible factor 1 α pre-mRNA in mice and in vitro." Hepatology. Jan. 2011;53(1):171-80.

Leoni et al., "Indanocine, a microtubule-binding indanone and a selective inducer of apoptosis in multidrug-resistant cancer cells." J Natl Cancer Inst. Feb. 2, 2000;92(3):217-24.
Li et al., "An integrated approach to the discovery of potent agelastatin A analogues for brain tumors: chemical synthesis and biological, physicochemical and CNS pharmacokinetic analyses," Med. Chem. Commun., 4, p. 1093-1098 (2013).
Li et al., General Approach for the Synthesis of Ajmaline/Sarpagine Indole Alkaloids: Enantiospecific Total Synthesis of (+)-Ajmaline, Alkaloid G, and Norsuaveoline via the Asymmetric Pictet—Spengler Reaction. J Am Chem Soc. Jul. 16, 1999;121(30):6998-7010.
Li et al., Ligand-based targeted therapy: a novel strategy for hepatocellular carcinoma. Int J Nanomedicine. Oct. 31, 2016;11:5645-5669. eCollection 2016.
Liang et al., Organocatalytic stereoselective conjugate addition of 3-substituted oxindoles with in situ generated ortho-quinone methides. Tetrahedron Lett. May 2, 2018;59(18):1742-7.
Libot, F. et al., "Biomimetic Transformation of Hodgkinsine, a Pyrrolidinoindoline Alkaloids," Heterocycles 1988, 27, pp. 2381-2386.
Libot, F. et al., "Rubiacees D'Oceanie: Alcalo'ldes de Psychotria Oleoides de Nouvelle-Caledonie et de Calycodendron Milnei du Vanuatu (Nouvelles-Hebrides)," Journal of Natural Products 1987, vol. 50, No. 3, pp. 468-473.
Lim, Y.-K. et al., "Novel Route to Azobenzenes via Pd-Catalyzed Coupling Reactions of Aryl Hydrazides with Aryl Halides, Followed by Direct Oxidations," Org. Lett. 2003, vol. 5, No. 7, pp. 979-982.
Lin et al., "Antimitotic natural products combretastatin A-4 and combretastatin A-2: studies on the mechanism of their inhibition of the binding of colchicine to tubulin." Biochemistry 1989; 28(17):6984-6991.
Lindovska, P. et al., "Concise Synthesis of (−)-Hodgkinsine, (−)-Calycosidine, (−)-Hodgkinsine B, (−)- Quadrigemine C, and (−)-Psycholeine via Convergent and Directed Modular Assembly of Cyclotryptamines," https://www.ncbi.nlm.nih.gov/m/pubmed/29058431, 2017, 7 pages.
Link, J. T. et al., "Stereocontrolled Total Syntheses of meso-Chimonanthine and meso-Calycanthine via a Novel Samarium Mediated Reductive Dialkylation," J. Am. Chem. Soc. 1996, 118, pp. 8166-8167.
Little, R. D. et al., "Total Synthesis of the Marine Natural Product i19(121-Capnellene. Reversal ofRegiochemistry in the Intramolecular 1,3-Diyl Trapping Reaction," J. Am. Chem. Soc. 1983, 105, pp. 928-932.
Little, R. D., "Diyl Trapping and Electroreductive Cyclization Reactions," Chem. Rev. 1996, 96, pp. 93-114.
Liu et al., "Chimeric Mouse-Human IgG1 Antibody That Can Mediate Lysis of Cancer Cells." Proc. Natl. Acad. Sci., USA May 1987; 84:3439-3443.
Liu et al., "Production of a Mouse-Human Chimeric Monoclonal Antibody to CD20 with Potent Fc-Dependent Biologic Activity." J. Immunol. Nov. 1987; 139:3521-3526.
Liu et al., "Verticillin A overcomes apoptosis resistance in human colon carcinoma through DNA methylation-dependent upregulation of BNIP3." Cancer Res. Nov. 1, 2011;71(21):6807-16.
Mahboobi et al., "Synthetic 2-Aroylindole Derivatives as a New Class of Potent Tubulin-Inhibitory, Antimitotic Agents." J. Med. Chem. 2001; 44(26):4535-4553.
Mannila et al., "Combretastatin Analogs via Hydration of Stilbene Derivatives." Liebigs. Ann. Chem. 1993; 1993(9):1037-1039.
March, "Advanced Organic Chemistry," Third Edition: John Wiley & Sons, inc. New York, NY, Chapter 1, "Localized Chemical Bonding" n pp. 16-18.
Marks et al., "By-passing immunization. Human antibodies from V-gene libraries displayed on phage." J Mol Biol. Dec. 5, 1991; 222(3):581-97.
Mascitti, V. et al., "Total Synthesis of (±)-Pentacycloanammoxic Acid," J. Am. Chem. Soc. 2004, 126, pp. 15664-15665.
Mason et al., "Agelastatin A: a novel inhibitor of osteopontin-mediated adhesion, invasion, and colony formation," Mol. Cancer Ther., 7:548-558 (2008).

(56) References Cited

OTHER PUBLICATIONS

Matano et al., "Synthesis and Charge-Carrier Transport Properties of Poly(phosphole P-alkanesulfonylimide)s," Org. Lett., 2013, 15 (4), pp. 932-935.
Matsuda, Y. et al., "Total Synthesis and Structure Reinvestigation of So-Called Isochimonanthine," Heterocycles 2005, 65, pp. 1031-1033.
Medarde et al., "Synthesis and antineoplastic activity of combretastatin analogues: Heterocombretastatins." Eur. J. Med. Chem., 1998; 33(1)71-77.
Medarde et al., "Synthesis and pharmacological activity of combretastatin analogues. Naphthylcombretastatins and related compounds." Bioorganic. Med. Chem. Lett. 1995; 5(3):229-232.
Medarde et al., "Synthesis and pharmacological activity of diarylindole derivatives. Cytotoxic agents based on combretastatins." Bioorg Med Chem Lett. Aug. 1, 1999; 9(16):2303-2308.
Medina et al., "Novel antineoplastic agents with efficacy against multidrug resistant tumor cells." Bioorg Med Chem Lett. Oct. 6, 1998; 8(19):2653-6.
Merchant et al., "An efficient route to human bispecific IgG." Nat Biotechnol. Jul. 1998;16(7):677-81.
Miknis et al., "Total synthesis of (.+-.)-aspirochlorine." J. Am. Chem. Soc. 1993; 115(2):536-547.
Miller et al., "Specific Inhibition of Viral Ribonucleic Acid Replication by Gliotoxin." Science Jan. 26, 1968; 159(3813):431-432.
Miller et al., "Treatment of B-Cell Lymphoma with Monoclonal Anti-Idiotype Antibody." N Engl J Med 1982; 306:517-522.
Milstein et al., "Hybrid hybridomas and their use in immunohistochemistry." Nature. Oct. 6-12, 1983;305(5934):537-40.
Moody et al., "Dirhodium(II) tetraacetate catalysed reactions of diazo thioamides: isolation and cycloaddition of anhydro-4-hydroxy-1,3-thiazolium hydroxides (thioisomünchnones), an approach to analogues of dehydrogliotoxin." Org. Biomol. Chem. 2003;1(15):2716-2722.
Morrison, S.L, "Transfectomas provide novel chimeric antibodies." Science Sep. 20, 1985; 229(4719):1202-1207.
Movassaghi et al., Total Synthesis of All (−)-Agelastatin Alkaloids Asymmetric Synthesis Ii: More Methods and Applications. 2013;391-396. DOI: 10.1002/9783527652235.ch49.
Movassaghi et al., Total synthesis of all (−)-agelastatin alkaloids. Chem. Sci. 2010;1:561-66.
Movassaghi, M. et al., "Concise Total Synthesis of (+)-WIN 64821 and (−)-Ditryptophenaline," Angew. Chem. Int. Ed. 2008, 47, pp. 1485-1487.
Mu et al, "Synthesis, anticancer activity, and inhibition of tubulin polymerization by conformationally restricted analogues of lavendustin A." J Med Chem. Apr. 24, 2003; 46(9):1670-82.
Müllbacher et al., "Structural relationship of epipolythiodioxopiperazines and their immunomodulating activity." Molec. Immunol. Feb. 1986; 23(2):231-235.
Nakada et al., "The first total synthesis of the antitumor macrolide, rhizoxin." Tetrahedron Lett., 1993; 34(6):1039-1042.
Nakagawa, M. et al., "Oxidative Dimerization of Nb-Acyltryptophans Total Synthesis and Absolute Configuration of Ditryptophenaline," Tetrahedron Letters 1981, vol. 22, No. 52, pp. 5323-5326.
Nam et al., "Combretastatin A-4 analogues as antimitotic antitumor agents." Curr Med Chem. Sep. 2003; 10(17):1697-722.
Nam et al., "Synthesis and anti-tumor activity of novel combretastatins: combretocyclopentenones and related analogues." Bioorg Med Chem Lett. 2002; 12(15):1955-1958.
Nascimento, R. R. G. et al., "New Alkaloids from Margaritopsis carrascoana (Rubiaceae)," J. Braz. Chem. Soc. 2015, vol. 26, No. 6, pp. 1152-1159.
Nelsen, S. F. et al., "Azocumene. I. Preparation and Decomposition of Azocumene. Unsymmetrical Coupling Products of the Cumyl Radical," Journal of the American Chemical Society, Jan. 5, 1966, 88:1, pp. 137-143.

Nelson, H. M. et al., "Chiral Anion Phase Transfer of Aryldiazonium Cations: An EnantioselectiveSynthesis of C3-Diazenated Pyrroloindolines," Angew. Chem. Int. Ed. 2014, 53, pp. 5600-5603.
Neuman, R. C. et al., "cis-Diazenes. Viscosity Effects, One-Bond Scission, and Cis-Trans Isomerization," J. Org. Chem. 1990, 55, pp. 2682-2688.
Nguyen-Hai et al., "Combretoxazolones: synthesis, cytotoxicity and antitumor activity." Bioorg. Med. Chem. Lett. 2001; 11(23):3073-3076.
Nicolaou et al., "A Practical Sulfenylation of 2,5-Diketopiperazines." Angem. Chem. Int. Ed. 2012; 51(3):728-732.
Nicolaou et al., "Synthesis of epothilones A and B in solid and solution phase." Nature. May 15, 1997;387(6630):268-72.
Nicolaou et al., "Total Synthesis of Epicoccin G." J. Am. Chem. Soc. 2011; 133(21):8150-8153.
Nielsenw et al., "Glycolamide Esters as Biolabile Prodrugs of Carboxylic Acid Agents: Synthesis, Stability, Bioconversion, and Physicochemical Properties." J. Pharma. Sciences. 1988; 77(4):285-298.
Nishida et al., "Fungal metabolite gliotoxin targets flavocytochrome b558 in the activation of the human neutrophil NADPH oxidase." Infect Immun. Jan. 2005;73(1):235-44.
Nishimura et al., "Recombinant human-mouse chimeric monoclonal antibody specific for common acute lymphocytic leukemia antigen." Cancer Res. Feb. 15, 1987;47(4):999-1005.
Oguri et al., "Amino Acids and Peptides. XXIX. A New Efficient Asymmetric Synthesis of α-Amino Acid Derivatives with Recycle of a Chiral Reagent-Asymmetric Alkylation of a Chiral Schiff Base from Glycine." Chem. Pharm. Bull. 1978; 26(3):803-808.
Ohme, R. et al., "Preparation of Azo Compounds from N,N'-Dialkylsulfamides," Angew. Chem. Internat. Edit. 1965, vol. 4, No. 5, p. 433.
Okabe et al., "Elimination of Small Cell Lung Cancer Cells in Vitro from Human Bone Marrow by a Monoclonal Antibody." Cancer Res. May 1985; 45:1930-1933.
Okoth et al., "End-labeled amino terminated monotelechelic glycopolymers generated by ROMP and Cu(I)-catalyzed azide—alkyne cycloaddition," Beilstein J. Org. Chem. 2013, 9, 608-612.
Olsson et al., "[1] Human-human monoclonal antibody-producing hybridomas: Technical aspects." Meth. Enzymol. 1983; 92:3-16.
Oshumi et al., "Novel Combretastatin Analogues Effective against Murine Solid Tumors: Design and Structure—Activity Relationships." J. Med. Chem.1998; 41(16):3022-3032.
Oshumi et al., "Syntheses and antitumor activity of cis-restricted combretastatins: 5-membered heterocyclic analogues." Bioorg Med Chem Lett. Nov. 17, 1998; 8(22):3153-8.
Ottenheijm et al., "Approaches to analogs of dehydrogliotoxin. 6. An efficient synthesis of a gliotoxin analog with anti-reverse transcriptase activity." J. Org. Chem. 1976: 41(21):3433-3438.
Overman et al., "Construction of Epidithiodioxopiperazines by Directed Oxidation of Hydroxyproline-Derived Dioxopiperazines." Org. Lett. 2007; 9(25):5267-5270.
Overman, L. E. et al., "Direct Stereo- and Enantiocontrolled Synthesis of Vicinal Stereogenic Quaternary Carbon Centers. Total Synthesis of meso- and (−)-Chimonanthine and (+)-Calycanthine," J. Am. Chem. Soc. 1999, 121, pp. 7702-7703.
Overman, L. E. et al., "Enantioselective Construction of Vicinal Stereogenic Quaternary Centers by Dialkylation: Practical Total Syntheses of(+)- and meso-Chimonanthine," Angew. Chem. Int. Ed. 2000, vol. 39, No. 1, pp. 213-215.
Overman, L. E. et al., "Enantioselective synthesis of (−)-idiospermuline," Tetrahedron 2003, 59, pp. 6905-6919.
Overman, L. E. et al., "Enantioselective Total Synthesis of (+)-Gliocladin C," Org. Lett. 2007, 9(2), pp. 339-341.
Overman, L. E. et al., "Enantioselective Total Synthesis of the Cyclotryptamine Alkaloid Idiospermuline," Angew. Chem. Int. Ed. 2003, 42, pp. 2525-2528.
Overman, L. E. et al., "The Cyanomethyl Group for Nitrogen Protection and lminium Ion Generation in Ring-Enlarging Pyrrolidine Annulations. A short Synthesis of the Amaryllidaceae Alkaloid d, 1-Crinine," Tetrahedron Lett. 1982, 23, pp. 2741-2744.

(56) References Cited

OTHER PUBLICATIONS

Owellen et al., "Inhibition of tubulin-microtubule polymerization by drugs of the Vinca alkaloid class." Cancer Res. Apr. 1976; 36(4):1499-502.
Pahl et al., "The immunosuppressive fungal metabolite gliotoxin specifically inhibits transcription factor NF-kappaB." J Exp Med. Apr. 1, 1996; 183(4): 1829-1840.
Pangborn et al., "Safe and Convenient Procedure for Solvent Purification," Organometallics, 1996, 15 (5), pp. 1518-1520.
Patel et al., "Straightforward access to protected syn alpha-amino-beta-hydroxy acid derivatives." Angew Chem Int Ed Engl. 2008; 47(22):4224-7.
Patron et al., "Origin and distribution of epipolythiodioxopiperazine (ETP) gene clusters in filamentous ascomycetes." BMC Evolutionary Biology 2007; 7:174.
Perez-Balado, C. et al., "Expedient Total Synthesis of WIN 64745 and WIN 64821," Org. Lett. 2008, vol. 10, No. 17, pp. 3701-3704.
Perez-Balado, C. et al., "Stereocontrolled and Versatile Total Synthesis of Bispyrrolidinoindoline Diketopiperazine Alkaloids: Structural Revision of the Fungal Isolate (+)-Asperdimin," Chem. Eur. J. 2009, 15, pp. 9928-9937.
Pettit et al., "Antineoplastic agents 365. Dolastatin 10 SAR probes." Anticancer Drug Des. Jun. 1998; 13(4):243-77.
Pettit et al., "Antineoplastic Agents 470. Absolute Configuration of the Marine Sponge Bromopyrrole Agelastatin A," Oncol. Res., 15:11-20 (2005).
Pettit et al., "Antineoplastic Agents, 122. Constituents of Combretum caffrum." J. Nat. Prod. 1987; 50(3):386-391.
Pettit et al., "Antineoplastic agents. 113. Synthesis of natural (−)-combretastatin." J. Org. Chem. 1985; 50(18):3404-3406.
Pettit et al., "Antineoplastic agents. 257. Isolation and structure of spongistatin 1." J. Org. Chem.1993; 58(6):1302-1304.
Pettit et al., "Antineoplastic Agents. 291. Isolation and Synthesis of Combretastatins A-4, A-5, and A-6." J. Med. Chem. 1995; 38(10):1666-1672.
Pettit et al., "Antineoplastic Agents. 443. Synthesis of the Cancer Cell Growth Inhibitor Hydroxyphenstatin and Its Sodium Diphosphate Prodrug." J. Med. Chem. 2000; 43(14):2731-2737.
Pettit et al., "Antineoplastic agents. 487. Synthesis and biological evaluation of the antineoplastic agent 3,4-methylenedioxy-5,4'-dimethoxy-3'-amino-Z-stilbene and derived amino acid amides." J Med Chem. Feb. 13, 2003; 46(4):525-31.
Pettit et al., "cation salts, combretastatin A-3, diphosphate, prodrugs." Anti-Cancer Drug Design 2000: 15(6):397-403.
Pettit et al., "Isolation and structure of combretastatin." Canadian Journal of Chemistry, 1982, 60(11): 1374-137.
Pettit et al., "The isolation and structure of a remarkable marine animal antineoplastic constituent: dolastatin 10." J. Am. Chem. Soc.1987; 109(22):6883-6885.
Pinney et al., "A new anti-tubulin agent containing the benzo[b]thiophene ring system." Bioorg Med Chem Lett. Apr. 19, 1999; 9(8):1081-6.
Pinney et al., "Synthesis and biological evaluation of aryl azide derivatives of combretastatin A-4 as molecular probes for tubulin." Bioorg Med Chem. Oct. 2000; 8(10):2417-25.
Poisel et al., "Syntheseversuche in der Reihe der 3.6-Epidithio-2.5-dioxo-piperazin-Antibiotika Gliotoxin, Sporidesmin, Aranotin and Chaetocin, II." Chem. Ber., 1971; 104(6):17141721.
Polaske et al., "Enantioselective organocatalytic α-sulfenylation of substituted diketopiperazines." Tetrahedron: Asym. 2009; 20(23):2742-2750.
Porter, N. A. et al., "Diazenyl Radicals: A 15N CIDNP and Radical Trapping Study of Unsymmetric Diazenes," Journal of the American Chemical Society Feb. 1, 1978, 100:3, pp. 920-925.
Porter, N. A. et al., "Photolysis of Unsymmetric Azo Compounds. Cis Azo Compound Intermediates," Journal of the American Chemical Society Jun. 27, 1973, 95:13, pp. 4361-4367.
Pubchem CID 161244 deposited on Mar. 27, 2005, pp. 1-15.
Pubchem CID 18624123 deposited on Dec. 4, 2007, pp. 1-12.
Pubchem CID 69829071 deposited on Dec. 1, 2012, pp. 1-12.
Rao et al., "Radical mediated enantioselective construction of C-1 to C-9 segment of rhizoxin." Tetrahedron Lett. 1992; 33(27):3907-3910.
Rao et al., "Studies directed towards the total synthesis of rhizoxin: Stereoselective synthesis of C-12 to C-18 segment." Tetrahedron Lett. 1993; 34(4):707-710.
Rasolonjanahary, R. et al., "Psycholeine, a natural alkaloid extracted from Psychotria oleoides, acts as a weak antagonist of somatostatin," European Journal of Pharmacology 1995, 285, pp. 19-23.
Rautio et al., "Prodrugs: design and clinical applications." Nat Rev Drug Discov. Mar. 2008; 7(3):255-70.
Rautio, J. (Ed), Prodrugs and Targeted Delivery, Wiley, 2011.
Rezanka et al., "Pharmacologically Active Sulfur-Containing Compounds." Anti-Infect. Agents Med. Chem., 2006; 5(2):187-224.
Rightsel et al., "Antiviral Activity of Gliotoxin and Gliotoxin Acetate." Nature. Dec. 26, 1964;204:1333-4.
Rodrigues et al., "Engineering Fab' fragments for efficient F(ab)2 formation in Escherichia coli and for improved in vivo stability." J Immunol. Dec. 15, 1993. 151(12):6954-6961.
Rodrigues et al., "Synthesis and beta-lactamase-mediated activation of a cephalosporin-taxol prodrug." Chem Biol. Apr. 1995; 2(4):223-7.
Roizen, J. L. et al., "Metal Catalyzed Nitrogen-Atom Transfer methods for the Oxidation of Aliphatic C—H Bonds," Accounts of Chemical Research, Jan. 10, 2012, vol. 45, No. 6, pp. 911-922.
Ross et al., "The Chemistry of Methyl Vinyl Ketone. II. Reactions with Esters, β-Keto Esters, Malonic Ester, Amines, Tar Bases, and Inorganic Salts." J. Org. Chem. 1964; 29(8):2346-2350.
Rowland et al., "Antitumor properties of vindesine-monoclonal antibody conjugates." Cancer Immunol. Immunother. Feb. 1985; 19(1):1-7.
Ruff et al., "Thiolation of symmetrical and unsymmetrical diketopiperazines." Org. Biomol. Chem. 2012; 10(5):935-940.
Saad, H.-E. A. et al., "Biological Activities of Pyrrolidinoindoline Alkaloids from Calycodendron milnei," Planta Med. 1995, 61, pp. 313-316.
Sala et al., "Tetrabutylammonium permanganate: an efficient oxidant for organic substrates." J. Chem. Soc., Chem. Commun. 1978; 253-254.
Salayova et al., Stereoselective synthesis of 1-methoxyspiroindoline phytoalexins and their amino analogues. Tetrahedron: Asymmetry. Sep. 15, 2014;24(16-17):1221-33.
Schammel, A. W. et al., "Exploration of the interrupted Fischer indolization reaction," Tetrahedron 2010, 66, pp. 4687-4695.
Schiff et al., "Promotion of microtubule assembly in vitro by taxol." Nature 1979; 277:665-667.
Schumacher et al., "Potent Antitumor Activity of 2-Methoxyestradiol in Human Pancreatic Cancer Cell Lines." Clin. Cancer Res. 1999; 5(3):493-499.
Scott, A. I. et al., "Reaction Pathways in the Photochemical Conversion of Diphenylamines toCarbazoles," J. Am. Chem. Soc. 1964, 86, pp. 302-303.
Sevier et al., "Formation and transfer of disulphide bonds in living cells." Nat Rev Mol Cell Biol. Nov. 2002;3(11):836-47.
Shamis et al., "Bioactivation of Self-Immolative Dendritic Prodrugs by Catalytic Antibody 38C2," J. Am. Chem. Soc. 2004; 126 (6):1726-1731.
Shan et al., "Selective, covalent modification of β-tubulin residue Cys-239 by T138067, an antitumor agent with in vivo efficacy against multidrug-resistant tumors." Proc. Nat. Acad. Sci. USA May 11, 1999; 96(10):5686-5691.
Shaw et al., "Mouse/Human Chimeric Antibodies to a Tumor-Associated Antigen: Biologic Activity of the Four Human IgG Subclasses." J. Natl. Cancer Inst. Dec. 7, 1988; 80(19):1553-1559.
Shi et al., "Distinct reactivity differences of metal oxo and its corresponding hydroxo moieties in oxidations: implications from a manganese(IV) complex having dihydroxide ligand." Angew Chem Int Ed Engl. Aug. 1, 2011; 50(32):7321-4.
Shirai et al., "Asymmetric synthesis of antimitotic combretadioxolane with potent antitumor activity against multi-drug resistant cells." Bioorg Med Chem Lett. Aug. 4, 1998; 8(15):1997-2000.

(56) References Cited

OTHER PUBLICATIONS

Shirai et al., "Synthesis and nti-tubulin activity of aza-combretastatins." Bioorganic. Med. Chem. Lett. 1994; 4(5):699-704.
Shiraki, S. et al., "Solid-state photochemistry of crystalline pyrazolines: reliable generation and reactivity control of 1,3-biradicals and their potential for the green chemistry sysnthesis of substitutedcyclopropanes," Photochem. Photobiol. Sci. 2012, 11, pp. 1929-1937.
Singh et al., "Antineoplastic agents. 166. Isolation, structure, and synthesis of combretastatin C-1." J. Org. Chem. 1989; 54(17):4105-4114.
Singh et al., Recent trends in targeted anticancer prodrug and conjugate design. Curr Med Chem. 2008;15(18):1802-26.
Slamon et al., "Studies of the HER-2/neu proto-oncogene in human breast and ovarian cancer." Science May 12, 1989; 244(4905):707-712.
Soledade et al., "Minor phytotoxins from the blackleg fungus Phoma lingam." Phytonchem. 1990; 29(3):777-782.
Solladie-Cavallo et al., "A Four-Step Diastereoselective Synthesis of D-erythro-Sphingosine by an Enantioselective Aldol Reaction Using a Titanium Enolate Derived from a Chiral Iminoglycinate." J. Org. Chem. 1994; 59(11):3240-3242.
Solladie-Cavallo et al., "A four-step synthesis of erythro-m-chloro-3-hydroxytyrosine ethyl ester enantiomerically pure." Tetrahedron Lett., 1998; 39(15):2191-2194.
Solladie-Cavallo et al., "Diastereoselective monoalkylation of lithium and potassium enolates of a chiral imine of ethyl glycinate: the role of added salts." Organometallics1993; 12(9):3743-3747.
Solladie-Cavallo et al., "Enantioselective synthesis of optically pure natural S(+) or unnatural R(−) DABA." Tetrahedron Lett. 1989;30(44):6011-6014.
Speth et al., "Gliotoxin as putative virulence factor and immunotherapeutic target in a cell culture model of cerebral aspergillosis." Mol Immunol. Sep. 2011;48(15-16):2122-9.
Springer et al., "The structure of ditryptophenaline—a new metabolite of aspergillusflavus." Tetrahedron Lett. 1977; 18(28):2403-2406.
Stephens, D. E. et al., "Straightforward Access to Hexahydropyrrolo[2,3-b]indole Core by aRegioselective C3-Azo Coupling Reaction of Arenediazonium Compounds with Tryptamines," Eur. J. Org. Chem. 2014, pp. 3662-3670.
Steplewski et al., "Release of Monoclonal Antibody-defined Antigens by Colorectal Carcinoma and Melanoma Cells." Cancer Res. Jul. 1981; 41:2723-2727.
Still et al., "Rapid chromatographic technique for preparative separations with moderate resolution" J. Org. Chem. 1978, 43, 2923.
Storm et al., "Effect of small changes in orientation on reaction rate." J. Am. Chem. Soc. 1972; 94(16):5815-5825.
Stout et al., "Potent Fluorinated Agelastatin Analogues for Chronic Lymphocytic Leukemia: Design, Synthesis, and Pharmacokinetic Studies," J. Med. Chem., 57, p. 5085-5093 (2014).
Strassner et al., Mechanism of Permanganate Oxidation of Alkanes: Hydrogen Abstraction and Oxygen "Rebound" J. Am. Chem. Soc. 2000; 122(32):7821-7822.
Stueber et al, "Carbonates, Thiocarbonates, and the Corresponding Monoalkyl Derivatives. 1. Their Preparation and Isotropic 13C NMR Chemical Shifts." Inorg. Chem. 2001; 40(8):1902-1911.
Sumiyoshi, T. et al., "Laser Flash Photolysis of Azocumenes. Direct Observation of StepwiseDecomposition," Bull. Chem. Soc. Jpn. 1987, 60, pp. 77-81.
Sugiyama et al., "Syntheses of four unusual amino acids, constituents of cyclomarin A." Tetrahedron Lett. 2002: 43(19):3489-2492.
Sun et al., "Chimeric Antibody with Human Constant Regions and Mouse Variable Regions Directed Against Carcinoma-Associated Antigen 17-1A." Proc. Natl. Acad. Sci., USA Jan. 1987; 84:214-218.
Sun et al., "Enabling ScFvs as multi-drug carriers: A dendritic approach," Bioorganic & Medicinal Chemistry Letters 2003; 11:1761-1768.

Sun et al., "Syntheses of Dendritic Linkers Containing Chlorambucil Residues for the Preparation of Antibody-Multidrug Immunoconjugates," Bioorganic & Medicinal Chemistry Letters 2002; 12:2213-2215.
Sun et al., Construction of 3-oxyindoles via hypervalent iodine mediated tandem cyclization-acctoxylation of o-acyl anilines. Chem Commun. 2010;46(36):6834-6.
Suresh et al., "Bispecific monoclonal antibodies from hybrid hybridomas." Methods Enzymol. 1986;121:210-28.
Szalai et al., "Geometric disassembly of dendrimers: dendritic amplification." J Am Chem Soc. Dec. 24, 2003;125(51):15688-9.
Tahir et al., "Secreted Caveolin-1 Stimulates Cell Survival/Clonal Growth and Contributes to Metastasis in Androgen-insensitive Prostate Cancer." Cancer Res. 2001; 61(10):3882-3885.
Takahashi et al., "Inhibition of histone H3K9 methyltransferases by gliotoxin and related epipolythiodioxopiperazines." J Antibiot (Tokyo). May 2012;65(5):263-5.
Teng et al., "Construction and testing of mouse—human heteromyelomas for human monoclonal antibody production." Proc Natl Acad Sci U S A. Dec. 1983; 80(23): 7308-7312.
Teng et al., "Unnatural enantiomer of chaetocin shows strong apoptosis-inducing activity through caspase-8/caspase-3 activation." Bioorg. Med. Chem. Lett. 2010; 20(17):5085-5088.
Teniou et al., "(+)(1R,2R,5R) 2-Hydroxy-3-pinanone as Chiral Auxiliary in Erythro-selective Aldol Reactions." Asian J Chem. 2006; 18:2487-2490.
Tibodeau et al., "The anticancer agent chaetocin is a competitive substrate and inhibitor of thioredoxin reductase." Antioxid Redox Signal. May 2009; 11(5):1097-106.
Toki et al., "Protease-Mediated Fragmentation of p-Amidobenzyl Ethers: A New Strategy for the Activation of Anticancer Prodrugs." J. Org. Chem. 2002; 67(6):1866-1872.
Trail et al., "Cure of xenografted human carcinomas by BR96-doxorubicin immunoconjugates." Science Jul. 9, 1993; 261(5118):212-215.
Trail et al., "Effect of Linker Variation on the Stability, Potency, and Efficacy of Carcinoma-reactive BR64-Doxornbicin Immunoconjugates." Cancer Research 1997; 57:100-105.
Traunecker et al., "Bispecific single chain molecules (Janusins) target cytotoxic lymphocytes on HIV infected cells." EMBO J. Dec. 1991; 10(12): 3655-3659.
Trown, P.W, "Antiviral activity of N, N'-dimethyl-epidithiapiperazinedione, a synthetic compound related to the gliotoxins, LL-S88alpha and beta, chetomin and the sporidesmins." Biochem Biophys Res Commun. Nov. 8, 1968;33(3):402-7.
Tsuji, T. et al., "Diazenes. VI. Alkyldizenes," Journal of the American Chemical Society 1971, 93(8), pp. 1992-1999.
Uckun et al., "Structure-based design of a novel synthetic spiroketal pyran as a pharmacophore for the marine natural product spongistatin 1." Bioorg Med Chem Lett. Mar. 20, 2000; 10(6):541-5.
Usami et al., "Gliocladins A—C and Glioperazine ; Cytotoxic Dioxo- or Trioxopiperazine Metabolites from a *Gliocladium* Sp. Separated from a Sea Hare." Heterocycles 2004; 63(5):2004:1123-1129.
Varki et al., "Antigens associated with a human lung adenocarcinoma defined by monoclonal antibodies." Cancer Res. Feb. 1984;44(2):681-7.
Verdier-Pinard et al., "A Steroid Derivative with Paclitaxel-Like Effects on Tubulin Polymerization." Molecular Pharmacology Mar. 2000: 57(3):568-575.
Verdier-Pinard et al., "Biosynthesis of radiolabeled curacin A and its rapid and apparently irreversible binding to the colchicine site of tubulin." Arch Biochem Biophys. Oct. 1, 1999; 370(1):51-8.
Verhoeyan et al., "Reshaping human antibodies: grafting an antilysozyme activity." Science Mar. 25, 1988; 239(4847):1534-1536.
Verott A, L. et al., "Pyrrolidinoindoline Alkaloids from Psychotria colorata," J. Nat. Prod. 1998, 61, pp. 392-396.
Verott A, L. et al., "Synthesis and Antinociceptive Activity of Chimonanthines and Pyrrolidinoindoline-Type Alkaloids," Bioorganic & Medicinal Chemistry 2002, 10, pp. 2133-2142.
Vichai et al., "Sulforhodamine B colorimetric assay for cytotoxicity screening." Nat Protoc. 2006; 1(3):1112-6.

(56) References Cited

OTHER PUBLICATIONS

Vingushin et al., "Gliotoxin is a dual inhibitor of farnesyltransferase and geranylgeranyltransferase I with antitumor activity against breast cancer in vivo." Med Oncol. 2004;21(1):21-30.
Wahl et al., "The anti-CD30 monoclonal antibody SGN-30 promotes growth arrest and DNA fragmentation in vitro and affects antitumor activity in models of Hodgkin's disease." Cancer Res. Jul. 1, 2002; 62(13):3736-42.
Walker et al., "A High Yielding Synthesis of N-Alkyl Maleimides Using a Novel Modification of the Mitsunobu Reaction." J. Org. Chem., 1995; 60(16):5352-5355.
Wang et al., "Potent, Orally Active Heterocycle-Based Combretastatin A-4 Analogues: Synthesis, Structure-Activity Relationship, Pharmacokinetics, and In Vivo Antitumor Activity Evaluation." J. Med. Chem. 2002; 45(8):1697-1711.
Wang et al., "Synthesis of B-ring homologated estradiol analogues that modulate tubulin polymerization and microtubule stability." J Med Chem. Jun. 15, 2000; 43(12):2419-29.
Wantanabe et al., Reaction of 1-Acyl and Aroyl-2-hydroxy-3,3-dimethylindolines with Arylamines Catalyzed by BF3•Etherate. Formation of Dihydroindolo[1,2-c]quinazoline. Heterocycles. 2007;71(2):343-59.
Ward et al., "Binding activities of a repertoire of single immunoglobulin variable domains secreted from *Escherichia coli*." Nature. Oct. 12, 1989;341(6242):544-6.
Waring et al., "Gliotoxin and related epipolythiodioxopiperazines." Gen Pharmacol. Dec. 1996;27(8):1311-6.
Waring et al., "The chemistry and biology of the immunomodulating agent gliotoxin and related epipolythiodioxopiperazines." Med Res Rev. Oct.-Dec. 1988;8(4):499-524.
Wen et al., "Synthesis of a fully protected (2S,3R)-N-(1',1'-dimethyl-2'-propenyl)-3-hydroxytryptophan from tryptophan." Tetrahedron Lett. 2002: 43(30):5291-5294.
Wen et al., "Total Synthesis of Cyclomarin C." Org. Lett. 2004; 6(16):2721-2724.
Wender, P. A. et al., "Practical Synthesis of Prostratin, OPP, and Their Analogs, Adjuvant Leads Against Latent HIV," Science May 8, 2008, 320(5876), pp. 649-652.
Wenkert et al., "Five-membered aromatic heterocycles as dienophiles in Diels-Alder reactions. Furan, pyrrole, and indole." J. Am. Chem. Soc. 1988; 110(21):7188-7194.
White, K. L. et al., "Concise Total Syntheses of (+)-Haplocidine and (+)-Haplocine via Late-StageOxidation of ( +)-Fendleridine Derivatives," J. Am. Chem. Soc. 2016, 138(35), pp. 11383-11389.
Williams et al., "Divergent, generalized synthesis of unsymmetrically substituted 2,5-piperazinediones." J. Am. Chem. Soc. 1985; 107(11):3246-3253.
Williams et al., "Syntheses of the fungal metabolites (.+−.)-gliovictin and (.+−.)-hyalodendrin." J. Org. Chem. 1980; 45(13):2625-2631.
Wood et al., "The interaction with tubulin of a series of stilbenes based on combretastatin A-4." Br J Cancer. Apr. 1995; 71(4):705-11.
Wood et al., "The synthesis and in vivo assembly of functional antibodies in yeast." Nature 1985; 314:446-449.
Wu-Wong et al., "Identification and Characterization of A-105972, an Antineoplastic Agent." Cancer Res. 2001; 61:1486-1492.
Xu, L. et al., "Iridium(III)-Catalyzed Regioselective C7-Amination of N-Pivaloylindoles with Sulfonoazides," J. Org. Chem. 2016, 81, pp. 10476-10483.
Yanagihara et al., "Leptosins isolated from marine fungus *Leptoshaeria* species inhibit DNA topoisomerases I and/or II and induce apoptosis by inactivation of Akt/protein kinase B." Cancer Sci. Nov. 2005;96(11):816-24.
Yano et al., "Chetomin induces degradation of XIAP and enhances TRAIL sensitivity in urogenital cancer cells." Int J Oncol. Feb. 2011;38(2):365-74.
Yu et al., A General Strategy for the Synthesis of Vincamajine-Related Indole Alkaloids: Stereocontrolled Total Synthesis of (+)-Dehydrovoachalotine, (−)-Vincamajinine, and (−)-11-Methoxy-17-epivincamajine as Well as the Related Quebrachidine Diol, Vincamajine Diol, and Vincarinoll. J Org Chem. Apr. 19, 2005;70(10):3963-79.
Yu et al., Stereocontrolled Total Synthesis of (−)-Vincamajinine and (−)-11-Methoxy-17-epivincamajine. J Am Chem Soc. Jan. 21, 2004;126(5):1358-9.
Zalatan, D. N. et al., "Metal-Catalyzed Oxidations of C—H to C—N Bonds," Top. Curr. Chem. 2010, 292, pp. 347-378.
Zalatan, D. N. et al., "Understanding the Differential Performance of Rh2(esp)2 as a Catalyst for C—H Amination," J. Am. Chem. Soc. 2009, 131, pp. 7558-7559.
Zhang et al., "Microtubule effects of welwistatin, a cyanobacterial indolinone that circumvents multiple drug resistance." Molecular Pharmacology Feb. 1996; 49(2):288-294.
Zhang et al., "PARP and RIP 1 are required for autophagy induced by 11'-deoxyverticillin A, which precedes caspase-dependent apoptosis." Autophagy. Jun. 2011;7(6):598-612.
Zheng et al., "Bionectins A—C, Epidithiodioxopiperazines with Anti-MRSA Activity, from Bionectra byssicola F120," J. Nat. Prod., 2006, 69 (12), pp. 1816-1819.
Zhu et al., Aptamer-Drug Conjugates. Bioconjug Chem. Nov. 18, 2015;26(11):2186-97. doi: 10.1021/acs.bioconjchem.5b00291. Epub Jul. 14, 2015.
U.S. Appl. No. 16/612,468, filed Nov. 11, 2019, Movassaghi et al.
PCT/US2013/073062, May 20, 2014, International Search Report and Written Opinion.
PCT/US2013/073062, Jun. 9, 2015, International Preliminary Report on Patentability.
PCT/US2014/056263, Dec. 4, 2014, International Search Report and Written Opinion.
PCT/US2014/056263, May 22, 2016, International Preliminary Report on Patentability.
PCT/US2014/034327, Sep. 1, 2017, International Search Report and Written Opinion.
PCT/US2014/034327, Dec. 6, 2018, International Preliminary Report on Patentability.
PCT/US2018/032327, Jul. 23, 2018, Invitation to Pay Additional Fees.
PCT/US2018/032327, Sep. 21, 2018, International Search Report and Written Opinion.
PCT/US2018/032327, Nov. 21, 2019, International Preliminary Report on Patentability.
Belmar et al., Total synthesis of (±)-communesin F via a cycloaddition with indol-2-one. J Am Chem Soc. Oct. 17, 2012;134(41):16941-3. doi:10.1021/ja307277w. Epub Sep. 28, 2012.
Li et al., Pharmacokinetics of Agelastatin A in the central nervous system. Med. Chem. Commun. 2012;3:233-237.
Li et al., Cytotoxic metabolites from the antarctic psychrophilic fungus Oidiodendron truncatum. J Nat Prod. May 25, 2012;75(5):920-7. doi: 10.1021/np3000443. Epub May 14, 2012.
Lin et al., Elucidation of the concise biosynthetic pathway of the communesin indole alkaloids. Angew Chem Int Ed Engl. Mar. 2, 2015;54(10):3004-7. doi: 10.1002/anie.201411297. Epub Jan. 8, 2015.
Lin et al., P450-Mediated Coupling of Indole Fragments to Forge Communesin and Unnatural Isomers. J Am Chem Soc. Mar. 30, 2016;138(12):4002-5. doi: 10.1021/jacs.6b01413. Epub Mar. 18, 2016.
Shin et al., Transition-Metal-Catalyzed C—N Bond Forming Reactions Using Organic Azides as the Nitrogen Source: A Journey for the Mild and Versatile C—H Amination. Acc. Chem. Res. 2015;48:1040-1052.
Shiraki et al., The synthesis and stereospecific solid-state photodecarbonylation of hexasubstituted mesa- and d,/-ketones. Photochem. Photobiol. Sci. 2011;10:1480-1487.
Snell et al., Catalytic Enantioselective Total Synthesis of Hodgkinsine B. Angew. Chem. Int. Ed. 2011;50:9116-9119.
Somei et al., Preparations of melatonin and 1-hydroxymelatonin, and its novel nucleophilicdimerization to (±)-3a,3a'-bispyrrolo[2,3-b]indoles. Heterocycles. 1999;51(6):1237-1242.
Steininger, Synthesis of 5-Chloromethyl-2,dinitrotetrahydrofuran. Angew. Chem. Internat. Edit.1965;4(5):433.
Tadano et al., Bio-Inspired Dimerization Reaction of Tryptophan Derivatives in Aqueous AcidicMedia: Three-Step Syntheses of

(56) References Cited

OTHER PUBLICATIONS (+)-WIN 64821, (−)-Ditryptophenaline, and (+)-Naseseazine B. Angew. Chem. Int. Ed. 2013;52:7990-7994.
Timberlake et al., Thiadiaziridine 1, 1-Dioxides: Synthesis and Chemistry. J. Org. Chem. 1981;46:2082-2089.
Zuo et al., Enantioselective total syntheses of communesins A and B. Angew Chem Int Ed Engl. Dec. 9, 2011;50(50):12008-11. doi: 10.1002/anie.201106205. Epub Oct. 18, 2011.

\* cited by examiner (−)-communesin F (1)

CONVERGENT AND ENANTIOSELECTIVE TOTAL SYNTHESIS OF COMMUNESIN ANALOGS

CROSS-REFERENCE TO RELATED APPLICATION

This application claims the benefit of and priority to U.S. Provisional Application No. 62/334,826, filed on May 11, 2016 and entitled "CONVERGENT AND BIOMIMETIC ENANTIOSELECTIVE TOTAL SYNTHESIS OF (−)-COMMUNESIN F," the disclosure of which is hereby incorporated by reference in its entirety for all purposes.

STATEMENT OF GOVERNMENT INTEREST

This invention was made with government support under Grant No. R01 GM089732 awarded by the National Institutes of Health, and under Grant No. CHE-1212527 awarded by the National Science Foundation. The government has certain rights in the invention.

BACKGROUND

The communesin alkaloids are a family of nine structurally complex natural products isolated from various marine and terrestrial *Penicillium* fungi (FIG. 1). Some members have been shown to possess insecticidal and antiproliferative activities as well as significant cytotoxicity against lymphocytic leukemia. Communesins A (2) and B (4), first isolated in 1993 by Numata were found to exhibit moderate to potent cytotoxicity against cultured mouse P-388 lymphocytic leukemia cells ($ED_{50}$=3.5 µg/mL and 0.45 µg/mL, respectively). (Numata, A.; Takahashi, C.; Ito, Y.; Takada, T.; Kawai, K.; Usami, Y.; Imachi, M.; Ito, T.; Hasegawa, T. *Tetrahedron Lett.* 1993, 34, 2355-2358.) In 2004, Jadulco and co-workers isolated communesins C (5) and D (6) and, together with 4, were shown to possess moderate antiproliferative activity against an array of human leukemia cell lines (Table 1). Furthermore, compounds 4, 5 and 6 exhibited toxicity against the brine shrimp *Artemia salina* with $LD_{50}$ values of 0.30, 1.96, and 0.57 µg/mL, respectively. (Jadulco, R.; Edrada, R. A.; Ebel, R.; Berg, A.; Schaumann, K.; Wray, V.; Steube, K.; Proksch, P. *J. Nat. Prod.* 2004, 67, 78-81.)

Later in 2004, Hayashi and co-workers isolated communesins E (3) and F (1) and studied the insecticidal properties of these new derivatives together with 2, 4, and 6. (Hayashi, H.; Matsumoto, H.; Akiyama, K. *Biosci. Biotechnol. Biochem.* 2004, 68, 753-756.) Communesin B (4) was found to be the most active against third instar larvae of silkworms with an $LD_{50}$ value of 5 µg/g of diet by oral administration. Communesins A (2), D (6), E (3), and F (1) were found to exhibit lower insecticidal activities.

Recently, in 2015, Fan and co-workers isolated communesin I (9) and studied the cardiovascular effects of this new alkaloid, together with co-isolates 2 and 4. (Fan, Y.-Q.; Li, P.-H.; Chao, Y.-X.; Chen, H.; Du, N.; He, Q.-X.; Liu, K.-C. *Mar. Drugs.* 2015, 13, 6489-6504.) All three compounds showed a significant mitigative effect on bradycardia caused by astemidazole at different concentrations. In addition, communesins I (9) and A (2) exhibited moderate vasculogenetic activity. Finally, compounds 9 and 2 were found to moderately promote the function of cardiovascular vessels.

The core structures of the communesins share a unique heptacyclic skeleton containing two aminals and at least five stereogenic centers, of which two are vicinal and quaternary (FIG. 1). To date, the total synthesis of (±)-communesin F (1) has been completed by Qin, Weinreb, and Funk, in addition to a formal synthesis by Stoltz. Ma's total synthesis of (−)-communesin F (1) remains the only enantioselective solution for this archetypical alkaloid. However, these total syntheses are complex, low yielding, and do not readily lend themselves to the synthesis of analogs or derivatives of (−)-1, which would be necessary to support a rational drug development program.

The exquisite structural complexity, coupled with an array of interesting biological properties has prompted the present disclosure of a novel, efficient, and convergent chemical synthesis of the communesin alkaloids. These methods involve the stereocontrolled oxidative union of two dissimilar tryptamine derivatives followed by reorganization of a C3a-C3a' linked heterodimer to develop a highly convergent total synthesis that would be suitable for the preparation of diverse analogs derived from the family of communesins.

Herein, are presented concise enantioselective total syntheses of several representative communesins, ready for adaption toward a wide range of previously unexplored analogs. The highly convergent route establishes inventive methods that allow for unprecedented efficiency in constructing the complex heptacyclic ring system from two densely functionalized building blocks. In addition, the use of flexible stereochemical control elements enables access to any selected enantiomer or diastereomer without dramatic alterations to the strategy, and is easily generalized and applied to the synthesis of a wide variety of analogs. This novel chemical synthesis allows, for the first time, the opportunity to fully explore the promising biological properties of this class of compounds.

BRIEF SUMMARY

Various inventive embodiments are disclosed that are generally directed to a highly convergent biomimetic enantioselective synthesis of alkaloid compounds of Formula (I), as well as compounds and methods of use of Formula (I), as described herein.

In one embodiment, the present disclosure relates to compounds of Formula (I):

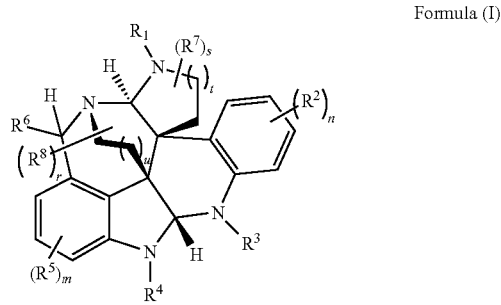

Formula (I)

or a pharmaceutically acceptable salt, tautomer or stereoisomer thereof is described, wherein:

$R^1$, $R^3$, and $R^4$ are each independently selected from H, $C_1$-$C_{12}$ alkyl, $C_2$-$C_{12}$ alkenyl, $C_2$-$C_{12}$ alkynyl, —C(=O)$R^9$, —C(=O)N$R^9R^{10}$, —S(=O)$_u R^{12}$, aryl, heteroaryl, carbocyclyl, or heterocyclyl, wherein $R^3$ and $R^4$ taken together with the carbon atoms to which they are attached form an aryl, heteroaryl, carbocyclic, or heterocyclic ring;

$R^2$ and $R^5$ are each independently selected from F, Cl, Br, I, —OH, —O$R^9$, —OC(=O)$R^9$, —S(=O)$R^{12}$, —N$R^9R^{10}$, $C_1$-$C_{12}$ alkyl, $C_2$-$C_{12}$ alkenyl, $C_2$-$C_{12}$ alkynyl, aryl, heteroaryl, carbocyclyl, or heterocyclyl;

$R^6$ is independently H, —OH, —OR$^9$, —OC(=O)R$^9$, —S(=O)R$^{12}$, —NR$^9$R$^{10}$, $C_1$-$C_{12}$ alkyl, $C_1$-$C_{12}$ alkyl, $C_2$-$C_{12}$ alkenyl, $C_2$-$C_{12}$ alkynyl aryl, heteroaryl, carbocyclyl, or heterocyclyl;

$R^7$ and $R^8$ are each independently selected from H, $C_1$-$C_{12}$ alkyl; $C_2$-$C_{12}$ alkenyl, $C_2$-$C_{12}$ alkynyl, —C(=O)R$^9$, —C(=O)NR$^9$R$^{10}$, —S(=O)$_u$R$^{12}$, —OH, —OR$^9$, —OC(=O)R$^9$, —NR$^9$R$^{10}$, aryl, heteroaryl, carbocyclyl, or heterocyclyl, wherein two $R^7$ or two $R^8$ groups taken together with the carbon atoms to which they are attached form an aryl, heteroaryl, carbocyclic, or heterocyclic ring;

$R^9$ and $R^{10}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^9$ and $R^{10}$ taken together with the carbon atoms to which they are attached form an aryl, heteroaryl, carbocyclic, or heterocyclic ring;

$R^{12}$ is $C_1$-$C_{12}$ alkyl, $C_2$-$C_{12}$ alkenyl, $C_2$-$C_{12}$ alkynyl, aryl, heteroaryl, carbocyclyl, heterocyclyl, —(CH$_2$)$_n$SiMe$_3$, or —(CH$_2$)$_n$R$_9$.

m and t are each independently an integer from 0 to 3;
n, r, s, and v are each independently an integer from 0 to 4; and
u is 0, 1, or 2;
with the following provisos:
when $R^1$ is

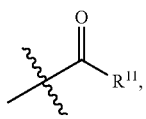

wherein $R^{11}$ is Me, Et, n-Pr,

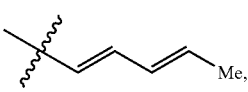 [SMILES: */C=C/C=C/C]

or

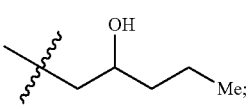 [SMILES: *CC(O)CCC]

$R^4$ is Me;
m, n, r, and s are 0;
t and u are 1; then
$R^6$ is not

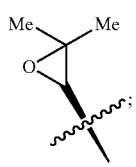

and
when $R^1$ is

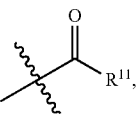

wherein $R^{11}$ is Me;
$R^4$ is Me;
m, n, r, and s are 0;
t and u are 1; then
$R^6$ is not

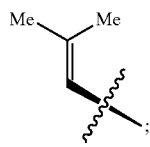

and
when $R^1$ is

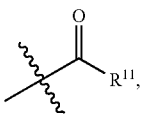

wherein $R^{11}$ is Me, or

$R_4$ is H;
m, n, r, and s are 0;
t and u are 1; then
$R^6$ is not

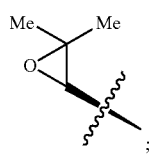

and
when $R^1$ is

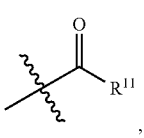

wherein $R^{11}$ is

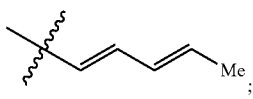

$R^4$ is —CHO;
m, n, r, and s are 0;
t and u are 1; and
$R_6$ is not

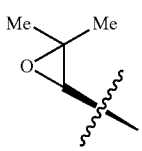

In one embodiment, the present disclosure relates to a pharmaceutical composition comprising a compound of Formula (I) and a pharmaceutically acceptable excipient.

In another embodiment, the present disclosure provides a method of treating a disease or condition comprising administering an effective amount of the pharmaceutical composition to a subject. In some embodiments, the disease or condition is cancer. In other embodiments, the disease or condition is a bacterial infection. In other embodiments, the disease or condition is a fungal infection. In another embodiment, the disease or condition is a viral infection. In still other embodiments, the disease or condition is abnormal cardiovascular function. In yet another embodiment, the pharmaceutical compositions are used to treat insect infestations.

In one embodiment, the disclosure provides a method of making compounds of Formula (I) by a rearrangement of:

Formula (V)

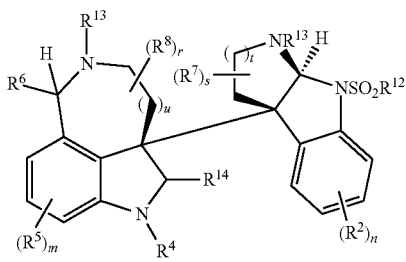

In another embodiment, the present disclosure provides a method of making compounds of Formula (V) by a radical recombination reaction of, e.g., by photochemical degradation of the azo group:

Formula (VI)

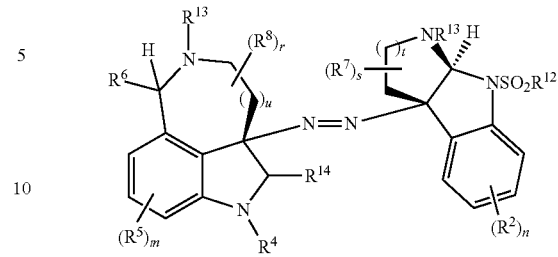

In another embodiment, the present disclosure provides a method of making compounds of Formula (VI) by the extrusion of sulfur dioxide from:

Formula (VII)

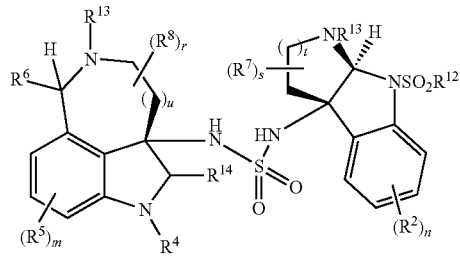

In still another embodiment, the present disclosure provides a method of making compounds of Formula (VII) by a reaction (e.g., nucleophilic substitution reaction) between compounds of Formula (III) and Formula (VIII):

Formula (III)

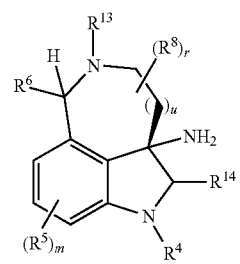

Formula (VIII)

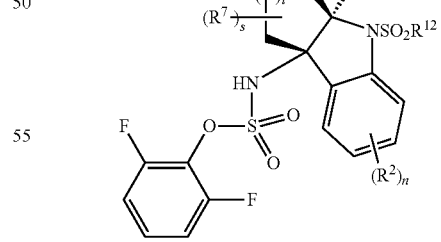

In one embodiment, the first biomimetic enantioselective total synthesis of (−)-communesin F based on a late-stage heterodimerization and aminal exchange is described. It is to be understood that these methods and approaches can be generalized and applied to the synthesis of a variety of compounds, including various communesin derivatives, such as those represented by Formula (I).

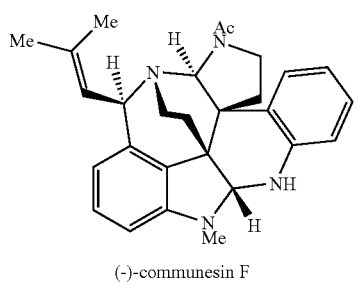

(−)-communesin F

BRIEF DESCRIPTION OF THE FIGURES

The skilled artisan will understand that the drawings primarily are for illustrative purposes and are not intended to limit the scope of the inventive subject matter described herein.

DETAILED DESCRIPTION

Figure 1:
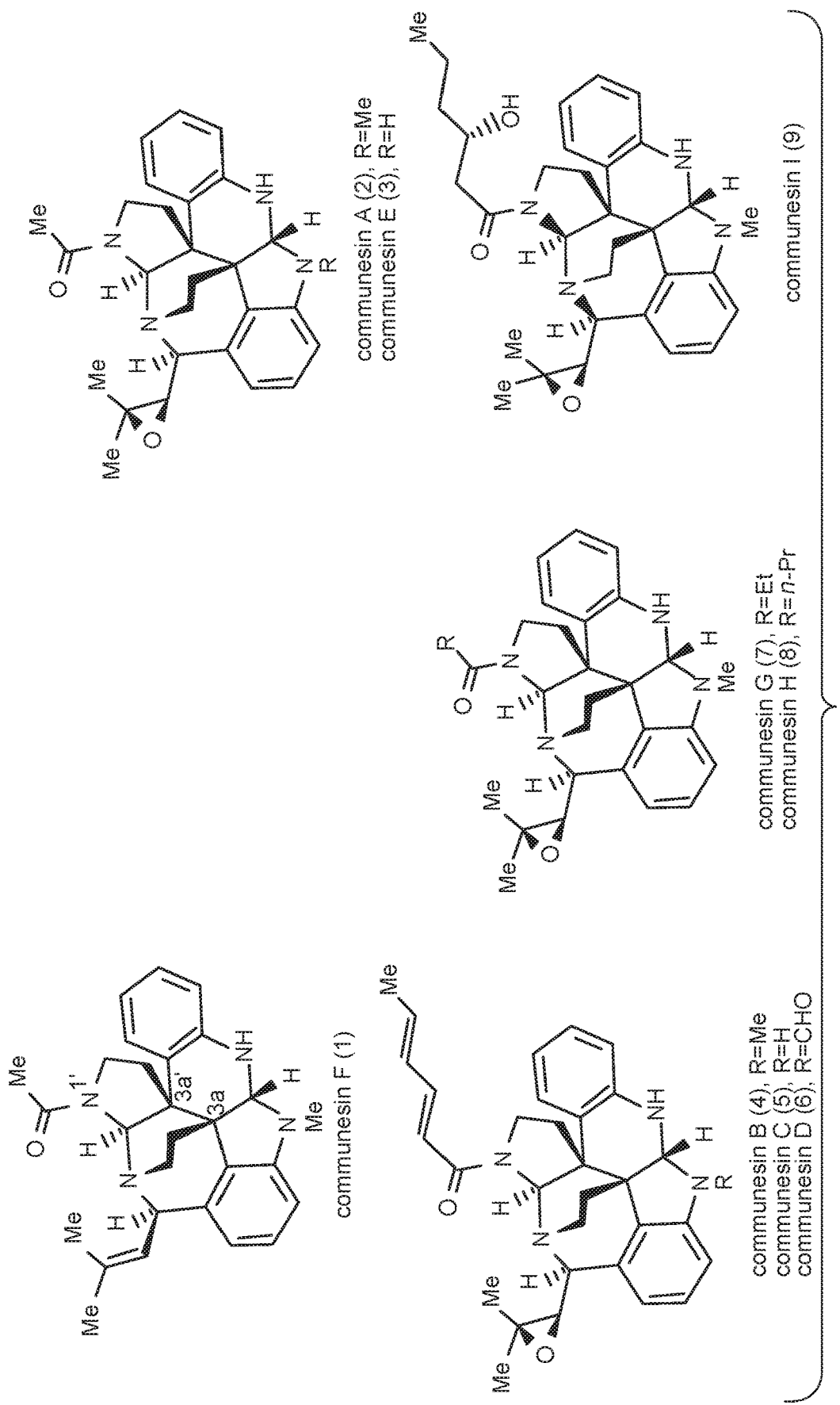
FIG. 1 shows the chemical structures of the naturally occurring communesin alkaloids.
Figure 2:
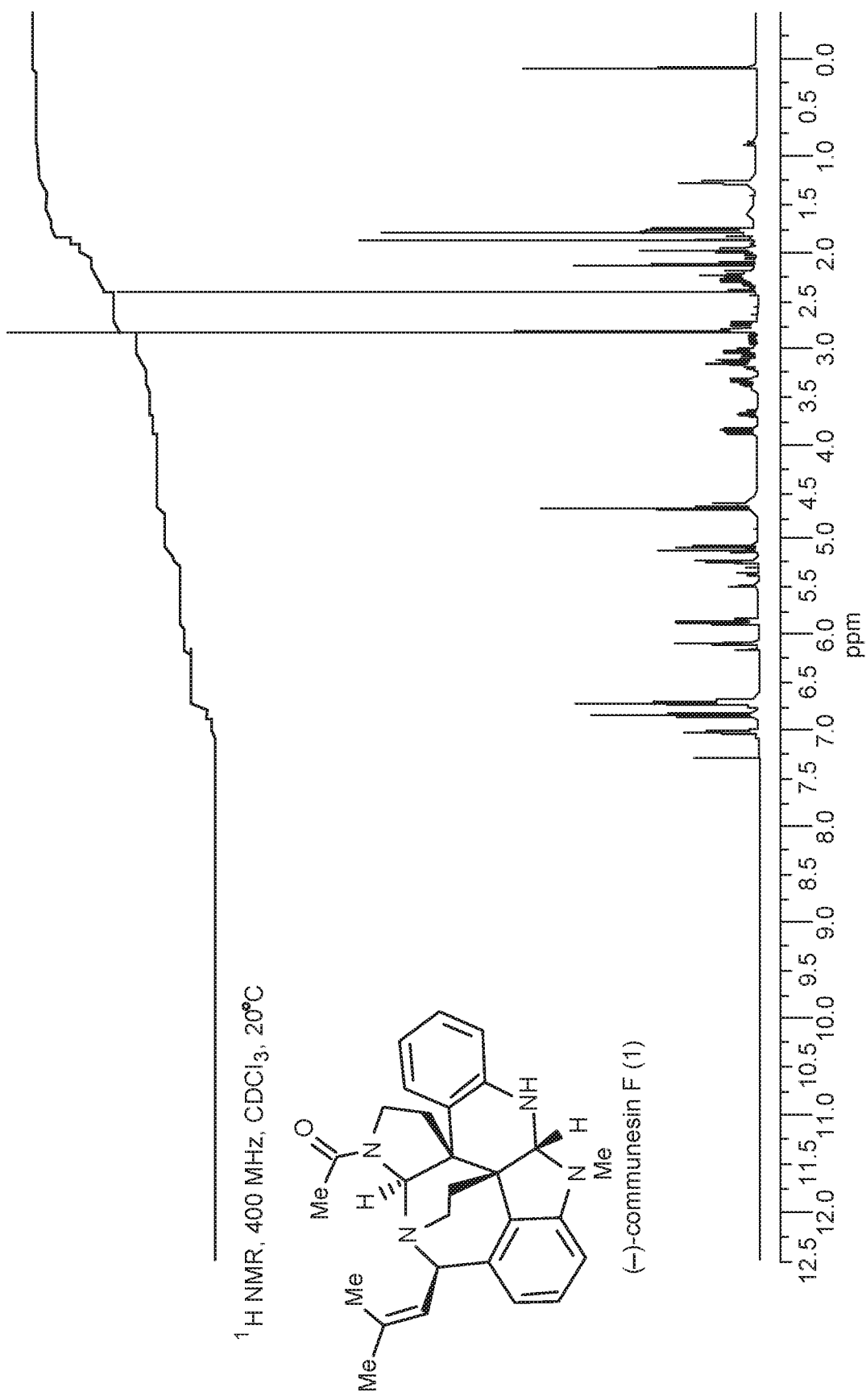
FIG. 2 is a $^1$H NMR spectrum for (−)-communesin F prepared by the methods described herein.
Figure 3:
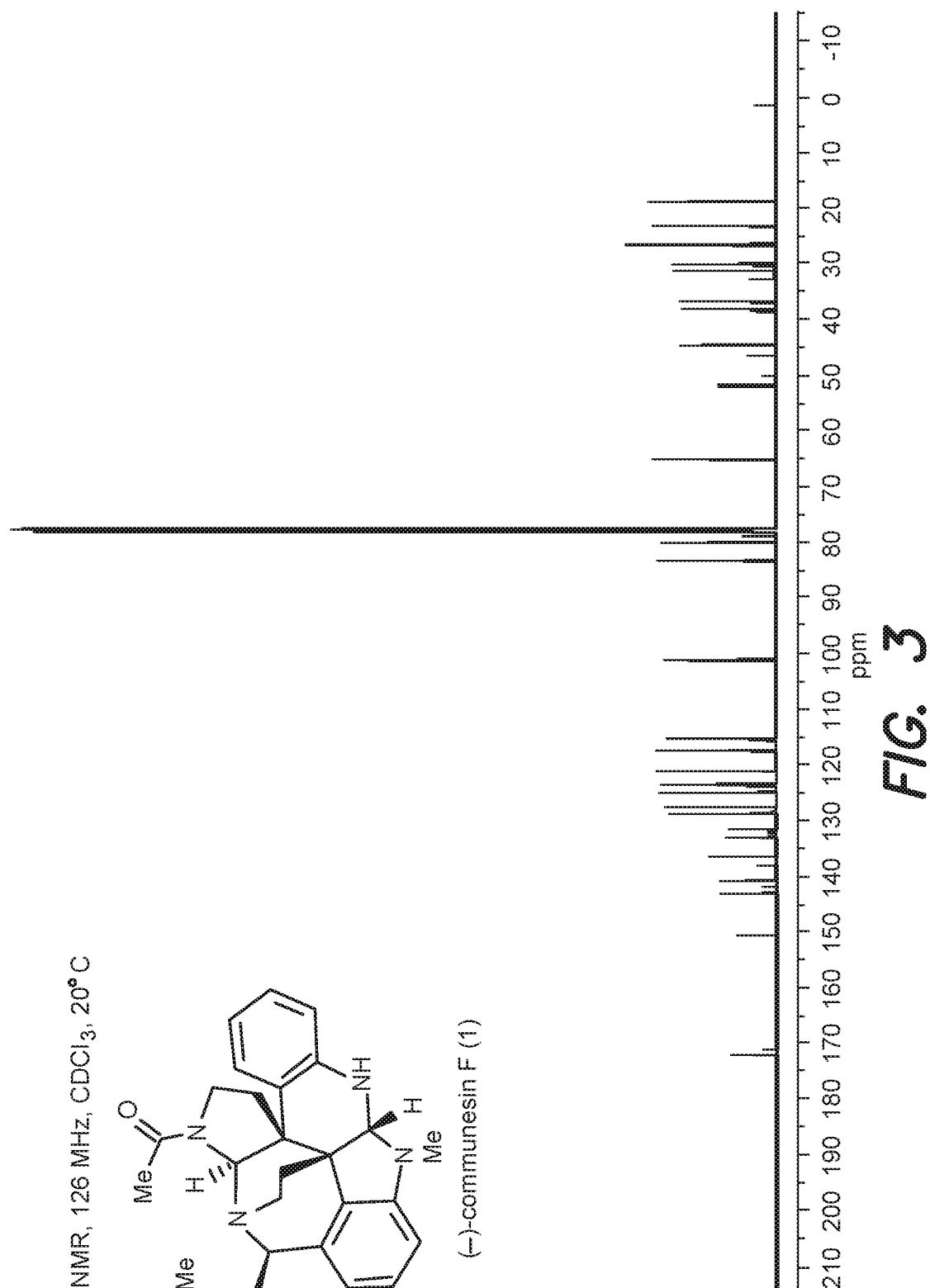
FIG. 3 is a $^{13}$C NMR spectrum for (−)-communesin F prepared by the methods described herein.
Figure 4:
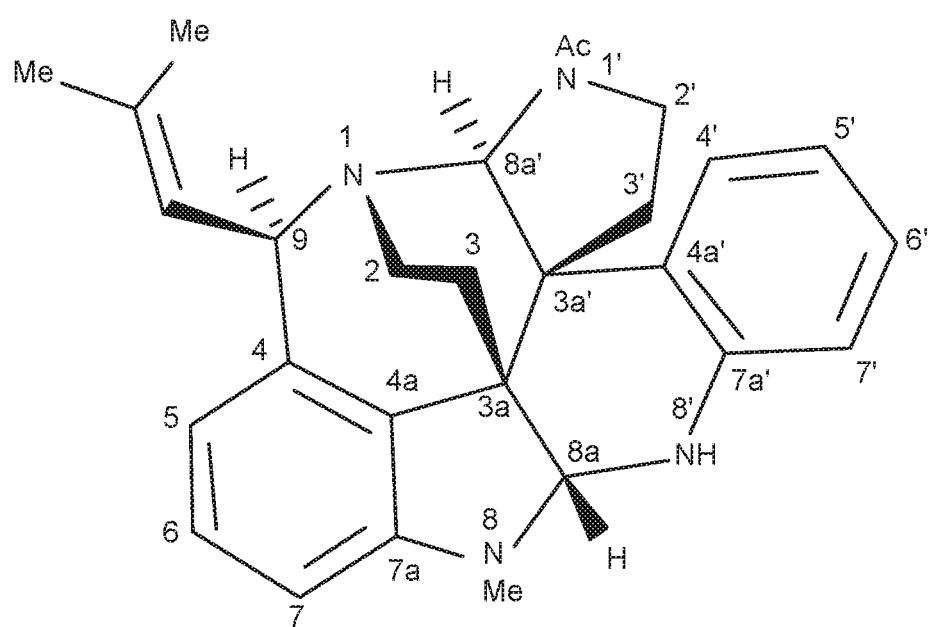
FIG. 4 shows the positional numbering system used for the (−)-communesin F core.
Figure 5:
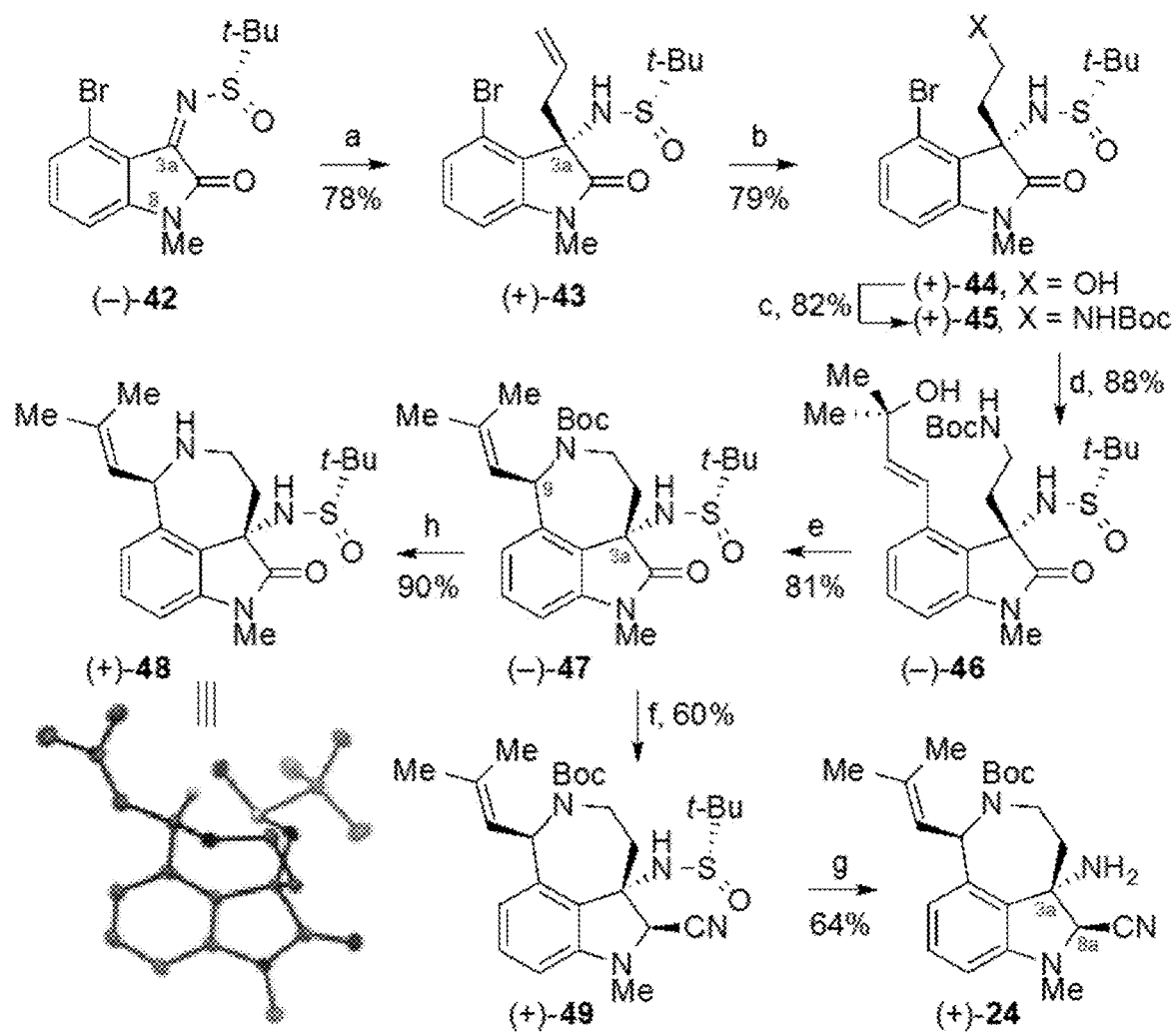
FIG. 5 shows Scheme 8 depicting Sulfinimine Allylation Approach to Tricycle (+)-24$^a$. $^a$Reagents and conditions: (a) allylMgBr, MgBr$_2$, CH$_2$Cl$_2$, −78° C., >98:2 dr; (b) O$_3$, MeOH, −78° C.; NaBH$_4$, −78→23° C.; (c) o-NsNHBoc, diisopropyl azodicarboxylate, polystyrene-PPh$_3$, THF, 50° C.; PhSH, Cs$_2$CO$_3$, 50° C.; (d) Me$_2$C(OH)CH═CHSn(n-Bu)$_3$, PdCl$_2$(PPh$_3$)$_2$, PhMe, THF, 110° C.; (e) PdCl$_2$(MeCN)$_2$, MeCN, 80° C.; (f) (i) LiBH$_4$, MeOH, THF, 0→23° C.; (ii) Me$_3$SiCN, (F$_3$C)$_2$CHOH, 0° C.; (g) HCl, dioxane, MeOH, 23° C.; (h) Sc(OTf)$_3$, F$_3$CCH$_2$OH, 23° C.; o-Ns=ortho-nitrobenzenesulfonyl. ORTEP representation of amine (+)-48: thermal ellipsoids drawn at 50% probability.

In the following description, certain specific details are set forth in order to provide a thorough understanding of various embodiments. However, one skilled in the art will understand that the invention can be practiced without these details. In other instances, well-known structures have not been shown or described in detail to avoid unnecessarily obscuring descriptions of the embodiments.

All definitions, as defined and used herein, should be understood to control over dictionary definitions, definitions in documents incorporated by reference, and/or ordinary meanings of the defined terms. Use of flow diagrams is not meant to be limiting with respect to the order of operations performed for all embodiments. The indefinite articles "a" and "an," as used herein in the specification and in the claims, unless clearly indicated to the contrary, should be understood to mean "at least one."

Reference throughout this specification to "one embodiment" or "an embodiment," etc. means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

"Alkyl" or "alkyl group" refers to a fully saturated, straight or branched hydrocarbon chain radical, and which is attached to the rest of the molecule by a single bond. Alkyls comprising any number of carbon atoms from 1 to 12 are included. An alkyl comprising up to 12 carbon atoms is a $C_1$-$C_{12}$ alkyl, an alkyl comprising up to 10 carbon atoms is a $C_1$-$C_{10}$ alkyl, an alkyl comprising up to 6 carbon atoms is a $C_1$-$C_6$ alkyl and an alkyl comprising up to 5 carbon atoms is a $C_1$-$C_5$ alkyl. A $C_1$-$C_5$ alkyl includes $C_5$ alkyls, $C_4$ alkyls, $C_3$ alkyls, $C_2$ alkyls and $C_1$ alkyl (i.e., methyl). A $C_1$-$C_6$ alkyl includes all moieties described above for $C_1$-$C_5$ alkyls but also includes $C_6$ alkyls. A $C_1$-$C_{10}$ alkyl includes all moieties described above for $C_1$-$C_5$ alkyls and $C_1$-$C_6$ alkyls, but also includes $C_7$, $C_8$, $C_9$ and $C_{10}$ alkyls. Similarly, a $C_1$-$C_{12}$ alkyl includes all the foregoing moieties, but also includes $C_{11}$ and $C_{12}$ alkyls. Non-limiting examples of $C_1$-$C_{12}$ alkyl include methyl, ethyl, n-propyl, i-propyl, sec-propyl, n-butyl, i-butyl, sec-butyl, t-butyl, n-pentyl, t-amyl, n-hexyl, n-heptyl, n-octyl, n-nonyl, n-decyl, n-undecyl, and n-dodecyl. Unless stated otherwise specifically in the specification, an alkyl group can be optionally substituted.

"Alkylene" or "alkylene chain" refers to a fully saturated, straight or branched divalent hydrocarbon chain radical. Alkylenes comprising any number of carbon atoms from 1 to 12 are included. Non-limiting examples of $C_1$-$C_{12}$ alkylene include methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain can be optionally substituted.

"Alkenyl" or "alkenyl group" refers to a straight or branched hydrocarbon chain radical having from two to twelve carbon atoms, and having one or more carbon-carbon double bonds. Each alkenyl group is attached to the rest of the molecule by a single bond. Alkenyl group comprising any number of carbon atoms from 2 to 12 are included. An alkenyl group comprising up to 12 carbon atoms is a $C_2$-$C_{12}$ alkenyl, an alkenyl comprising up to 10 carbon atoms is a $C_2$-$C_{10}$ alkenyl, an alkenyl group comprising up to 6 carbon atoms is a $C_2$-$C_6$ alkenyl and an alkenyl comprising up to 5 carbon atoms is a $C_2$-$C_5$ alkenyl. A $C_2$-$C_5$ alkenyl includes $C_5$ alkenyls, $C_4$ alkenyls, $C_3$ alkenyls, and $C_2$ alkenyls. A $C_2$-$C_6$ alkenyl includes all moieties described above for $C_2$-$C_5$ alkenyls but also includes $C_6$ alkenyls. A $C_2$-$C_{10}$ alkenyl includes all moieties described above for $C_2$-$C_5$ alkenyls and $C_2$-$C_6$ alkenyls, but also includes $C_7$, $C_8$, $C_9$ and $C_{10}$ alkenyls. Similarly, a $C_2$-$C_{12}$ alkenyl includes all the foregoing moieties, but also includes $C_{11}$ and $C_{12}$ alkenyls. Non-limiting examples of $C_2$-$C_{12}$ alkenyl include ethenyl (vinyl), 1-propenyl, 2-propenyl (allyl), iso-propenyl, 2-methyl-1-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, and 11-dodecenyl. Examples of $C_1$-$C_3$ alkyl includes methyl, ethyl, n-propyl, and i-propyl. Examples of $C_1$-$C_4$ alkyl includes methyl, ethyl, n-propyl, i-propyl, n-butyl, i-butyl, and sec-butyl. Unless stated otherwise specifically in the specification, an alkyl group can be optionally substituted.

"Alkenylene" or "alkenylene chain" refers to a straight or branched divalent hydrocarbon chain radical, having from two to twelve carbon atoms, and having one or more carbon-carbon double bonds. Non-limiting examples of $C_2$-$C_{12}$ alkenylene include ethene, propene, butene, and the like. The alkenylene chain is attached to the rest of the molecule through a single bond and to the radical group through a single bond. The points of attachment of the alkenylene chain to the rest of the molecule and to the radical group can be through one carbon or any two carbons within the chain. Unless stated otherwise specifically in the specification, an alkenylene chain can be optionally substituted.

"Alkynyl" or "alkynyl group" refers to a straight or branched hydrocarbon chain radical having from two to twelve carbon atoms, and having one or more carbon-carbon triple bonds. Each alkynyl group is attached to the rest of the molecule by a single bond. Alkynyl groups comprising any number of carbon atoms from 2 to 12 are included. An alkynyl group comprising up to 12 carbon atoms is a $C_2$-$C_{12}$ alkynyl, an alkynyl comprising up to 10 carbon atoms is a $C_2$-$C_{10}$ alkynyl, an alkynyl group comprising up to 6 carbon atoms is a $C_2$-$C_6$ alkynyl and an alkynyl comprising up to 5 carbon atoms is a $C_2$-$C_5$ alkynyl. A $C_2$-$C_5$ alkynyl includes $C_5$ alkynyls, $C_4$ alkynyls, $C_3$ alkynyls, and $C_2$ alkynyls. A $C_2$-$C_6$ alkynyl includes all moieties described above for $C_2$-$C_5$ alkynyls but also includes $C_6$ alkynyls. A $C_2$-$C_{10}$ alkynyl includes all moieties described above for $C_2$-$C_5$ alkynyls and $C_2$-$C_6$ alkynyls, but also includes $C_7$, $C_8$, $C_9$ and $C_{10}$ alkynyls. Similarly, a $C_2$-$C_{12}$ alkynyl includes all the foregoing moieties, but also includes Cu and $C_{12}$ alkynyls. Non-limiting examples of $C_2$-$C_{12}$ alkenyl include ethynyl, propynyl, butynyl, pentynyl and the like. Unless stated otherwise specifically in the specification, an alkyl group can be optionally substituted.

"Alkynylene" or "alkynylene chain" refers to a straight or branched divalent hydrocarbon chain radical, having from two to twelve carbon atoms, and having one or more carbon-carbon triple bonds. Non-limiting examples of $C_2$-$C_{12}$ alkynylene include ethynylene, propargylene and the like. The alkynylene chain is attached to the rest of the molecule through a single bond and to the radical group through a single bond. The points of attachment of the alkynylene chain to the rest of the molecule and to the radical group can be through one carbon or any two carbons within the chain. Unless stated otherwise specifically in the specification, an alkynylene chain can be optionally substituted.

"Alkoxy" refers to a radical of the formula —OR$_a$ where R$_a$ is an alkyl, alkenyl or alknyl radical as defined above containing one to twelve carbon atoms. Unless stated otherwise specifically in the specification, an alkoxy group can be optionally substituted.

"Alkylamino" refers to a radical of the formula —NHR$_a$ or —NR$_a$R$_a$ where each R$_a$ is, independently, an alkyl, alkenyl or alkynyl radical as defined above containing one to twelve carbon atoms. Unless stated otherwise specifically in the specification, an alkylamino group can be optionally substituted.

"Alkylcarbonyl" refers to the —C(=O)R$_a$ moiety, wherein R$_a$ is an alkyl, alkenyl or alkynyl radical as defined above. A non-limiting example of an alkyl carbonyl is the methyl carbonyl ("acetal") moiety. Alkylcarbonyl groups can also be referred to as "Cw-Cz acyl" where w and z depicts the range of the number of carbon in R$_a$, as defined above. For example, "$C_1$-$C_{10}$ acyl" refers to alkylcarbonyl group as defined above, where R$_a$ is $C_1$-$C_{10}$ alkyl, $C_1$-$C_{10}$ alkenyl, or $C_1$-$C_{10}$ alkynyl radical as defined above. Unless stated otherwise specifically in the specification, an alkyl carbonyl group can be optionally substituted.

"Aryl" refers to a hydrocarbon ring system radical comprising hydrogen, 6 to 18 carbon atoms and at least one aromatic ring. For purposes of this invention, the aryl radical can be a monocyclic, bicyclic, tricyclic or tetracyclic ring system, which can include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" is meant to include aryl radicals that are optionally substituted.

"Aralkyl" refers to a radical of the formula —R$_b$—R$_c$ where R$_b$ is an alkylene, alkenylene or alkynylene group as defined above and R$_c$ is one or more aryl radicals as defined above, for example, benzyl, diphenylmethyl and the like.

Unless stated otherwise specifically in the specification, an aralkyl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl. cycloalkenyl and cycloalkynyl as defined herein. Unless stated otherwise specifically in the specification, a carbocyclyl group can be optionally substituted.

"Cycloalkyl" refers to a stable non-aromatic monocyclic or polycyclic fully saturated hydrocarbon radical consisting solely of carbon and hydrogen atoms, which can include fused or bridged ring systems, having from three to twenty carbon atoms, preferably having from three to ten carbon atoms, and which is attached to the rest of the molecule by a single bond. Monocyclic cycloalkyl radicals include, for example, cyclopropyl, cyclobutyl, cyclopentyl, cyclohexyl, cycloheptyl, and cyclooctyl. Polycyclic cycloalkyl radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon radical consisting solely of carbon and hydrogen atoms, having one or more carbon-carbon double bonds, which can include fused or bridged ring systems, having from three to twenty carbon atoms, preferably having from three to ten carbon atoms, and which is attached to the rest of the molecule by a single bond. Monocyclic cycloalkenyl radicals include, for example, cyclopentenyl, cyclohexenyl, cycloheptenyl, cycloctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon radical consisting solely of carbon and hydrogen atoms, having one or more carbon-carbon triple bonds, which can include fused or bridged ring systems, having from three to twenty carbon atoms, preferably having from three to ten carbon atoms, and which is attached to the rest of the molecule by a single bond. Monocyclic cycloalkynyl radicals include, for example, cycloheptynyl, cyclooctynyl, and the like. Unless otherwise stated specifically in the specification, a cycloalkynyl group can be optionally substituted.

"Cycloalkylalkyl" refers to a radical of the formula —$R_b$—$R_d$ where $R_b$ is an alkylene, alkenylene, or alkynylene group as defined above and $R_d$ is a cycloalkyl, cycloalkenyl, cycloalkynyl radical as defined above. Unless stated otherwise specifically in the specification, a cycloalkylalkyl group can be optionally substituted.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group can be optionally substituted.

"Haloalkenyl" refers to an alkenyl radical, as defined above, that is substituted by one or more halo radicals, as defined above, e.g., 1-fluoropropenyl, 1,1-difluorobutenyl, and the like. Unless stated otherwise specifically in the specification, a haloalkenyl group can be optionally substituted.

"Haloalkynyl" refers to an alkynyl radical, as defined above, that is substituted by one or more halo radicals, as defined above, e.g., 1-fluoropropynyl, 1-fluorobutynyl, and the like. Unless stated otherwise specifically in the specification, a haloalkenyl group can be optionally substituted.

"Heterocyclyl," "heterocyclic ring" or "heterocycle" refers to a stable 3- to 20-membered non-aromatic ring radical which consists of two to twelve carbon atoms and from one to six heteroatoms selected from the group consisting of nitrogen, oxygen and sulfur. Heterocyclyl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group can be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group can be optionally substituted.

"Heterocyclylalkyl" refers to a radical of the formula —$R_b$—$R_e$ where $R_b$ is an alkylene, alkenylene, or alkynylene chain as defined above and $R_e$ is a heterocyclyl radical as defined above, and if the heterocyclyl is a nitrogen-containing heterocyclyl, the heterocyclyl can be attached to the alkyl, alkenyl, alkynyl radical at the nitrogen atom. Unless stated otherwise specifically in the specification, a heterocyclylalkyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in this disclosure, a heteroaryl group can be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group can be optionally substituted.

"Heteroarylalkyl" refers to a radical of the formula —$R_b$—$R_f$ where $R_b$ is an alkylene, alkenylene, or alkynylene chain as defined above and $R_f$ is a heteroaryl radical as defined above. Unless stated otherwise specifically in the specification, a heteroarylalkyl group can be optionally substituted.

"Thioalkyl" refers to a radical of the formula —$SR_a$ where $R_a$ is an alkyl, alkenyl, or alkynyl radical as defined above containing one to twelve carbon atoms. Unless stated otherwise specifically in the specification, a thioalkyl group can be optionally substituted.

The term "substituted" used herein means any of the above groups (i.e., alkyl, alkylene, alkenyl, alkenylene, alkynyl, alkynylene, alkoxy, alkylamino, alkylcarbonyl, thioalkyl, aryl, aralkyl, carbocyclyl, cycloalkyl, cycloalkenyl, cycloalkynyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted also means any of" the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylal- kyl, heteroaryl, N-heteroaryl and/or heteroarylalkyl group. In addition, each of the foregoing substituents can also be optionally substituted with one or more of the above substituents.

As used herein, the symbol

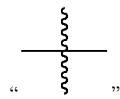

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

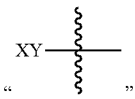

indicates that the chemical entity "XY" is bonded to another chemical entity via the point of attachment bond. Furthermore, the specific point of attachment to the non-depicted chemical entity can be specified by inference. For example, the compound $CH_3$—$R^3$, wherein $R^3$ is H or

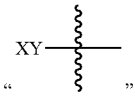

infers that when $R^3$ is "XY", the point of attachment bond is the same bond as the bond by which $R^3$ is depicted as being bonded to $CH_3$.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring can be replaced with a nitrogen atom.

"Optional" or "optionally" means that the subsequently described event of circumstances can or cannot occur, and that the description includes instances where said event or circumstance occurs and instances in which it does not. For example, "optionally substituted aryl" means that the aryl radical can or cannot be substituted and that the description includes both substituted aryl radicals and aryl radicals having no substitution.

Total synthesis refers to the complete chemical synthesis of a complex molecule, typically a natural product or a structurally similar analog or derivative thereof, starting from commercially available precursor compounds. It is often desirable to perform total syntheses in a "convergent" manner, where efficiency and overall chemical yield are improved by synthesizing several complex individual components in stage one, followed by combination of the components in a subsequent stage to yield a more advanced compound or final product. While convergent synthetic methods are desirable, for complex molecular frameworks such as communesins generally, or (−)-communesins specifically, there can be many different possible convergent approaches. The success of any particular approach is highly unpredictable.

The compounds of the invention, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present invention is meant to include all such possible isomers, as well as their racemic and optically pure forms whether or not they are specifically depicted herein. Optically active (+) and (−), (R)- and (S)-, or (D)- and (L)-isomers can be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

A "tautomer" refers to a proton shift from one atom of a molecule to another atom of the same molecule. The present invention includes tautomers of any said compounds.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallization is a method commonly used to isolate a reaction product, for example one of the compounds disclosed herein, in purified form. Often, crystallization produces a solvate of the compound of the invention. As used herein, the term "solvate" refers to an aggregate that comprises one or more molecules of a compound of the invention with one or more molecules of solvent, typically in co-crystallized form. The solvent can be water, in which case the solvate can be a hydrate. Alternatively, the solvent can be an organic solvent. Thus, the compounds of the present invention can exist as a hydrate, including a monohydrate, dihydrate, hemihydrate, sesquihydrate, trihydrate, tetrahydrate and the like, as well as the corresponding solvated forms. The compound of the invention can be true solvates, while in other cases, the compound of the invention can merely retain adventitious water or be a mixture of water plus some adventitious solvent.

The chemical naming protocol and structure diagrams used herein are a modified form of the I.U.P.A.C. nomenclature system, using the ACD/Name Version 9.07 software program, ChemDraw Ultra Version 11.0.1 and/or ChemDraw Ultra Version 14.0 and/or ChemDraw Professional 16.0.0.82 software naming program (CambridgeSoft), or the like. For complex chemical names employed herein, a substituent group is named before the group to which it attaches. For example, cyclopropylethyl comprises an ethyl backbone with cyclopropyl substituent. Except as described below, all bonds are identified in the chemical structure diagrams herein, except for some carbon atoms, which are assumed to be bonded to sufficient hydrogen atoms to complete the valency.

The invention disclosed herein is also meant to encompass the in vivo metabolic products of the disclosed compounds. Such products can result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabeled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

As used herein, a "subject" can be a human, non-human primate, mammal, rat, mouse, cow, horse, pig, sheep, goat, dog, cat, insect and the like. The subject can be suspected of having or at risk for having a cancer, such as a blood cancer, or another disease or condition. Diagnostic methods for various cancers, and the clinical delineation of cancer, are known to those of ordinary skill in the art. The subject can also be suspected of having an infection or abnormal cardiovascular function.

"Mammal" includes humans and both domestic animals such as laboratory animals and household pets (e.g., cats, dogs, swine, cattle, sheep, goats, horses, rabbits), and non-domestic animals such as wildlife and the like.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"An "effective amount" refers to a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound can vary according to factors such as the disease state, age, sex, and weight of the subject, and the ability of the compound to elicit a desired response in the subject. Dosage regimens can be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to a castration-resistant form. Typically, a prophylactic dose is used in subjects prior to or at an earlier stage of disease, so that a prophylactically effective amount can be less than a therapeutically effective amount.

"Treating" or "treatment" as used herein covers the treatment of the disease or condition of interest in a mammal, preferably a human, having the disease or condition of interest, and includes (but is not limited to):

1. preventing the disease or condition from occurring in a mammal, in particular, when such mammal is predisposed to the condition but has not yet been diagnosed as having it;
2. inhibiting the disease or condition, i.e., arresting its development;
3. relieving the disease or condition, i.e., causing regression of the disease or condition (ranging from reducing the severity of the disease or condition to curing the disease of condition); or
4. relieving the symptoms resulting from the disease or condition, i.e., relieving pain without addressing the underlying disease or condition. As used herein, the terms "disease" and "condition" can be used interchangeably or can be different in that the particular malady or condition cannot have a known causative agent (so that etiology has not yet been worked out) and it is therefore not yet recognized as a disease but only as an undesirable condition or syndrome, wherein a more or less specific set of symptoms have been identified by clinicians.

Throughout the present specification, the terms "about" and/or "approximately" can be used in conjunction with numerical values and/or ranges. The term "about" is understood to mean those values near to a recited value. For example, "about 40 [units]" can mean within ±25% of 40 (e.g., from 30 to 50), within ±20%, ±15%, ±10%, ±9%, ±8%, ±7%, ±6%, ±5%, ±4%, ±3%, 2%, 1%, less than ±1%, or any other value or range of values therein or therebelow. Furthermore, the phrases "less than about [a value]" or "greater than about [a value]" should be understood in view of the definition of the term "about" provided herein. The terms "about" and "approximately" can be used interchangeably.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range can be an endpoint for the range encompassed thereby (e.g., the range 50-80 includes the ranges with endpoints such as 55-80, 50-75, etc.).

Following below are more detailed descriptions of various concepts related to, and embodiments of, inventive methods for Convergent and Biomimetic Enantioselective Total Synthesis of (−)-Communesin F. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

In one embodiment, the present disclosure relates to compounds of Formula (I):

Formula (I)

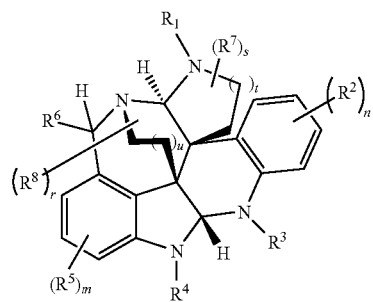

or a pharmaceutically acceptable salt, tautomer or stereoisomer thereof is described, wherein:

$R^1$, $R^3$, and $R^4$ are each independently selected from H, $C_1$-$C_{12}$ alkyl, $C_2$-$C_{12}$ alkenyl, $C_2$-$C_{12}$ alkynyl, —C(=O)$R^9$, —C(=O)N$R^9R^{10}$, —S(=O)$R^{12}$, aryl, heteroaryl, carbocyclyl, or heterocyclyl, wherein $R^3$ and $R^4$ taken together with the carbon atoms to which they are attached form an aryl, heteroaryl, carbocyclic, or heterocyclic ring;

$R^2$ and $R^5$ are each independently selected from F, Cl, Br, I, —OH, —O$R^9$, —OC(=O)$R^9$, —S(=O)$_u R^{12}$, —N$R^9R^{10}$, $C_1$-$C_{12}$ alkyl, $C_2$-$C_{12}$ alkenyl, $C_2$-$C_{12}$ alkynyl, aryl, heteroaryl, carbocyclyl, or heterocyclyl;

$R^6$ is independently H, —OH, —O$R^9$, —OC(=O)$R^9$, —S(=O)$_u R^{12}$, —N$R^9R^{10}$, $C_1$-$C_{12}$ alkyl, $C_1$-$C_{12}$ alkyl, $C_2$-$C_{12}$ alkenyl, $C_2$-$C_{12}$ alkynyl aryl, heteroaryl, carbocyclyl, or heterocyclyl;

$R^7$ and $R^8$ are each independently selected from H, $C_1$-$C_{12}$ alkyl; $C_2$-$C_{12}$ alkenyl, $C_2$-$C_{12}$ alkynyl, —C(=O)$R^9$, —C(=O)N$R^9R^{10}$, —S(=O)$_u R^{12}$, —OH, —O$R^9$, —OC(=O)$R^9$, —N$R^9R^{10}$, aryl, heteroaryl, carbocyclyl, or heterocyclyl, wherein two $R^7$ or two $R^8$ groups taken together with the carbon atoms to which they are attached form an aryl, heteroaryl, carbocyclic, or heterocyclic ring;

$R^9$ and $R^{10}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^9$ and $R^{10}$ taken together with the carbon atoms to which they are attached form an aryl, heteroaryl, carbocyclic, or heterocyclic ring;

$R^{12}$ is $C_1$-$C_{12}$ alkyl, $C_2$-$C_{12}$ alkenyl, $C_2$-$C_{12}$ alkynyl, aryl, heteroaryl, carbocyclyl, heterocyclyl, —(CH$_2$)$_n$SiMe$_3$, —(CH$_2$)$_n R^9$;

m and t are each independently an integer from 0 to 3;

n, r, s, and v are each independently an integer from 0 to 4; and u is 0, 1, or 2;

with the following provisos:

when $R^1$ is

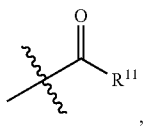
, wherein $R^{11}$ is Me, Et, n-Pr,

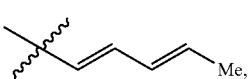 [SMILES: */C=C/C=C/C]

or;

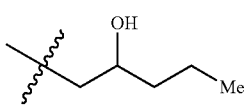 [SMILES: *CC(O)CCC]

$R^4$ is Me;
m, n, r, and s are 0;
t and u are 1; then $R^6$ is not

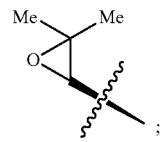
;

and
when $R^1$ is

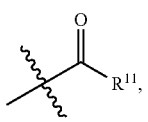
, wherein $R^{11}$ is Me;
$R^4$ is Me;
m, n, r, and s are 0;
t and u are 1; then
$R^6$ is not

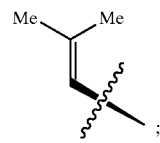
;

and
when $R^1$ is

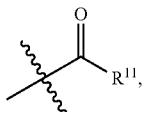
, wherein $R^{11}$ is Me, or

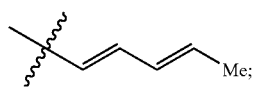 [SMILES: */C=C/C=C/C]

$R_4$ is H;
m, n, r, and s are 0;
t and u are 1; then
$R^6$ is not

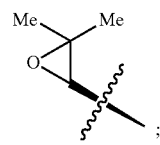
;

and
when R¹ is

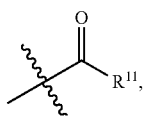

wherein R¹¹ is

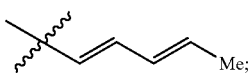 [SMILES: */C=C/C=C/C]

R⁴ is —CHO;
m, n, r, and s are 0;
t and u are 1; and
R₆ is not

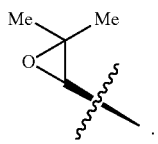

In another embodiment, the present disclosure relates to compounds of Formula (I):

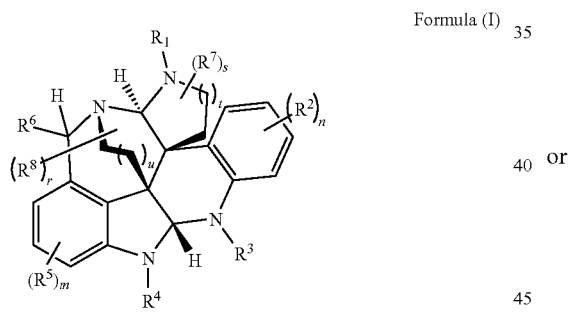

Formula (I)

or a pharmaceutically acceptable salt, tautomer or stereoisomer thereof is described, wherein:
R¹, R³, and R⁴ are each independently selected from H, $C_1$-$C_{12}$ alkyl, $C_2$-$C_{12}$ alkenyl, $C_2$-$C_{12}$ alkynyl, —C(=O)R⁹, —C(=O)NR⁹R¹⁰, —S(=O)$_u$R¹², aryl, heteroaryl, carbocyclyl, or heterocyclyl, wherein R³ and R⁴ taken together with the carbon atoms to which they are attached form an aryl, heteroaryl, carbocyclic, or heterocyclic ring;
R² and R⁵ are each independently selected from F, Cl, Br, I, —OH, —OR⁹, —OC(=O)R⁹, —S(=O)$_u$R¹², —NR⁹R₁, $C_1$-$C_{12}$ alkyl, $C_2$-$C_{12}$ alkenyl, $C_2$-$C_{12}$ alkynyl, aryl, heteroaryl, carbocyclyl, or heterocyclyl;
R⁶ is independently H, —OH, —OR⁹, —OC(=O)R⁹, —S(=O)$_u$R¹², —NR⁹R¹⁰, $C_1$-$C_{12}$ alkyl, $C_1$-$C_{12}$ alkyl, $C_2$-$C_{12}$ alkenyl, $C_2$-$C_{12}$ alkynyl aryl, heteroaryl, carbocyclyl, or heterocyclyl;
R⁷ and R⁸ are each independently selected from H, $C_1$-$C_{12}$ alkyl; $C_2$-$C_{12}$ alkenyl, $C_2$-$C_{12}$ alkynyl, —C(=O)R⁹, —C(=O)NR⁹R¹⁰, —S(=O)$_u$R¹², —OH, —OR⁹, —OC(=O)R⁹, —NR⁹R¹⁰, aryl, heteroaryl, carbocyclyl, or heterocyclyl, wherein two R⁷ or two R⁵ groups taken together with the carbon atoms to which they are attached form an aryl, heteroaryl, carbocyclic, or heterocyclic ring;
R⁹ and R₁₀ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein R⁹ and R₁₀ taken together with the carbon atoms to which they are attached form an aryl, heteroaryl, carbocyclic, or heterocyclic ring;
R¹² is $C_1$-$C_{12}$ alkyl, $C_2$-$C_{12}$ alkenyl, $C_2$-$C_{12}$ alkynyl, aryl, heteroaryl, carbocyclyl, heterocyclyl, —(CH₂)$_n$SiMe₃, —(CH₂)$_n$R⁹;
m and t are each independently an integer from 0 to 3;
n, r, s, and v are each independently an integer from 0 to 4;
and
u is 0, 1, or 2;
with the proviso that the compound of Formula (I) is not (−)-communesin A, (−)-communesin B, (−)-communesin C, (+)-communesin D, (−)-communesin E, (−)-communesin F, (−)-communesin G, or (−)-communesin H.

In various embodiments of Formula (I) compounds, R⁶ is H, $C_1$-$C_{12}$ alkyl, $C_1$-$C_{12}$ alkenyl, aryl, heteroaryl, carbocyclyl, or heterocyclyl. In other embodiments, R⁴ is H, —C(=O)R⁹, $C_1$-$C_{12}$ alkyl, aryl or heteroaryl. In some embodiments, R³ is H, $C_1$-$C_{12}$ alkyl, or —S(=O)R¹², wherein R¹² is Ph or —(CH)₂SiMe₃. In other embodiments, R² and R⁵ are each independently F, Br, Cl, I, $C_1$-$C_{12}$ alkyl, aryl or heteroaryl.

In various other embodiments of Formula (I) compounds, R⁶ is

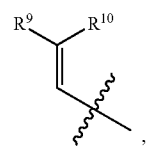

or

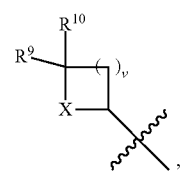

and wherein X is O, NR⁹, or —S(=O)$_n$R¹². In still other embodiments, R¹ is —C(=O)R⁹. In some embodiments, R⁹ of a —C(=O)R⁹ group is Me, Et, n-Pr,

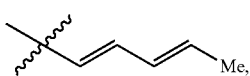 [SMILES: */C=C/C=C/C]

or

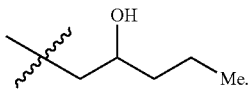 [SMILES: *CC(O)CCC]

In various embodiments, $R^6$ is

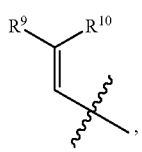

or

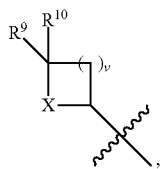

wherein X is O, $NR^9$, or $-S(=O)_uR_{12}$.

In another embodiment, the present disclosure relates to a pharmaceutical composition comprising a compound of Formula (I) and a pharmaceutically acceptable excipient.

In one embodiment, the present disclosure relates to compounds of Formula (V):

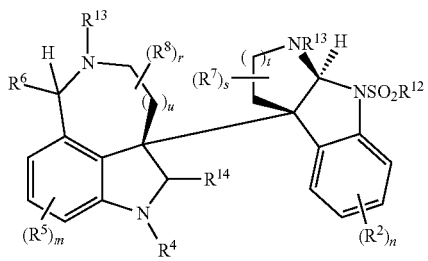

Formula (V)

or a pharmaceutically acceptable salt, tautomer or stereoisomer thereof is described, wherein:
$R^4$ is independently selected from H, $C_1$-$C_{12}$ alkyl, $C_2$-$C_{12}$ alkenyl, $C_2$-$C_{12}$ alkynyl, $-C(=O)R^9$, $-C(=O)NR^9R^{10}$, $-S(=O)_uR_{12}$, aryl, heteroaryl, carbocyclyl, or heterocyclyl, wherein $R^3$ and $R^4$ taken together with the carbon atoms to which they are attached form an aryl, heteroaryl, carbocyclic, or heterocyclic ring;
$R^2$ and $R^5$ are each independently selected from F, Cl, Br, I, $-OH$, $-OR^9$, $-OC(=O)R^9$, $-S(=O)_uR^{12}$, $-NR^9R^{10}$, $C_1$-$C_{12}$ alkyl, $C_2$-$C_{12}$ alkenyl, $C_2$-$C_{12}$ alkynyl, aryl, heteroaryl, carbocyclyl, or heterocyclyl;
$R^6$ is independently H, $-OH$, $-OR^9$, $-OC(=O)R^9$, $-S(=O)_uR^{12}$, $-NR^9R^{10}$, $C_1$-$C_{12}$ alkyl, $C_1$-$C_{12}$ alkyl, $C_2$-$C_{12}$ alkenyl, $C_2$-$C_{12}$ alkynyl aryl, heteroaryl, carbocyclyl, or heterocyclyl;
$R^7$ and $R^8$ are each independently selected from H, $C_1$-$C_{12}$ alkyl; $C_2$-$C_{12}$ alkenyl, $C_2$-$C_{12}$ alkynyl, $-C(=O)R^9$, $-C(=O)NR^9R^{10}$, $-S(=O)_uR^{12}$, $-OH$, $-OR^9$, $-OC(=O)R^9$, $-NR^9R^{10}$, aryl, heteroaryl, carbocyclyl, or heterocyclyl, wherein two $R^7$ or two $R^8$ groups taken together with the carbon atoms to which they are attached form an aryl, heteroaryl, carbocyclic, or heterocyclic ring;
$R^9$ and $R^{10}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, or heterocyclyl, wherein $R^9$ and $R^{10}$ taken together with the carbon atoms to which they are attached form an aryl, heteroaryl, carbocyclic, or heterocyclic ring;
$R^{12}$ is $C_1$-$C_{12}$ alkyl, $C_2$-$C_{12}$ alkenyl, $C_2$-$C_{12}$ alkynyl, aryl, heteroaryl, carbocyclyl, heterocyclyl, $-(CH_2)_nSiMe_3$, $-(CH_2)_nR^9$;
$R^{13}$ is

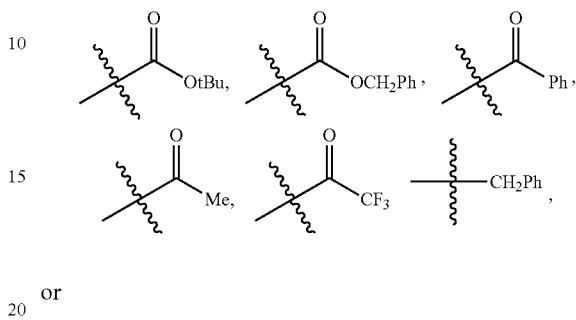

or

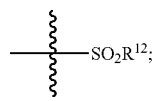

$R^{14}$ is $-OH$, $-OR^9$, $-NR^9R^{10}$, $S(O)R^{12}$, or $P(O)OR^9$;
m and t are each independently an integer from 0 to 3;
n, r, s, and v are each independently an integer from 0 to 4; and
u is 0, 1, or 2.

In one embodiment, $-S(=O)_uR^{12}$ is

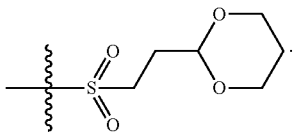 [SMILES: *S(=O)(=O)CCC1OCCCO1]

In one embodiment, the present disclosure provides a method of treating a disease or condition comprising administering an effective amount of a compound of Formula (I), or a pharmaceutical composition thereof to a subject. In one embodiment, the subject is a mammal. In another embodiment, the mammal is a human.

In some embodiments, the disease or condition being treated with a compound of Formula (I) is cancer. In other embodiments, the cancer is a cancer of the blood. In various other embodiments, the cancer of the blood to be treated can be selected from leukemias, lymphomas, Hodgkin's disease, myeloma, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML, with trilineage myelodysplasia (AM-LITMDS), mixed lineage leukemia (MLL), myelodysplastic syndromes (MDSs), myeloproliferative disorders (MPD), and multiple myeloma (MM). In particular embodiments, the cancer of the blood is histiocytic leukemia, monocytic leukemia, Burkitt's lymphoma, Hodgkin's' lymphoma, T-cell leukemia, or B-cell leukemia.

Cancers of the blood, also termed hematologic cancers, begin in the blood forming tissue, such as bone marrow, or in cells of the immune system, and affects the production and function of blood cells. These abnormal blood cells, or cancerous cells, prevent the blood from performing many of its functions, like fighting off infections or preventing serious bleeding. Mutated forms can be resistant to currently available treatments, thus discovery and development of novel therapeutic agents is of critical importance.

In other embodiments, the disease or condition being treated with a compound of Formula (I), or pharmaceutical compositions thereof is a bacterial infection. Bacterial infections can be gram-positive or gram-negative with either type capable of high pathogenicity. In some embodiments, the treatment is for gram-positive infections. In other embodiments, the treatment is for gram-negative infections. In more specific embodiments, the bacterial infection treated is an infection of *Escherichia coli, Klebsiella pneumoniae, Pseudomonas aeruginosa, Acinetobacter baumanii, Neisseria gonorrhoeae,* or *Bacillus subtilis*.

Drug-resistant Gram-negative infections, such as *Klebsiella, Pseudomonas,* and *Acinetobacter,* have emerged as major concerns in hospitals, nursing homes, other healthcare settings, and more recently in the community. These types of infections disproportionately affect the very ill and the elderly, and often there are limited or no treatment options. The compounds of Formula (I) are suitable for treating such infections.

In other embodiments, the disease or condition being treated with a compound of Formula (I), or pharmaceutical compositions thereof is a fungal infection. In one embodiment, the fungal infections occur in subjects with a normal immune systems. In other embodiments, the fungal infections occur in subjects with weakened immune systems. In other embodiments, the infection occurs on the skin, nails, genitals, esophagus, or other internal organs. In particular embodiments, the fungal infection treated with a compound of Formula (I) is a fungal infection of *Candida albicans, Trichophyton mentagrophytes,* or *Amorphotheca resinae*. In other embodiments, treatment of the fungal infections is by oral dosage or topical administration.

In another embodiment, the disease or condition being treated with a compound of Formula (I), or pharmaceutical compositions thereof is a viral infection. In one particular embodiment, the viral infection is Herpes simplex type 1.

In other embodiments, the disease or condition being treated with a compound of Formula (I), or pharmaceutical compositions thereof is abnormal cardiovascular function. In one embodiment, the abnormal cardiovascular function is bradycardia.

In yet another embodiment, insect infestations are treated with a compound of Formula (I), or an insecticidal composition thereof. In one specific embodiment, the insect infestation to be treated is silkworms at the third instar larval stage. The third instar is a development stage of arthropod larvae characterized by changes in changes in body proportions, colors, patterns, number of body segments, and/or head width.

In various embodiments, the present disclosure is directed to synthetic methods including the expedient diazene-directed assembly of two advanced fragments described herein, to secure the congested C3a-C3a' linkage of the communesin framework in three steps, followed by a highly efficient aminal reorganization to access the heptacyclic communesin core in only two additional steps. Enantioselective syntheses of the two fragments were developed, with highlights including the catalytic asymmetric halocyclization and diastereoselective oxyamination reactions of tryptamine derivatives, a stereoselective sulfinimine allylation, and an efficient cyclotryptamine-C3a-sulfamate synthesis by either a new silver-promoted nucleophilic amination or a rhodium-catalyzed C—H amination protocol. The versatile synthesis of the fragments, their stereocontrolled assembly, and the efficient aminal-exchange as supported by in situ monitoring experiments, in addition to the final stage N1'-acylation of the communesin core provide a highly convergent synthesis of communesins.

In one embodiment, the present disclosure provides a method of making compounds of Formula (I) by a rearrangement of compounds of Formula (V):

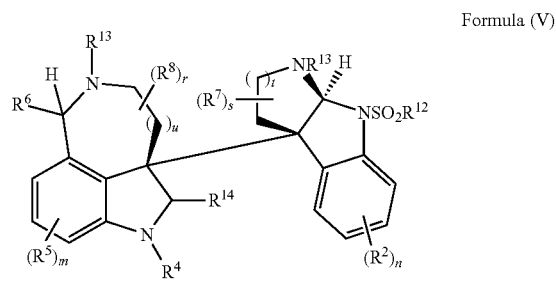

Formula (V)

In another embodiment, the present disclosure provides a method of making compounds of Formula (V) by a radical recombination reaction of Formula (VI):

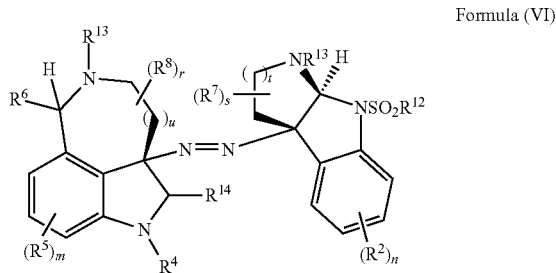

Formula (VI)

In another embodiment, the present disclosure provides a method of making compounds of Formula (VI) by the extrusion of sulfur from compounds of Formula (VII):

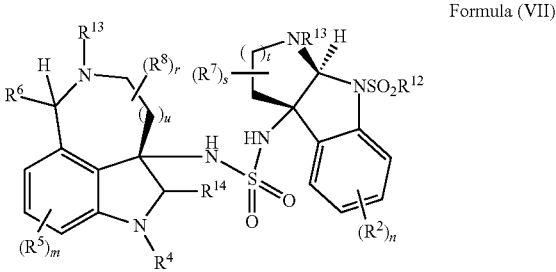

Formula (VII)

In still another embodiment, the present disclosure provides a method of making compounds of Formula (VII) by a nucleophilic substitution reaction between a compound of Formula (III) and a compound of Formula (VIII):

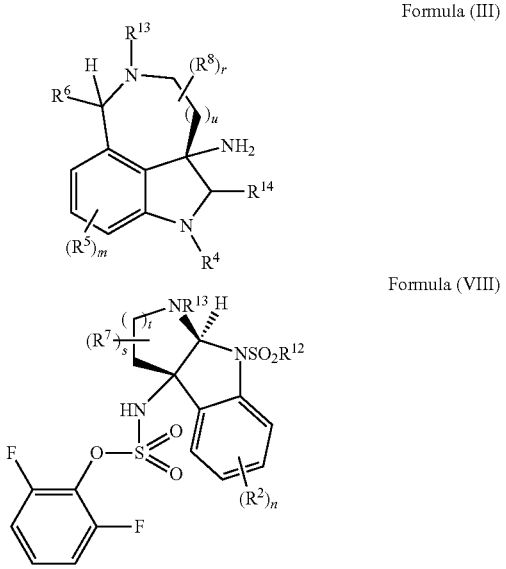

Formula (III)

Formula (VIII)

In one embodiment, the first biomimetic enantioselective total synthesis of (−)-communesin F based on a late-stage heterodimerization and aminal exchange is provided. It is to be understood that these methods and approaches can be generalized and applied to the synthesis of a variety of compounds, such as those represented by Formula (I).

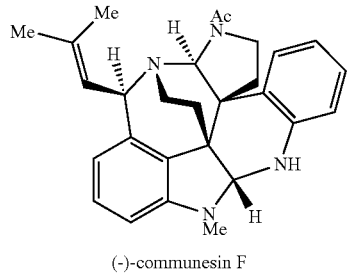

(−)-communesin F

In various embodiments, the pharmaceutical compositions of the present disclosure can be formulated for administration by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters.

The effective amount of a compound of Formula (I), pharmaceutically acceptable salts, esters, prodrugs, hydrates, solvates and isomers thereof, or a pharmaceutical composition comprising a compound of Formula (I) or a pharmaceutically acceptable salt thereof may be determined by one skilled in the art based on known methods.

In one embodiment, a pharmaceutical composition or a pharmaceutical formulation of the present disclosure comprises a compound of Formula (I) or a pharmaceutically acceptable salt thereof, and a pharmaceutically acceptable carrier, diluent, and/or excipient. Pharmaceutically acceptable carriers, diluents or excipients include without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

In one embodiment, suitable pharmaceutically acceptable carriers include, but are not limited to, inert solid fillers or diluents and sterile aqueous or organic solutions. Pharmaceutically acceptable carriers are well known to those skilled in the art and include, but are not limited to, from about 0.01 to about 0.1 M and preferably 0.05M phosphate buffer or 0.8% saline. Such pharmaceutically acceptable carriers can be aqueous or non-aqueous solutions, suspensions and emulsions. Examples of non-aqueous solvents suitable for use in the present application include, but are not limited to, propylene glycol, polyethylene glycol, vegetable oils such as olive oil, and injectable organic esters such as ethyl oleate.

Aqueous carriers suitable for use in the present application include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the present application can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the present application include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellant.

Solid carriers suitable for use in the present application include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Parenteral carriers suitable for use in the present application include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the present application can be mixed as needed with disintegrants, diluents, granulating agents, lubricants, binders and the like using conventional techniques known in the art. The carriers can also be sterilized using methods that do not deleteriously react with the compounds, as is generally known in the art.

Diluents may be added to the formulations of the present invention. Diluents increase the bulk of a solid pharmaceutical composition and/or combination, and may make a pharmaceutical dosage form containing the composition and/or combination easier for the patient and care giver to handle. Diluents for solid compositions and/or combinations include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

The pharmaceutical composition of the present invention may be prepared into any type of formulation and drug delivery system by using any of the conventional methods well-known in the art. The inventive pharmaceutical composition may be formulated into injectable formulations, which may be administered by routes including intrathecal, intraventricular, intravenous, intraperitoneal, intranasal, intraocular, intramuscular, subcutaneous or intraosseous. Also, it may also be administered orally, or parenterally through the rectum, the intestines or the mucous membrane in the nasal cavity (see Gennaro, A. R., ed. (1995) Remington's Pharmaceutical Sciences). Preferably, the composition is administered topically, instead of enterally. For instance, the composition may be injected, or delivered via a targeted drug delivery system such as a reservoir formulation or a sustained release formulation.

The pharmaceutical formulation of the present invention may be prepared by any well-known methods in the art, such as mixing, dissolving, granulating, dragee-making, levigating, emulsifying, encapsulating, entrapping, or lyophilizing processes. As mentioned above, the compositions of the present invention may include one or more physiologically acceptable carriers such as excipients and adjuvants that facilitate processing of active molecules into preparations for pharmaceutical use.

Proper formulation is dependent upon the route of administration chosen. For injection, for example, the composition may be formulated in an aqueous solution, preferably in physiologically compatible buffers such as Hank's solution, Ringer's solution, or physiological saline buffer. For transmucosal or nasal administration, penetrants appropriate to the barrier to be permeated are used in the formulation. Such penetrants are generally known in the art. In a one embodiment of the present invention, the inventive compound may be prepared in an oral formulation. For oral administration, the compounds can be formulated readily by combining the active compounds with pharmaceutically acceptable carriers known in the art. Such carriers enable the disclosed compound to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use may be obtained as solid excipients, optionally grinding a resulting mixture, and processing the mixture of granules, after adding suitable adjuvants, if desired, to obtain tablets or dragee cores. Suitable excipients may be, in particular, fillers such as sugars, including lactose, sucrose, mannitol, or sorbitol; cellulose formulation such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP) formulation. Also, disintegrating agents may be employed, such as cross-linked polyvinylpyrrolidone, agar, or alginic acid or a salt thereof such as sodium alginate. Also, wetting agents, such as sodium dodecyl sulfate and the like, may be added.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compounds doses.

The present disclosure is in various embodiments directed to a unified and convergent approach to the communesin alkaloids involving the stereocontrolled oxidative union of two dissimilar tryptamine derivatives followed by reorganization of a C3a-C3a' linked heterodimer, reminiscent of the pathways leading to the related calycanthoids (Scheme 1).

This method involves the directed and stereocontrolled union of two dissimilar fragments followed by selective reorganization of a C3a-C3a' linked heterodimer 19 to a single constitutional isomer consistent with the communesin skeleton (Scheme 2).

Scheme 2. Retrosynthetic Analysis of (−)-Communesin F (1)

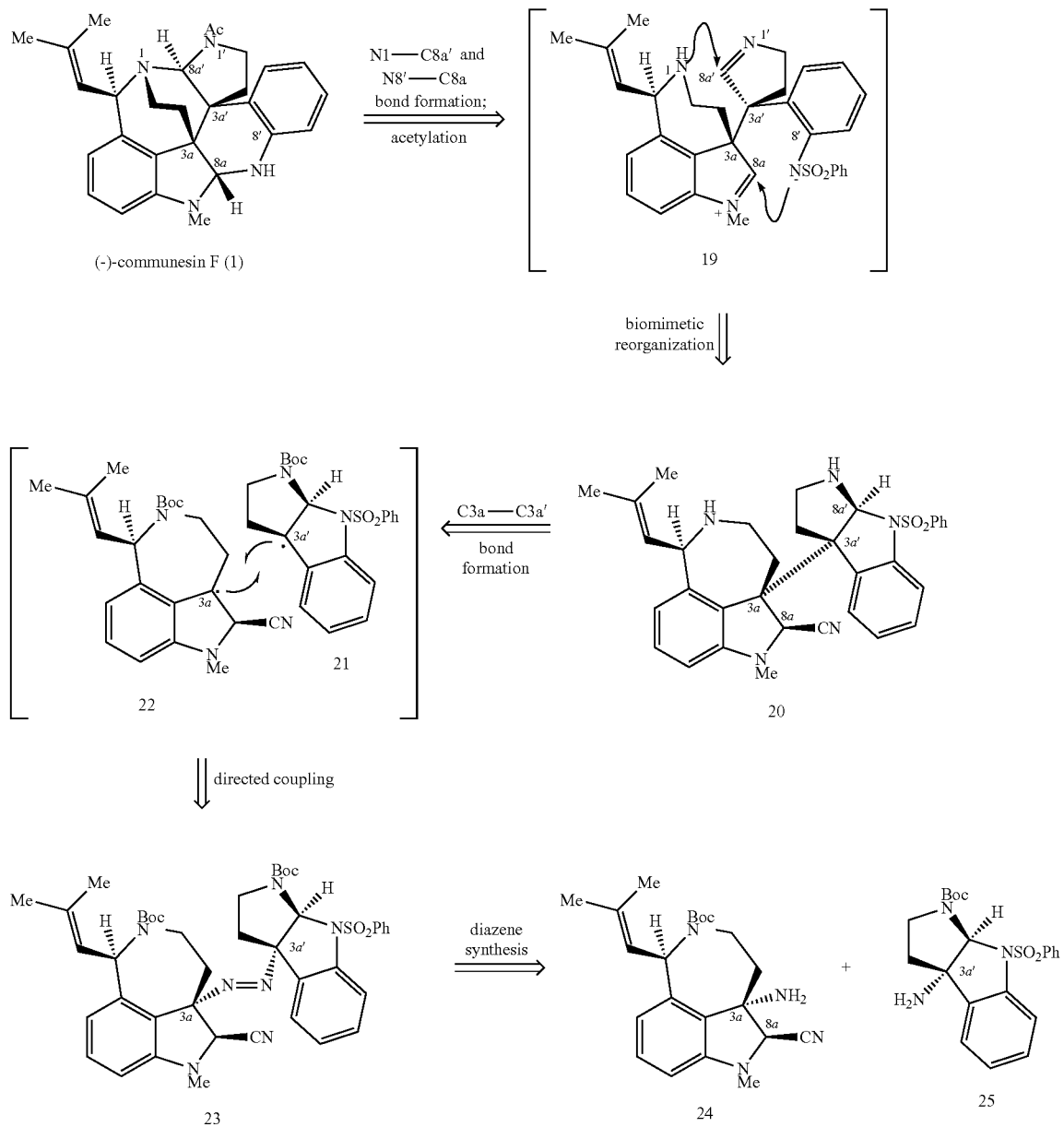

As illustrated in the retrosynthetic analysis of (−)-communesin F (1, Scheme 2), one embodiment of the retrosynthetic design is focused on the efficient assembly and reorganization of a key heterodimeric intermediate 20. We envisioned hexacycle 20 (Scheme 2) to serve as a surrogate for the intermediate 15 (Scheme 1). We anticipated the N8'-sulfonamide would guide the opening of the C8a'-aminal to present the C8a'-imine for N1-addition. Furthermore, we projected the ionization of the C8a-nitrile would offer the C8a-imininium ion needed for aminal formation via N8'-addition. The challenging C3a-C3a' linkage of heterodimer 20 required a directed and stereocontrolled union of a cyclotryptamine fragment 21 and aurantioclavine derivative 22 to simultaneously secure the two critical quaternary stereocenters. Our diazene-based strategy for directed complex fragment assembly provided the essential framework to explore this exciting and convergent approach to (−)-communesin F (1). While we believe the C8a'-stereochemistry of the cyclotryptamine moiety may guide the desired C3a'-stereochemical outcome in this union, the potential level of stereochemical control at C3a during carbon-carbon bond formation was not known. We envisioned the synthesis of complex heterodimeric diazene 23 from tricyclic amines 24 and 25 as tryptamine-surrogates necessary for securing the C3a-C3a' linkage (Scheme 2).

Formula (II) compounds, exemplified by tricyclic indoline 28 (Scheme 3), can be prepared according to the methods described herein and used for the synthesis of compounds of Formula (I), wherein $R^2$, $R^7$, $R^2$, $R^{13}$, n, s, and t are each defined herein. The general strategy and representative examples are highlighted in Schemes 3-5.

Formula (II)

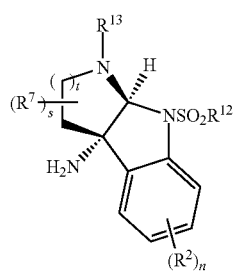

clotryptamine (+)-29 in 93% yield and 96% enantiomeric excess. Significantly, electrophilic activation of the tricyclic bromide (+)-29 in the presence of 2,6-difluorophenylsulfamate provided the desired sulfamate (+)-31 in 63% yield (Scheme 4). The use of 2,6-difluorophenylsulfamate as a nucleophile to trap an intermediate C3a'-electrophile 30 provides a new and expedient route for the directed synthesis of complex diazenes. While this new single-step synthesis of C3a'-sulfamates from the corresponding C3a'-bromides offers a concise solution to the desired precursors, its utility in conversion of the more acid sensitive tert-butyl carbamate substrate 26 to sulfamate 27 gave capricious and inferior outcomes (~50% yield).

Scheme 3. Strategies for Synthesis of Tricycle 28

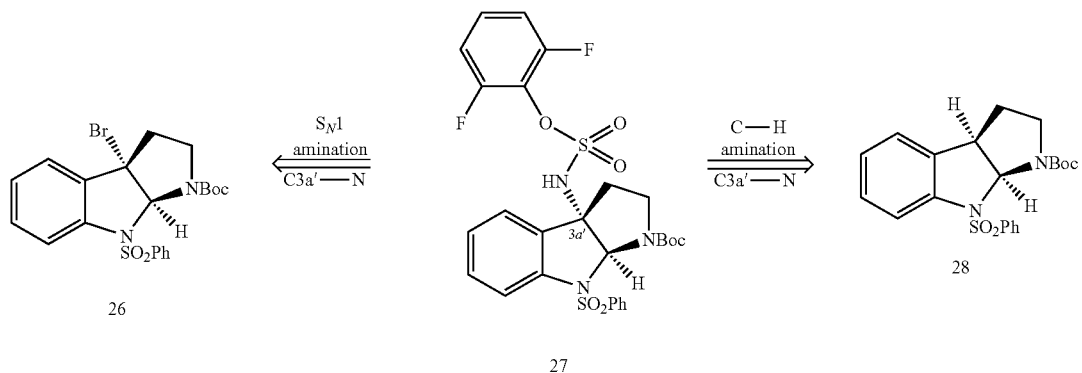

The synthesis of (−)-communesin F (1) commenced with the preparation of the two key tricyclic amines 24 and 25 required for the assembly of critical diazene 23 (Scheme 2). Two approaches to the synthesis of the C3a'-amino cyclotryptamine 25 and the corresponding sulfamate 27 (Scheme 3) were pursued. In the first approach, motivated by the potential for efficient access to enantiomerically enriched C3a'-halocyclotryptamine derivatives, a nucleophilic C3a'-amination (Scheme 4) was used. The second approach to amine 25 relied on Du Bois amination (Roizen, J. L.; Zalatan, D. N.; Du Bois, J. Angew. Chem. Int. Ed. 2013, 52, 11343) of cyclotryptamine 28 to secure the sulfamate 27 (Scheme 5).

One of skill in the art will appreciate that by selection of appropriately substituted starting materials, other cyclotryptamine compounds of Formula (II) can be prepared by analogous methods.

Given the versatility of cyclotryptamine-sulfamates as precursors to the corresponding mixed sulfamides, an efficient synthesis was developed to access sulfamate (+)-31 and related derivatives starting with C3a'-bromo-cyclotryptamine (+)-29 (Scheme 4). Enantioselective bromocyclization of $N_\beta$-Cbz-N1-benzenesulfonyl-tryptamine catalyzed by (S)-3,3'-bis(2,4,6-triisopropyl-phenyl)-1,1'-binaphthyl-2,2'-diyl hydrogenphosphate (TRIP) afforded C3a'-bromocy- Scheme 4. Concise Synthesis of Sulfamate (+)-31$^a$

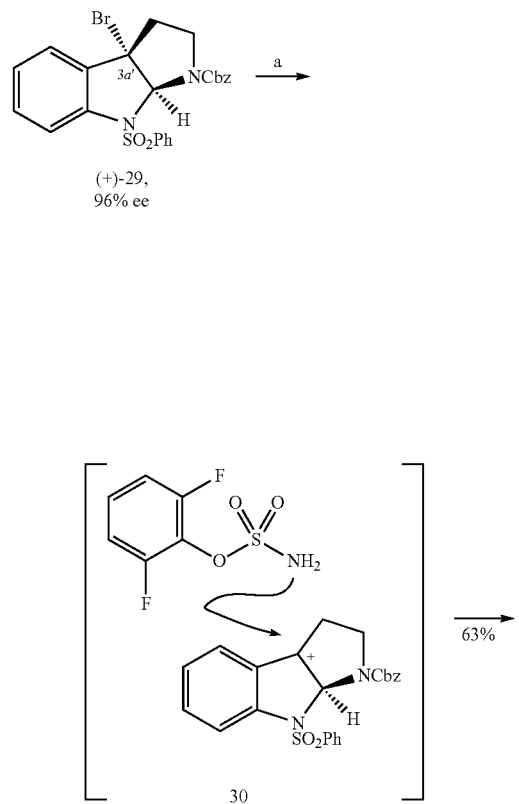

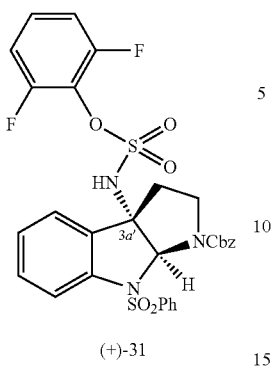

(+)-31

<sup>a</sup>Reagents and conditions: (a) AgSbF$_6$, 2,6-di-tert-butyl-4-methylpyridine, 2,6-difluorophenylsulfamate, CH$_2$Cl$_2$, 23° C., 63%

An alternate approach for the synthesis of tert-butylcarbamate derivative 27 relied on the C—H amination chemistry illustrated in Scheme 5. Mild reduction of bromocyclotryptophan (+)-32 provided the desired C3a'-H cyclotryptophan (+)-33 in 95% yield. Subsequent decarboxylation furnished cyclotryptamine (+)-28 in 69% yield. Under optimal conditions, a R$_h$-catalyzed C—H amination of cyclotryptamine (+)-28 afforded the desired sulfamate (+)-27 in 39% yield after recrystallization. This three-step sequence efficiently generated gram quantities of (+)-27 from the readily available bromocyclotryptophan (+)-32 as an activated form of C3a'-aminocyclotryptamine 25 (Scheme 2) that is ready for coupling with tricyclic amine 24 for diazene synthesis.

Scheme 5. Gram-scale Synthesis of Sulfamate (+)-27<sup>a</sup>

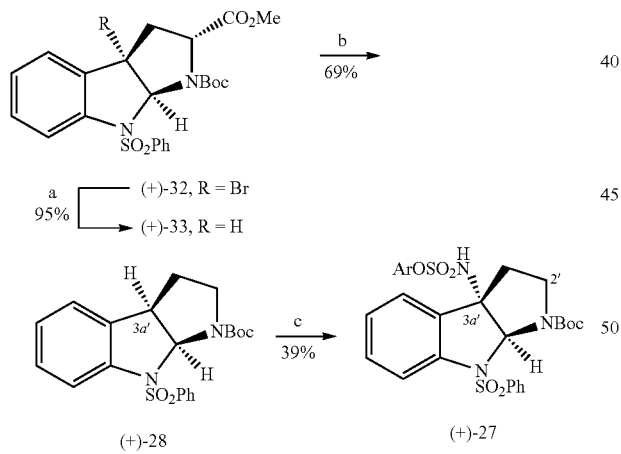

<sup>a</sup>Reagents and conditions: (a) (Me$_3$Si)$_3$SiH, Et$_3$B, air, 23° C., >99:1 dr;
(b) (i) KOH (aq.), MeOH, CH$_2$Cl$_2$, 23° C., (ii) N,N,N',N'-tetramethylchloroformamidinium hexafluorophosphate, thiopyridine N-oxide, 4-(N,N-dimethylamino)pyridine, Et$_3$N, THF; t-BuSH, hv, 23° C.; (c) Rh$_2$(esp)$_2$, H$_2$NSO$_3$Ar, PhI(OAc)$_2$, Ph(CH$_3$)$_2$CCO$_2$H, MgO, 5 Å-MS, i-PrOAc, 23° C., Ar = 2,6-difluorobenzene.

Compounds of Formula (III), exemplified by 24 (Scheme 6) can be prepared according to the methods described herein and used for the synthesis of compounds of Formula (I), wherein R$_4$, R$^5$, R$^6$, R$^8$, R$^{13}$, R$^{14}$, m, r, and u are each defined herein. The general strategy and representative examples are found in Schemes 6-8.

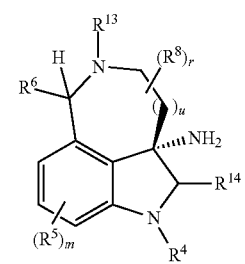

Formula (III)

Scheme 6. Strategies for Synthesis of Tricycle 24

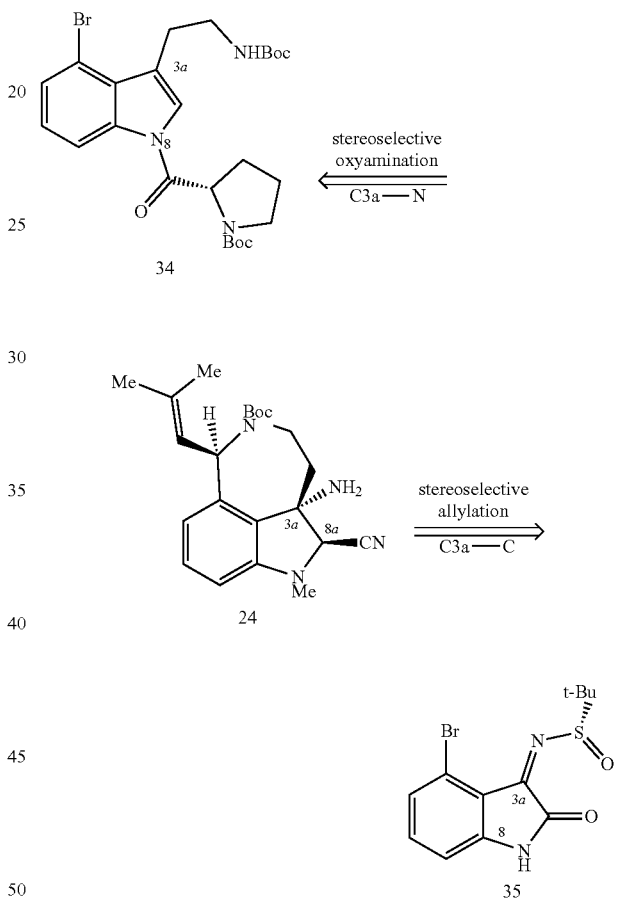

The synthesis of a derivative needed to mimic fragment 22, necessary for the disclosed approach to (−)-communesin F (1), is not known. Accordingly, the present inventors developed an enantioselective synthesis of a tricyclic intermediate that would allow for implementation of our synthetic strategy (Scheme 2). The tricyclic aminonitrile 24 offered the necessary C3a-amine for diazene synthesis and the C2-aminonitrile to allow for mild generation of the corresponding C2-iminium ion needed for aminal synthesis. Two strategies were developed to access the key intermediate 24 as illustrated in Scheme 6. The first strategy involved tryptamine 34 as the substrate for the application of Yoon's oxyamination chemistry, while the second strategy utilized tert-butyl sulfinimine 35 and Ellman's asymmetric allylation of such substrates.

Scheme 7. Oxyamination Approach to Tricycle (+)-24[a]

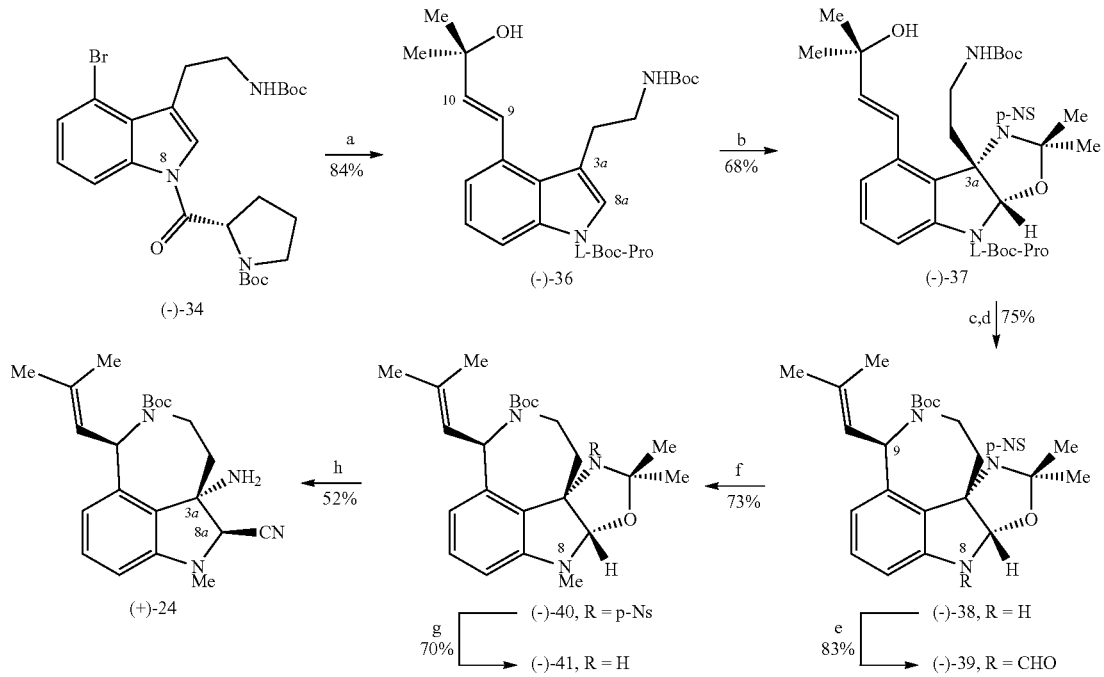

[a]Reagents and conditions: (a) 1,1-dimethylallyl alcohol, Pd(OAc)$_2$, P(o-tol)$_3$, Et$_3$N, MeCN, 95° C.; (b) 3.3-dimethyl-2-(p-nitrobenzenesulfonyl)-1,2-oxaziridine, CuCl$_2$, n-Bu$_4$NCl, CHCl$_3$, 21° C., 89:11 dr; (c) PdCl$_2$(MeCN)$_2$, MeCN, 82° C.; (d) (i) i-Bu$_2$AlH, THF, 0° C., (ii) 1,8-diazabicyclo[5.4.0]undec-7-ene, MeOH, 21° C.; (e) Ac$_2$O, HCO$_2$H, pyridine, CH$_2$Cl$_2$, 21° C.; (f) NaBH$_4$, TFA, THF, 0° C.; (g) PhSH, K$_2$CO$_3$, DMF, 50° C.; (h) Me$_3$SiCN,(F$_3$C)$_2$CHOH, H$_2$O, 21° C.; p-Ns = para-nitrobenzenesulfonyl.

The oxyamination route to aminonitrile 24 commenced with a Mizoroki-Heck reaction of bromoindole (−)-34 with 1,1-dimethylallyl alcohol to provide allylic alcohol (−)-36. Despite early reservations regarding possible competing C9-C10-oxyamination of vinyl indole (−)-36 in place of the desired C3a-C8a-oxyamination, higher levels of diastereoselection for the oxyamination of the more advanced substrate (−)-36 (Scheme 7) were observed. The use of stoichiometric copper(II) chloride facilitated the reaction and gave oxazoline (−)-37 in 68% yield (89:11 dr). Treatment of alcohol (−)-37 with bis(acetonitrile)dichloropalladium(II) in acetonitrile to form the desired azepane (85% yield) followed by removal of the chiral auxiliary (88% yield) provided the desired indoline (−)-38. The formylation of indoline (−)-38 to give formamide (−)-39 (83% yield) followed by mild reduction with sodium borohydride in the presence of trifluoroacetic acid gave the desired N-methylindoline (−)-40 (73% yield). Exposure of sulfonamide (−)-40 to thiophenol and potassium carbonate led to removal of the para-nitrobenzenesulfonyl group and the isolation of the stable oxazolidine (−)-41 in 70% yield. Given the propensity of oxazolidine (−)-41 and aminonitrile (+)-24 toward elimination of the C3a-amino group under strongly acidic or basic conditions, we developed mild hydrolysis conditions to allow for cyanation of a transient C2-hemiaminal leading to aminonitrile (+)-24 in 52% yield in addition to the C2-epimer (26%). While this approach provides flexibility for the late-stage introduction of various N8-substituents and establishes the C3a-stereochemistry, the challenge in unraveling the oxazolidine substructure prompted our investigation of an alternate route to aminonitrile (+)-24 (Scheme 6) involving C3a-C bond formation.

The alternative synthesis of aminonitrile (+)-24 began with the diastereoselective allylation of N8-methyl sulfinimine (−)-42 (Scheme 8) to provide allyl oxindole (+)-43 in 78% yield and with excellent diastereopurity after trituration of the crude addition product with hexane (>98:2 dr). In contrast to the first approach to aminonitrile (+)-24, the placement of the chiral auxiliary on the C3a-substituent enabled the use of the N8-methyl variant of sulfinimine 35 (Scheme 6). Ozonolysis of alkene (+)-43 followed by a reductive work-up afforded the primary alcohol (+)-44 in 79% yield. The alcohol (+)-44 was then converted to tert-butyl carbamate (+)-45 in 82% yield via a Mitsunobu displacement and subsequent in situ desulfonylation. The allylic alcohol needed for synthesis of the azepane substructure was introduced via a Stille vinylation to furnish allylic alcohol (−)-46 in 88% yield. A palladium-catalyzed allylic amination provided azepane (−)-47 in 81% yield as a single diastereomer. The stereochemistry at C3a and C9 of azepane (−)-47 was confirmed unambiguously through analysis of the crystal structure of the corresponding amine (+)-48 (Scheme 8).

Conditions for the mild and efficient conversion of oxindole (−)-47 to the desired aminonitrile (+)-24 were then developed. Partial reduction of oxindole (−)-47 with lithium borohydride afforded a mixture of C2-hemiaminal diastereomers that were too labile for isolation. Direct treatment of the crude hemiaminal with trimethylsilyl cyanide in hexafluoroisopropanol furnished the desired aminonitrile (+)-49 in 60% yield and the easily separable minor C2-epimer (30%). Methanolysis of the tert-butyl sulfinamide (+)-49 provided the desired amino-azepane (+)-24 in 64% yield. The C2-aminonitrile proved to be an ideal trigger for late stage hemiaminal formation while providing adequate stability for the implementation of an efficient fragment assembly. We anticipate future adaptation of this robust synthetic route to other N8-variants of azepane (+)-24 via judicious N8-substitution of sulfinimine 35.

Compounds of Formula (V) represented by heterodimer (+)-51 can be prepared according to the methods described herein, and used for the synthesis of compounds of Formula (I), wherein $R^4$, $R^5$, $R^6$, $R^8$, $R^{12}$, $R^{13}$, $R^{14}$, m, n, r, s, t and u are each defined herein.

Formula (V)

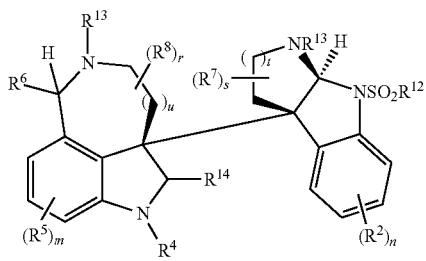

After developing versatile syntheses of both essential fragments, the union of azepane (+)-24 and cyclotryptamine (+)-27 was then examined to introduce the critical C3a-C3a' bond. Dissolution of the two fragments in tetrahydrofuran in the presence of 4-(N,N-dimethylamino)pyridine afforded sulfamide (+)-50 in 80% yield on gram-scale (Scheme 9). The oxidation of sterically shielded sulfamides containing electron-rich arenes, such as the N-methyl aniline substructure of sulfamide (+)-50, suffers from competitive arene-halogenation. After extensive experimentation, the unique ability of tertiary N-chloroamides to affect chemoselective oxidation of sulfamide (+)-50 to the corresponding diazene (Scheme 9) without competitive arene-halogenation was discovered. Exposure of sulfamide (+)-50 to N-chloro-N-methylbenzamide (6 equiv) in conjunction with polystyrene-bound 2-tert-butylimino-2-diethylamino-1,3-dimethyl-perhydro-1,3,2-diazaphosphorine (BEMP) in methanol provided the desired diazene (+)-23 in 57% yield. Photoexcitation and expulsion of dinitrogen from a thin film of diazene (+)-23, followed by radical combination of the resulting cyclotryptamine 21 and azepane 22 (Scheme 2), afforded the desired heterodimer (+)-51 in 39% yield as a single diastereomer. The remarkable diastereoselection at C3a of heterodimer (+)-51 is notable and may be due to the confluence of a rapid radical combination step and the additional stereoinduction imposed by the C2-nitrile. Importantly, this diazene-based strategy for directed complex fragment assembly allowed for the stereoselective construction of the critical C3a-C3a' linkage, securing the corresponding vicinal quaternary stereocenters.

Scheme 9. Directed Synthesis of Heterodimer (+)-51.[a]

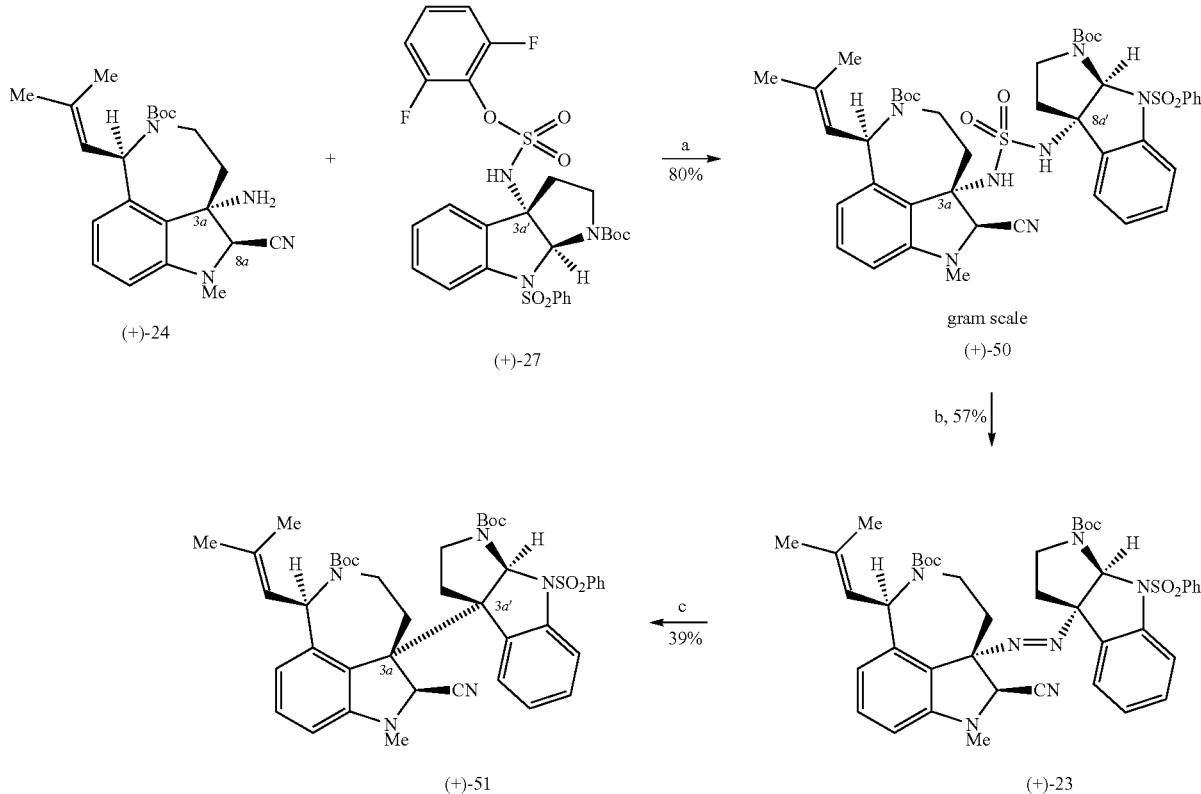

[a]Reagents and conditions: (a) 4-(N,N-dimethylamino)pyridine, THF, 23° C.; (b) polystyrene-2-t-butylimino-2-diethylamino-1,3-dimethyl-perhydro-1,3,2-diazaphosphorine, N-chloro-N-methylbenzamide, MeOH, 23° C.; (c) hν (350 nm), 25° C.

Transient intermediates of Formula (IV), represented by (−)-52, can be prepared according to the methods described herein and subsequently converted to compounds of Formula (I), wherein $R^1$-$R^8$, $R^{12}$, $R^{13}$, m, n, r, s, t, and u are each defined herein.

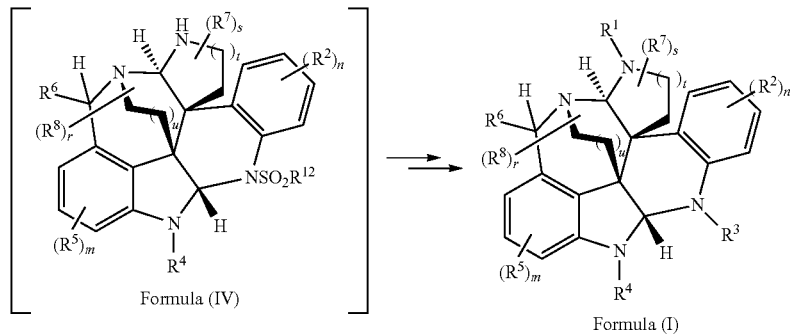

Formula (IV) → Formula (I)

The reaction conditions for the planned transformation of (+)-51 were carefully selected due to the sensitive nature of the C3a-C3a' linkage. It was thought that an appropriate sequence of amine unveiling would maximize efficiency for the desired aminal exchange, and that unveiling the N1- and N1'-amines of heterodimer (+)-51 would allow opening of the C8a' aminal with the benzenesulfonamide as the leaving group, thus allowing rapid trapping of the C8a'-imine of intermediate 19 en route to heptacycle 52.

Treatment of heterodimer (+)-51 with scandium trifluoromethanesulfonate in trifluoroethanol provided the desired heterodimer (+)-20 by selective removal of the tert-butyl carbamates while preserving the sensitive C8a-aminonitrile (Scheme 10). The electron-withdrawing N8'-sulfonamide permitted an examination of basic conditions to selectively open the cyclotryptamine substructure. Treatment of heterodimer (+)-20 with lithium tert-butoxide in methanol provided clean and complete conversion to the desired heptacyclic structure 52 within 1 h at 50° C. as observed by in situ $^1$H-NMR spectroscopy. Significantly, only the desired heptacycle 52 was formed in preference to other constitutional isomers. Methanol was found to be an excellent solvent for this transformation, possibly due to its ability to stabilize reactive intermediates as the corresponding O-alkyl-hemiaminals. It was found that other groups such as OH, $OC_{1-4}$ alkyl (e.g., OMe) or $P(O)(OEt)_2$ can be used in place of C8a-CN, thereby improving flexibility. Although intermediate 52 could be observed by in situ $^1$H NMR spectroscopy, this compound did not show sufficient stability for isolation. This may be due to the sensitive nature of the C8a'-aminal of heptacycle 52, which upon reversible opening to the C8a'-imine increases the lability of the C3a-C3a' bond. As an indication of the sensitivity of the C3a-C3a' linkage of heterodimer (+)-20, simple heating of a derivative (C8a-OMe instead of C8a-CN) in acetonitrile-$d_3$ at 80° C. predominantly led to fragmentation. Treatment of the basic solution of heptacycle 52 with pyridinium p-toluenesulfonate to quench the alkoxides, followed by addition of acetic anhydride afforded the N1'-acetyl derivative (−)-53 in 82% overall yield. A final-step unveiling of the N8'-amine was accomplished by treatment of (−)-53 with sodium amalgam to provide (−)-communesin F (1) in 83% yield. All $^1$H and $^{13}$C NMR data as well as optical rotation (observed $[\alpha]_D^{24}$=−249, c=0.13, $CHCl_3$; literature $[\alpha]_D^{20}$=−264, c=0.34, $CHCl_3$), for our synthetic (−)-communesin F (1) were in agreement with literature data.

Scheme 10. Synthesis of (-)-Communesin F (1) via a Biogenetically Inspired Final Stage Reorganization

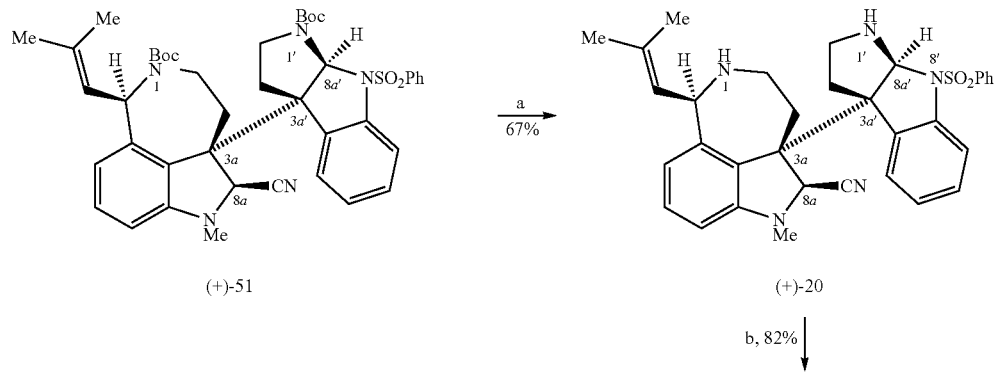

(+)-51 → (+)-20 a, 67% b, 82%

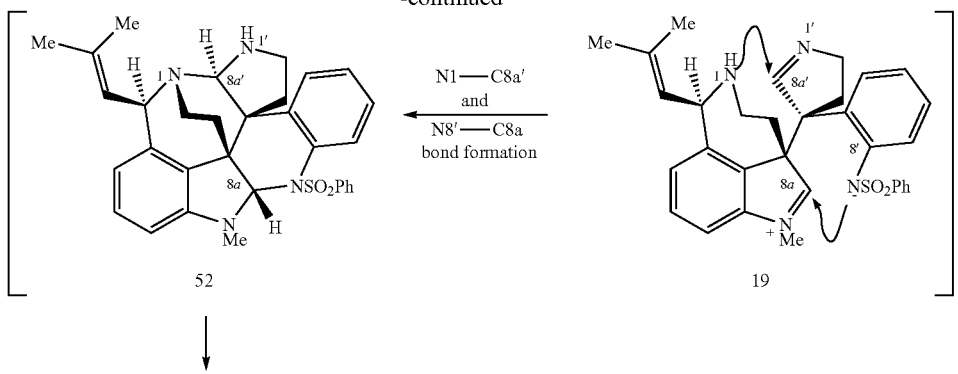

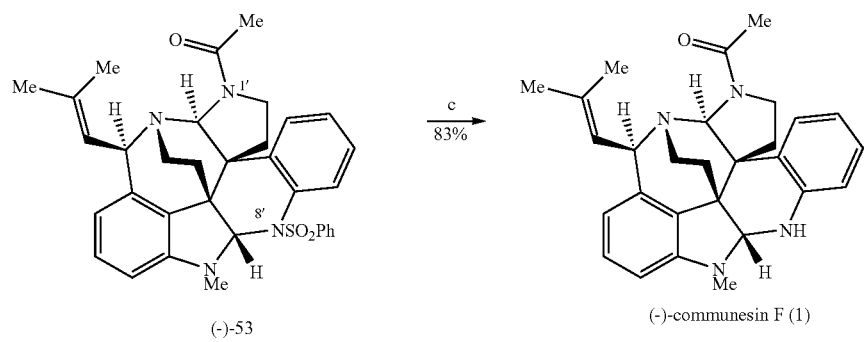

*Reagents and conditions: (a) Sc(OTf)$_3$, F$_3$CCH$_2$OH, 23° C.; (b) t-BuOLi, MeOH, 50° C.; dry PPTS, Ac$_2$O, 23° C.; (c) Na(Hg), NaH$_2$PO$_4$, THF, MeOH, 23° C.

Scheme 11 summarizes a representative strategy for assembling members of the communesin family and other analogs where the substituents at R$^1$, R$^4$, and R$^6$ are sensitive groups incompatible with the methods described above. Several modifications have been implemented. For instance, in the presence of acid-sensitive moieties, N-Cbz can replace N-Boc (Scheme 11, R$^{13}$), so that the conversion of a Formula (V) to Formula (IX) can be carried out with a mild reagent such as Pd(OH)$_2$/C that is well-suited for the complex environment. Similarly, the —SO$_2$Ph group utilized in the (−)-Communesin F total synthesis could be replaced with the SES-protecting group shown in Formula (VIII) to avoid the deleterious effects of Na/Hg in the final step towards the desired Formula (I) compounds. Accordingly, a number of previously unobtainable communesin analogs are now within reach, based on the newly developed synthesis described below.

Scheme 11. General Scheme for the Synthesis of Communesins and Analogs that Possess Sensitive Functionality at R$^1$ and R$^6$.

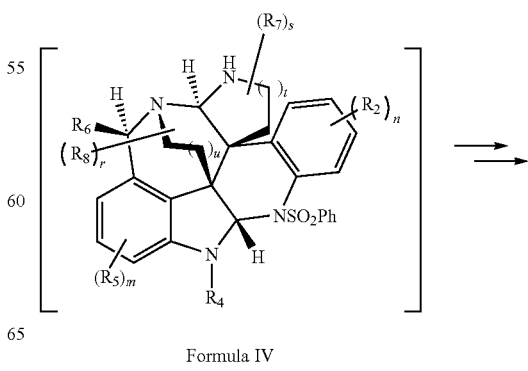

Formula IV

-continued

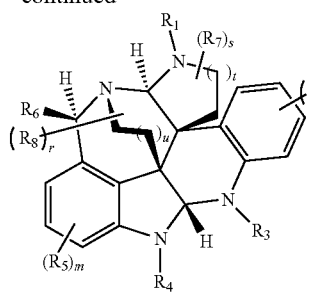

Formula I

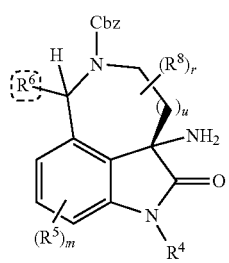

Formula (III)

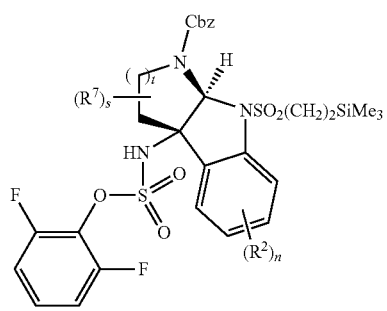

Formula (VIII)

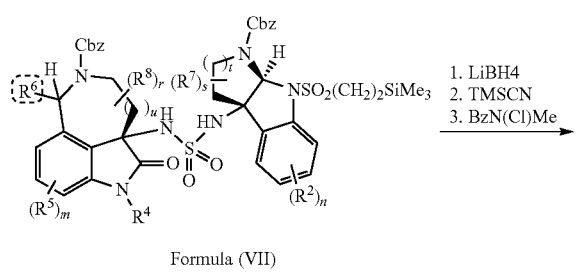

Formula (VII)

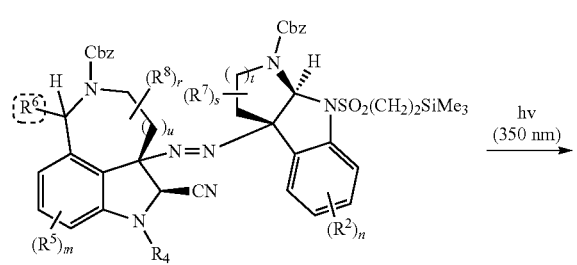

Formula (VI)

-continued

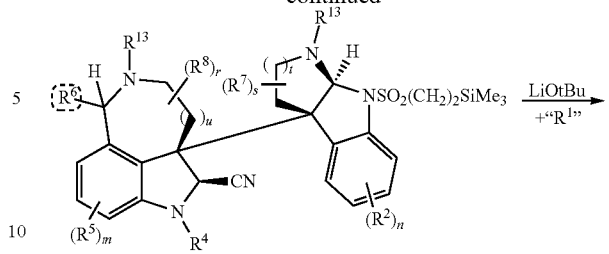

Pd(OH)$_2$/C ⟶ Formula (V) (R$^{13}$ = CBz)
Formula (IX) (R$^{13}$ = H)

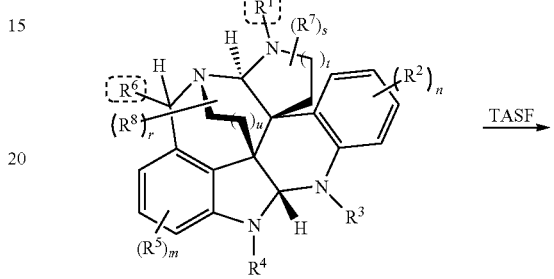

Formula (I)

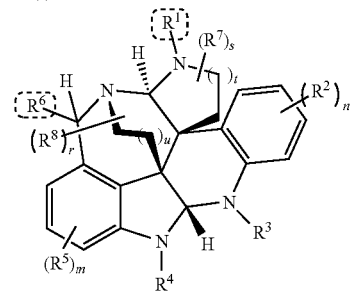

Formula (I)
(R$^3$ = H)

Appendix 1 of U.S. Provisional Application No. 62/334,826, incorporated by reference herein, provides Supporting Information including experimental procedures, spectroscopic data, crystal structure of (+)-48 (CIF), and copies of NMR spectra. Color representations of some of the above figures, formulas, and schemes, as well as color representations of selected information from Appendix 1 are included in the attached color drawings.

In various embodiments, a highly convergent enantioselective total synthesis of (−)-communesin F (1) with late-stage chemistry that parallels the latest insights and hypotheses concerning the biogenesis of these alkaloids is described. This synthesis involves the union of fragments (+)-24 and (+)-27 to provide complex sulfamide (+)-50 on gram-scale. This advanced intermediate is converted to alkaloid (−)-1 in only five additional steps (Schemes 9 and 10) which include the application of our diazene-directed fragment assembly strategy to secure the congested C3a-C3a' linkage, and a guided biomimetic rearrangement to selectively provide the heptacyclic core of these alkaloids. Highlights of our synthesis include an efficient cyclotryptamine-C3a-sulfamate synthesis by either a new silver-promoted nucleophilic amination or rhodium-catalyzed C—H amination protocol, application of catalytic asymmetric halocyclization and diastereoselective oxyamination reactions in complex settings, a stereoselective sulfinimine allylation, and efficient assembly and utility of a richly functional diazene for complex fragment coupling. The successful implementation of this synthetic strategy and the versatile synthesis of the fragments, along with a final stage acylation of the communesin core provide a foundation for a unified synthetic route to access structurally related complex alkaloids and derivatives. Such derivatives can be used in therapy or as probes or tools for mechanistic investigations. A person of skill in the art will appreciate that by appropriate selection of starting materials, reagents, and reaction conditions, the schemes provided herein can be modified to provide analogs or derivatives of (−)-communesin according to Formula (I).

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

In addition, those of ordinary skill in the art recognize that some functional groups can be protected/deprotected using various protecting groups before a certain reaction takes place. Suitable conditions for protecting and/or deprotecting specific functional group, and the use of protecting groups are well-known in the art.

For example, various kinds of protecting groups are described in T. W. Greene and G. M. Wuts, Protecting Groups in Organic Synthesis, Second edition, Wiley, New York, 1991, and other references cited above.

All documents cited herein are herein incorporated by reference in their entirety for all purposes.

Using the methods described herein, various derivatives of communesins can be prepared from the appropriate starting materials and intermediates using the general methods described herein, as shown below in Scheme 12:

Scheme 12. Representative Classes of Communesin Derivatives.

C10-epoxide:

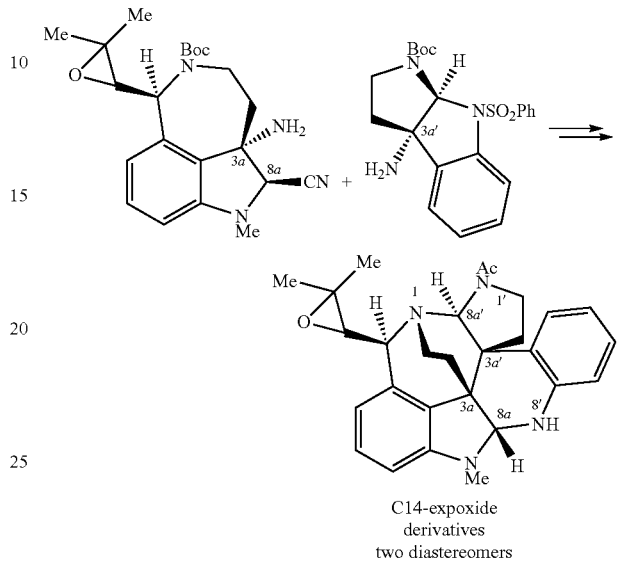

C14-expoxide derivatives
two diastereomers

C10-derivatives:

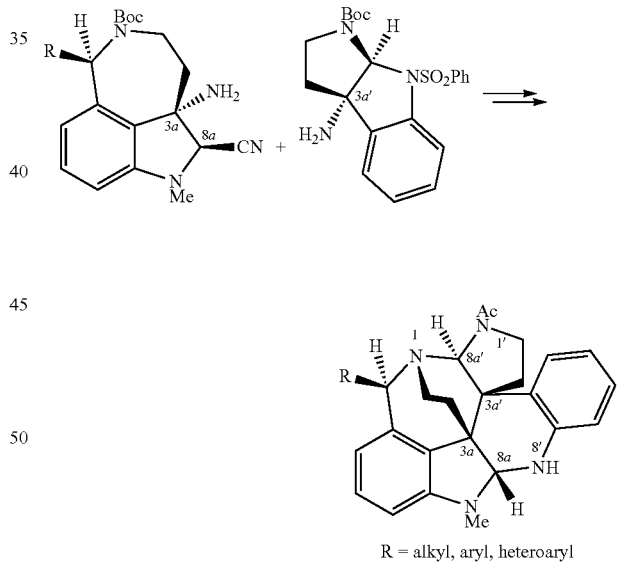

R = alkyl, aryl, heteroaryl arene-derivatives:

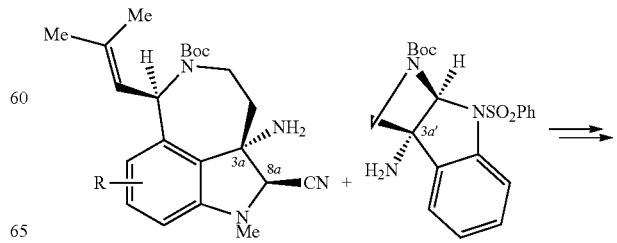

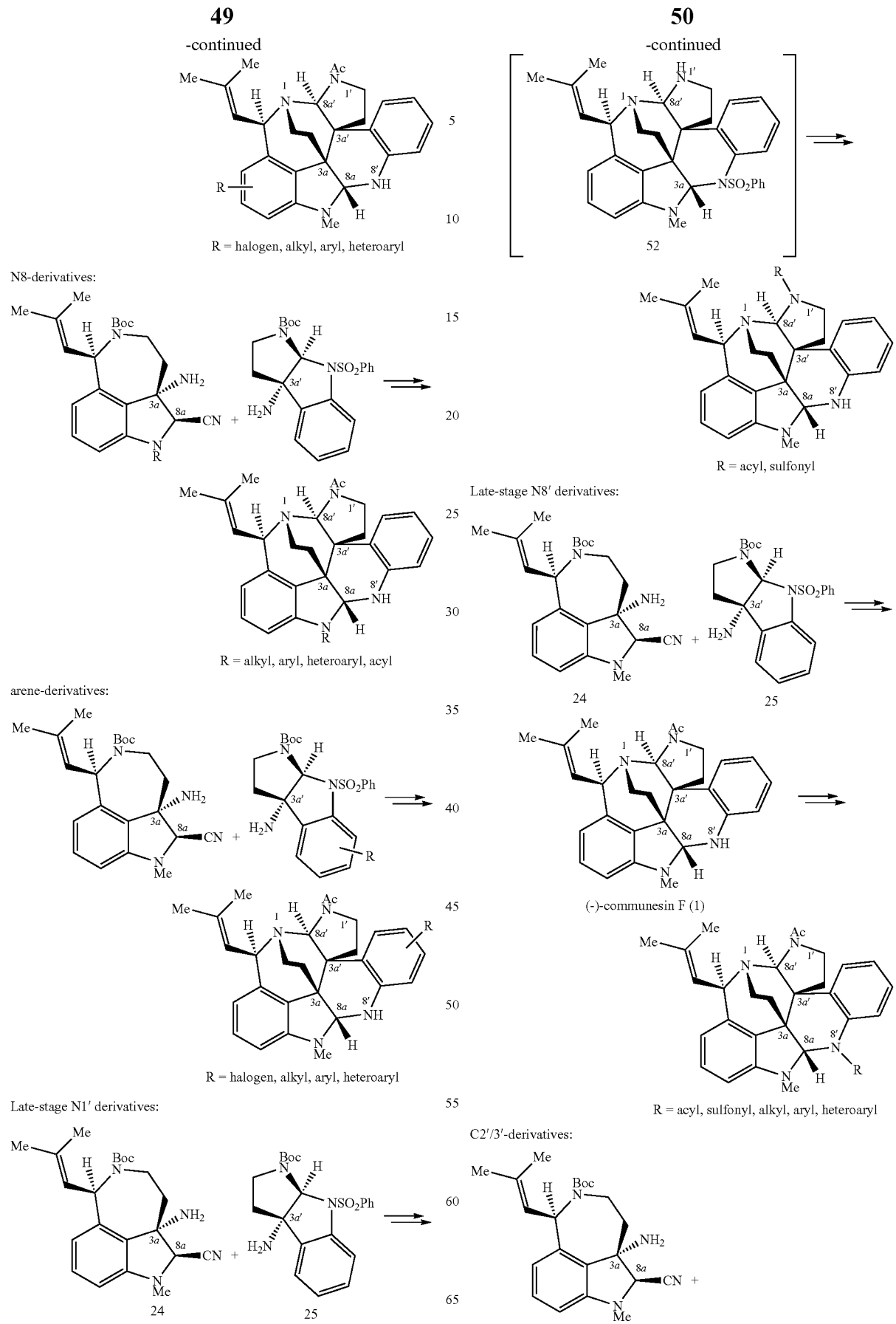

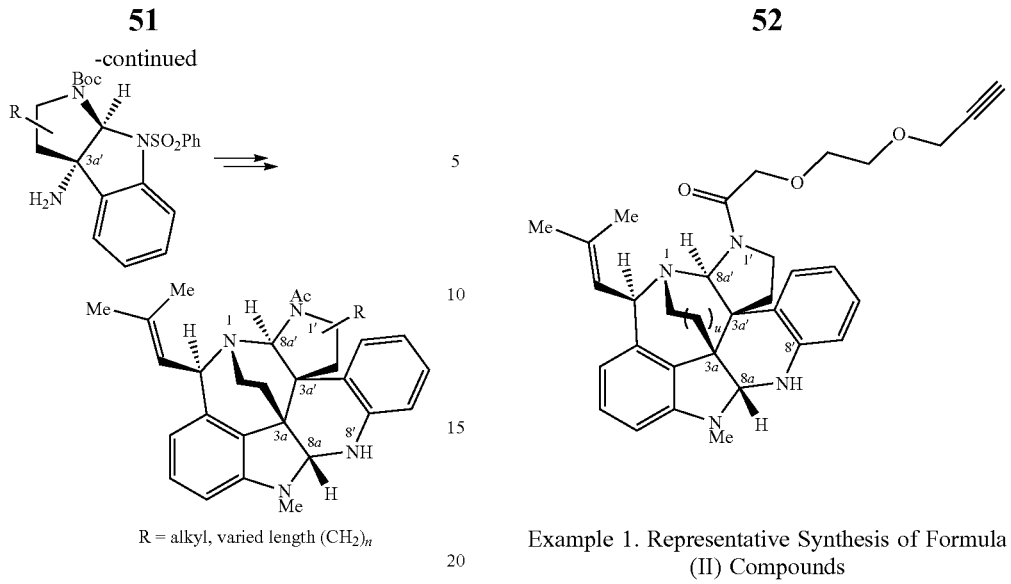

R = alkyl, varied length (CH$_2$)$_n$

C2/3-derivatives:

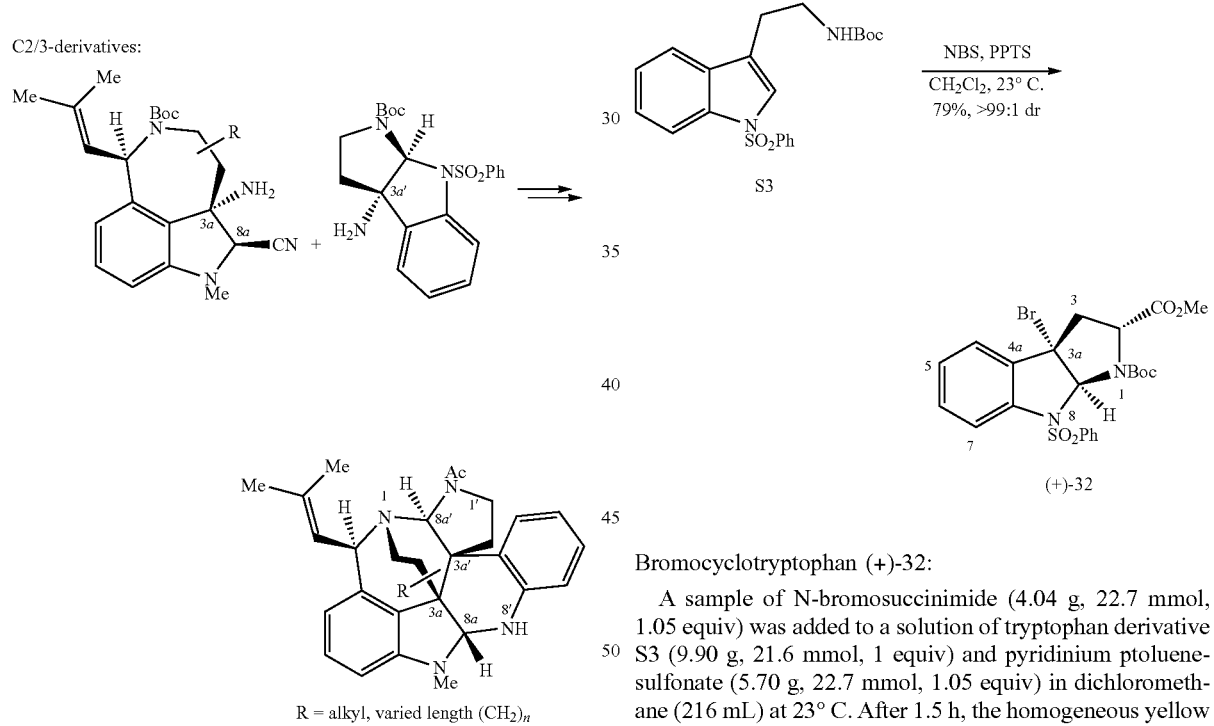

R = alkyl, varied length (CH$_2$)$_n$

The skilled artisan will also recognize that the particular variations in substitution of the communesin structure illustrated above in Scheme 12 can be combined. For example, substitution at C10 as described above can be combined with substitution at C2/3, and/or C2'/3' and/or N8, etc. These modifications can be evaluated to identify derivatives with enhanced potency for particular indications, as mechanistic probes, or for use in targeted therapy. For example, a modification as shown below can provide a "functional handle" for conjugation with an antibody (targeted delivery), for use in pull-down experiments, or as a means to attach an affinity tag or fluorophore (probe):

Example 1. Representative Synthesis of Formula (II) Compounds

Bromocyclotryptophan (+)-32:

A sample of N-bromosuccinimide (4.04 g, 22.7 mmol, 1.05 equiv) was added to a solution of tryptophan derivative S3 (9.90 g, 21.6 mmol, 1 equiv) and pyridinium ptoluenesulfonate (5.70 g, 22.7 mmol, 1.05 equiv) in dichloromethane (216 mL) at 23° C. After 1.5 h, the homogeneous yellow reaction mixture was washed sequentially with a saturated aqueous sodium bicarbonate solution (100 mL) followed by a saturated aqueous sodium thiosulfate solution (100 mL), and finally saturated aqueous sodium chloride solution (100 mL). The organic layer was dried over anhydrous sodium sulfate, was filtered, and was concentrated under reduced pressure. The resulting residue was purified by flash column chromatography on silica gel (eluent: 50% diethyl ether in hexanes) to afford bromocyclotryptophan (+)-32 (11.6 g, 99.6%, 17.5:1 dr) as a white foam. The diastereomeric ratio was further enriched by recrystallization from 27% ethyl acetate in hexanes to yield bromocyclotryptophan (+)-32 (9.13 g over two batches, 78.7%, >99:1 dr) as colorless plates.

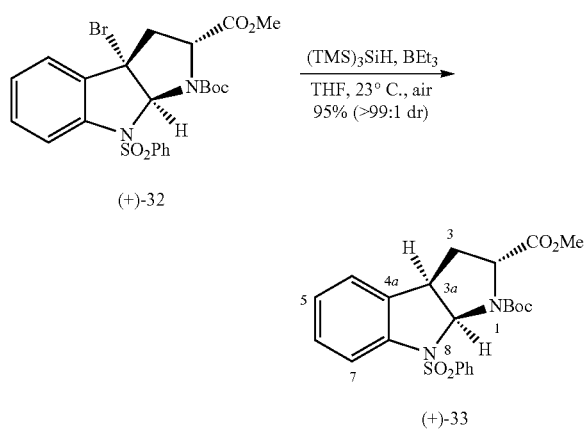

(+)-32

(+)-33

Cyclotryptophan (+)-33:

Triethylborane (1.0 M in THF, 1.7 mL, 1.7 mmol, 0.10 equiv) was added via syringe to a solution of bromocyclotryptophan (+)-32 (9.01 g, 16.7 mmol, 1 equiv) and tris(trimethylsilyl)silane (15.5 mL, 50.1 mmol, 3.00 equiv) in tetrahydrofuran (129 mL) at 23° C. under an air atmosphere. After 10 min, the homogeneous colorless solution was diluted with a saturated aqueous sodium bicarbonate solution (130 mL). After vigorous stirring for 10 min, the heterogeneous biphasic mixture was diluted with deionized water (100 mL) then extracted with dichloromethane (3×200 mL). The combined organic extracts were dried over anhydrous sodium sulfate, were filtered, and were concentrated under reduced pressure to yield a colorless semi-solid suspended in a colorless oil. The colorless oil was decanted and the remaining residue was purified via flash chromatography on silica gel (eluent: 25%→32% ethyl acetate in hexanes) to afford cyclotryptophan (+)-33 (7.27 g, 94.9%, >99:1 dr) as a white foam.

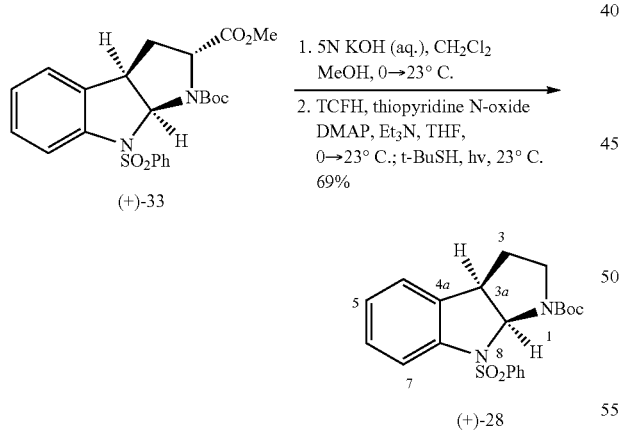

(+)-33

(+)-28

Cyclotryptamine (+)-28:

An aqueous sodium hydroxide solution (5 N, 79.0 mL, 395 mmol, 25.0 equiv) was added in portions over 5 min to a solution of cyclotryptophan (+)-33 (7.25 g, 15.7 mmol, 1 equiv) in methanol (240 mL) and dichloromethane (31 mL) cooled to 0° C. in an ice bath under an air atmosphere. After 5 min, the ice bath was removed and the milky white solution was allowed to stir at 23° C. After 7 h, the reaction mixture was cooled to 0° C. in an ice bath and acidified to pH~3 by the portionwise addition of an aqueous hydrochloric acid solution (12 N, 34 mL) over 10 min. The resulting white suspension was allowed to warm to 23° C. and was then concentrated under reduced pressure to remove methanol. The white suspension was then diluted with deionized water (100 mL) and extracted with dichloromethane (3×200 mL). The combined organic extracts were washed with a saturated aqueous sodium chloride solution (100 mL), were dried over anhydrous sodium sulfate, were filtered, and were concentrated under reduced pressure to afford the crude carboxylic acid (8.0 g, >99%) as a white foam, which was used directly in the next step after azeotropic drying by concentration from toluene (HPLC grade, 3×100 mL). Samples of 2-mercaptopyridine N-oxide (3.20 g, 25.2 mmol, 1.60 equiv), 4-(dimethylamino)pyridine (192 mg, 1.57 mmol, 0.100 equiv), and N,N,N',N'-tetramethylchloroformamidinium hexafluorophosphate (TCFH, 6.62 g, 23.6 mmol, 1.50 equiv) were added sequentially to a solution of the crude carboxylic acid in tetrahydrofuran (157 mL) cooled to 0° C. in an ice bath. The reaction flask was subsequently removed from the ice bath, covered in aluminum foil, and charged with triethylamine (8.80 mL, 63.0 mmol, 4.00 equiv) in a slow stream over 30 s while the reaction mixture was still cold. After 2.75 h, tert-butyl mercaptan (8.90 mL, 78.7 mmol, 5.00 equiv) was added via syringe. The aluminum foil was then removed from the flask and the resulting green suspension was irradiated with a flood lamp (500 W). To maintain an internal temperature of 23° C., the flask was immersed in a 20° C. water bath. After 2 h, the lamp was shut off and a saturated aqueous sodium bicarbonate-water solution (1:1, 400 mL) was added. The aqueous layer was extracted with dichloromethane (3×200 mL). The combined organic extracts were washed with a saturated aqueous sodium chloride solution (150 mL), were dried over anhydrous sodium sulfate, were filtered, and were concentrated under reduced pressure. The resulting residue was purified by flash column chromatography on silica gel (eluent: 20→25% acetone in hexanes) to afford cyclotryptamine (+)-28 (4.35 g, 69.0% overall from (+)-33) as a white foam.

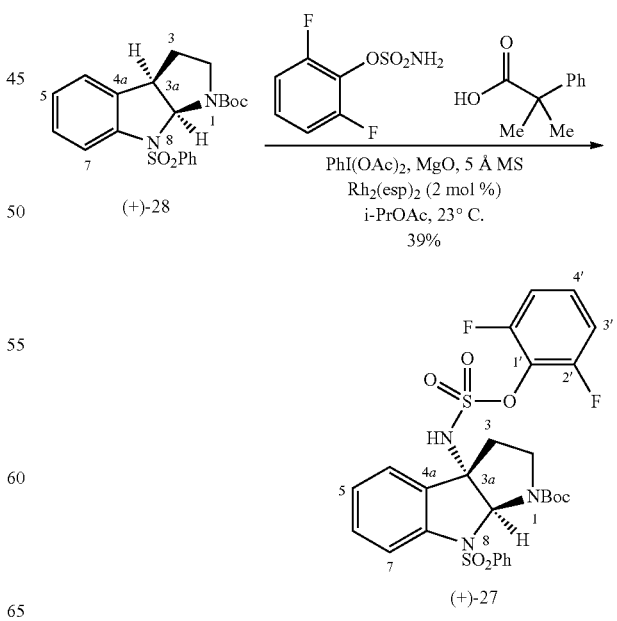

Sulfamate Ester (+)-27:

A round bottom flask equipped with a stir bar was charged with crushed 5 Å molecular sieves (1.06 g, 200 mg/mmol of 28), and magnesium oxide (853 mg, 21.2 mmol, 4.00 equiv). The flask and its contents were flame-dried under vacuum for 7 min. The reaction vessel was allowed to cool to 23° C. and was then backfilled with argon. Bis[rhodium(α,α,α',α'-tetramethyl-1,3-benzenedipropionic acid)] (80.2 mg, 106 µmol, 0.0200 equiv), cyclotryptamine (+)-28 (2.13 g, 5.29 mmol, 1 equiv), 2,6-difluorophenyl sulfamate5 (1.44 g, 6.88 mmol, 1.30 equiv), and 2-methyl-2-phenylpropionic acid (434 mg, 2.65 mmol, 0.500 equiv) were then added sequentially. The flask was evacuated and backfilled with argon (three cycles) and was then charged with isopropyl acetate (7.0 mL). The resulting green suspension was stirred vigorously for 5 min then (diacetoxyiodo) benzene (3.41 g, 10.6 mmol, and 2.00 equiv) was added in a single portion. The flask was sealed and the suspension was allowed to stir vigorously at 23° C. under a static atmosphere of argon. After 26 h, the reaction mixture was filtered through a pad of Celite and the filter cake was rinsed with ethyl acetate (50 mL). The filtrate was concentrated under reduced pressure and the resulting residue was purified by flash column chromatography on silica gel (eluent: 20→30% acetone in hexanes) to afford a mixture of the desired sulfamate ester (+)-27 along with a minor amount of the regioisomeric C2 amination product (5.4:1). The mixture was further purified by recrystallization from dichloromethane, hexanes, and diethyl ether (1:1:1, 4.5 mL) at 5° C. to afford exclusively the sulfamate ester (+)-27 (1.26 g, 39.2%) as an off-white solid.

Example 2: Representative Synthesis of Formula (III) Compounds

Amide (−)-34:

A 100 mL Schlenk flask containing a magnetic stir-bar was charged with 18-crown-6 (5.50 g, 20.8 mmol, 2.00 equiv), potassium fluoride (2.44 g, 41.6 mmol, 4.00 equiv), bromotryptamine S4 (3.53 g, 10.4 mmol, 1 equiv), and L-proline derivative S5 (6.12 g, 18.2 mmol, 1.75 equiv) sequentially.7 The reaction flask and its contents were placed under vacuum and backfilled with argon (three cycles). Acetonitrile (42 mL) and N,N-diisopropylethylamine (6.40 mL, 46.8 mmol, 4.50 equiv) were then added. The resulting bright yellow heterogeneous mixture was sonicated for 1 h and then the flask was immersed in a pre-heated oil bath at 50° C. and stirred vigorously for 16 h. The reaction mixture was concentrated under reduced pressure. The residue was dissolved in ethyl acetate (100 mL) and was washed sequentially with deionized water (50 mL), a saturated aqueous potassium carbonate-water solution (1:1, 2×50 mL), deionized water (50 mL), and a saturated aqueous sodium chloride solution (2×50 mL). The organic phase was dried over anhydrous sodium sulfate, was filtered, and was concentrated under reduced pressure. The resulting light brown oil was purified by flash column chromatography on silica gel (eluent: 10%→40% ethyl acetate in hexanes) to afford amide (−)-34 (5.50 g, 98.6%) as a white foam.

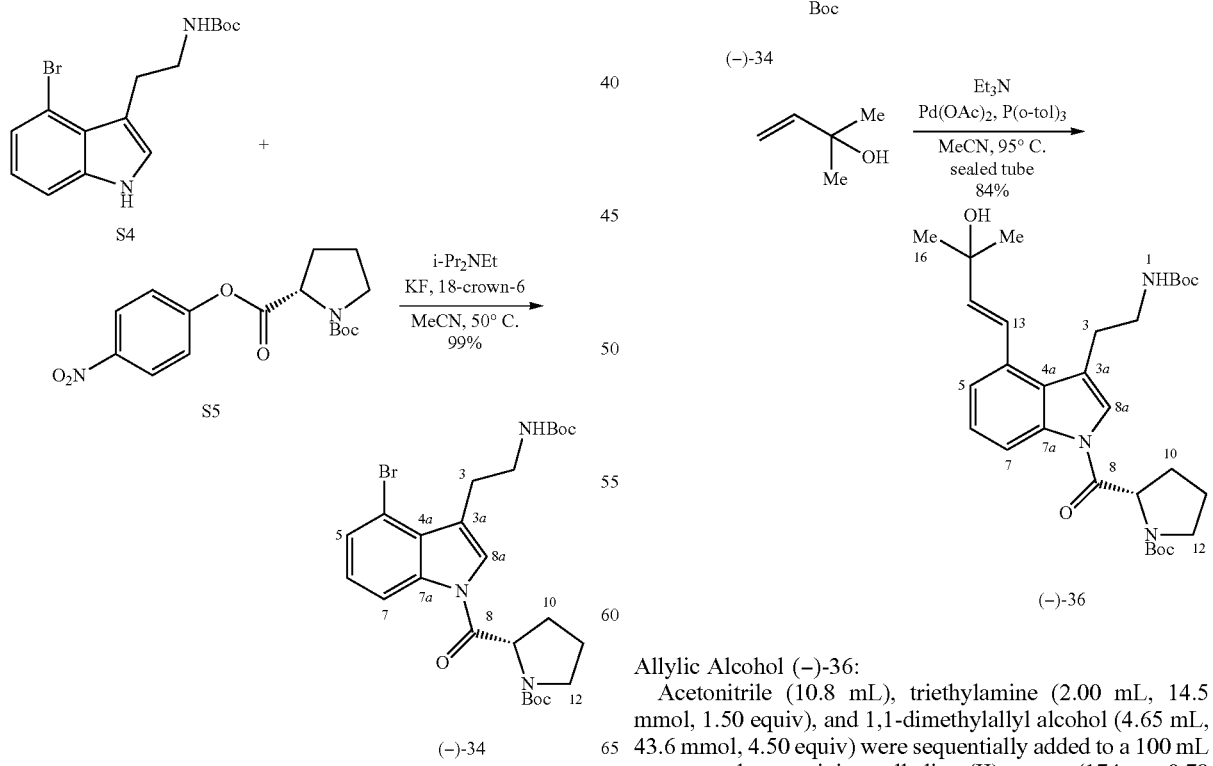

Allylic Alcohol (−)-36:

Acetonitrile (10.8 mL), triethylamine (2.00 mL, 14.5 mmol, 1.50 equiv), and 1,1-dimethylallyl alcohol (4.65 mL, 43.6 mmol, 4.50 equiv) were sequentially added to a 100 mL pressure tube containing palladium(II) acetate (174 mg, 0.78 mmol, 0.0800 equiv), tri(o-tolyl) phosphine (590 mg, 1.94 mmol, 0.200 equiv), and amide (−)-34 (5.20 g, 9.69 mmol, 1 equiv). The reaction tube was sealed under an argon atmosphere and immersed in a pre-heated oil bath at 95° C. After 3.5 h, the reaction mixture was cooled to 23° C. and was filtered through a pad of silica gel. The filter cake was washed with ethyl acetate (100 mL) and the filtrate was concentrated under reduced pressure. The thick orange oil was purified by flash column chromatography on silica gel (eluent: 10%→75% acetone in hexanes). The resulting yellow sticky foam was purified by flash column chromatography on silica gel (eluent: 10%→40% ethyl acetate in hexanes) to afford allylic alcohol (−)-36 (4.40 g, 83.8%) as a white foam.

acetate-hexanes solution (1:1, 800 mL). The yellow filtrate was concentrated under reduced pressure and the residue was purified by flash column chromatography on silica gel (eluent: 10%→40% ethyl acetate in hexanes). Further purification by chromatography on silica gel (eluent: 10%→30% acetone in hexanes) afforded oxazoline (−)-37 (4.16 g, 68.1%) as a pale yellow foam as an inseparable mixture of diastereomers (89:11 dr). The diastereomeric ratio was determined after derivatization of oxazoline (−)-37.

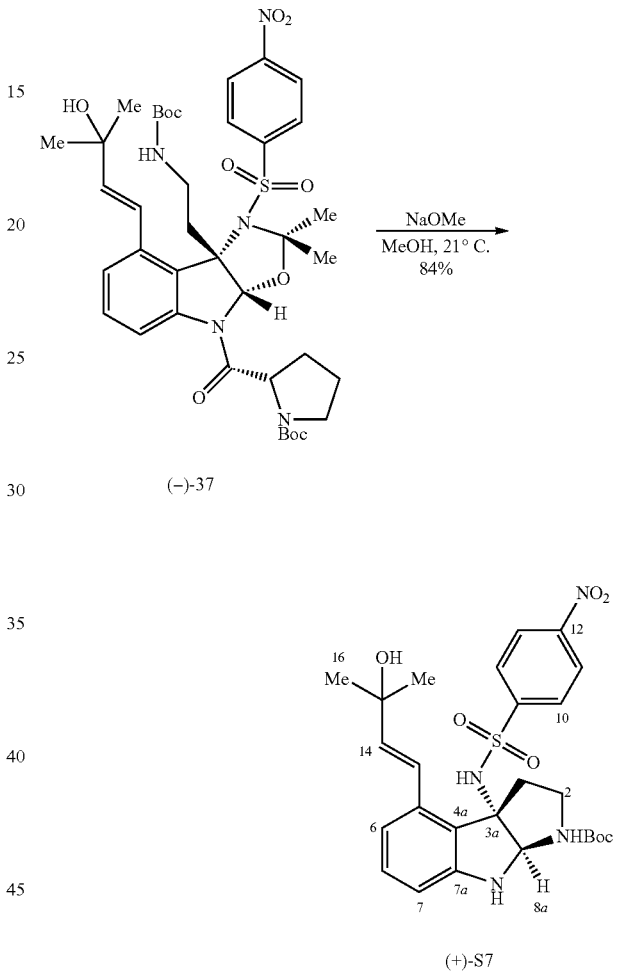

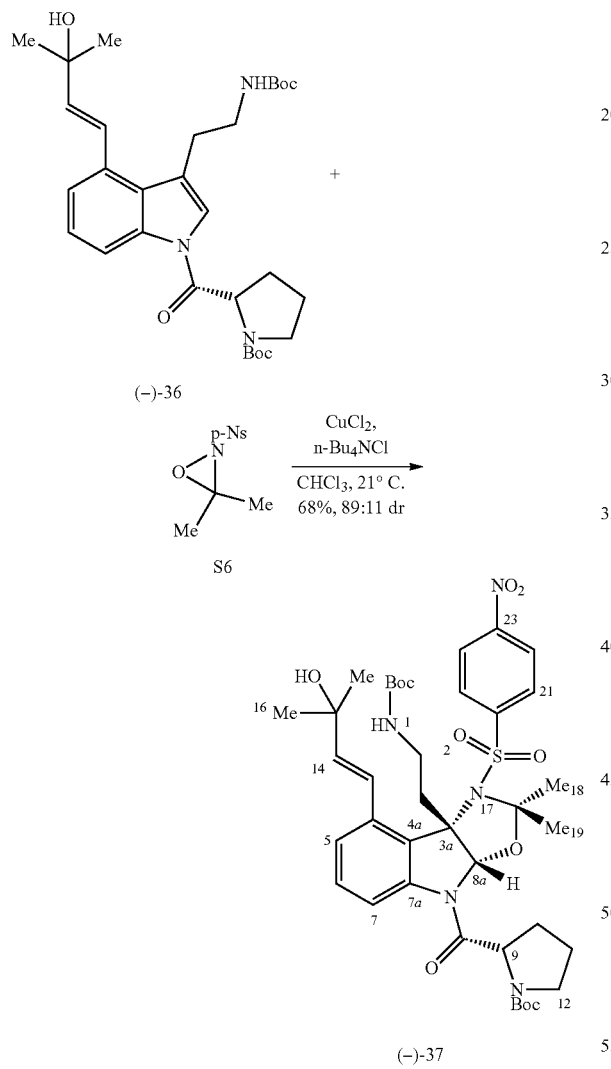

Oxazoline (−)-37:
Copper(II) chloride (1.03 g, 7.62 mmol, 1.00 equiv) and tetra-n-butylammonium chloride8 (4.13 g, 7.62 mmol, 1.00 equiv) were added to a 100 mL Schlenk flask. Chloroform (38 mL) was added and the resulting dark red mixture was stirred vigorously for 20 min, at which point allylic alcohol (−)-36 (4.13 g, 7.62 mmol, 1 equiv) and oxaziridine S69 (2.56 g, 9.91 mmol, 1.30 equiv) were added. After stirring at 21° C. for 1.5 h, the reaction mixture was filtered through a pad of silica gel, and the filter cake was washed with an ethyl Aminocyclotryptamine(+)-S7:
A solution of sodium methoxide (142 mg, 2.50 mmol, 50.0 equiv) in methanol (1.0 mL) was added to a solution of oxazoline (−)-37 (40.0 mg, 50.0 μmol, 1 equiv) in methanol (0.5 mL). After stirring at 21° C. for 24 h, the light yellow solution was diluted with a mixture of saturated aqueous ammonium chloride-water (1:1, 10 mL) and was extracted with dichloromethane (5×5 mL). The combined extracts were dried over anhydrous sodium sulfate, were filtered, and were concentrated under reduced pressure. The resulting yellow film was purified by flash column chromatography on silica gel (eluent: 10%→40% ethyl acetate in hexanes) to afford aminocyclotryptamine (+)-S7 (4.40 g, 83.8%, 89:11 er) as a yellow solid. The enantiomeric ratio was determined by chiral HPLC analysis (Chiralpak IA, 80% iPrOH/20% hexanes, 1.0 mL/min, 254 nm, $t_R$ (major)=7.8 min, $t_R$ (minor)=6.5 min).

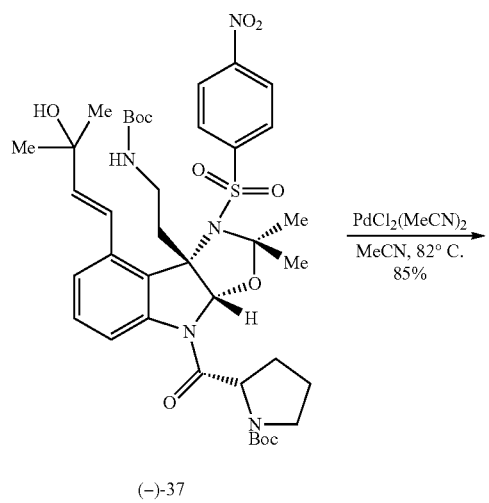

(−)-37

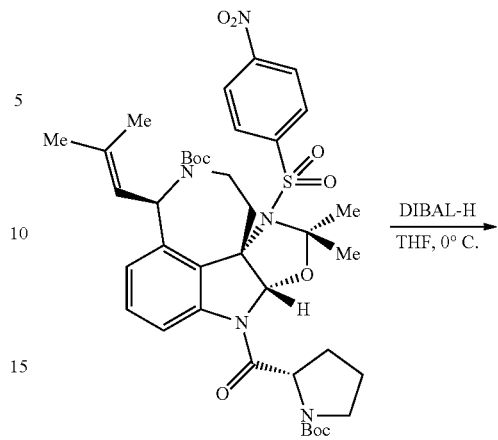

(−)-S8

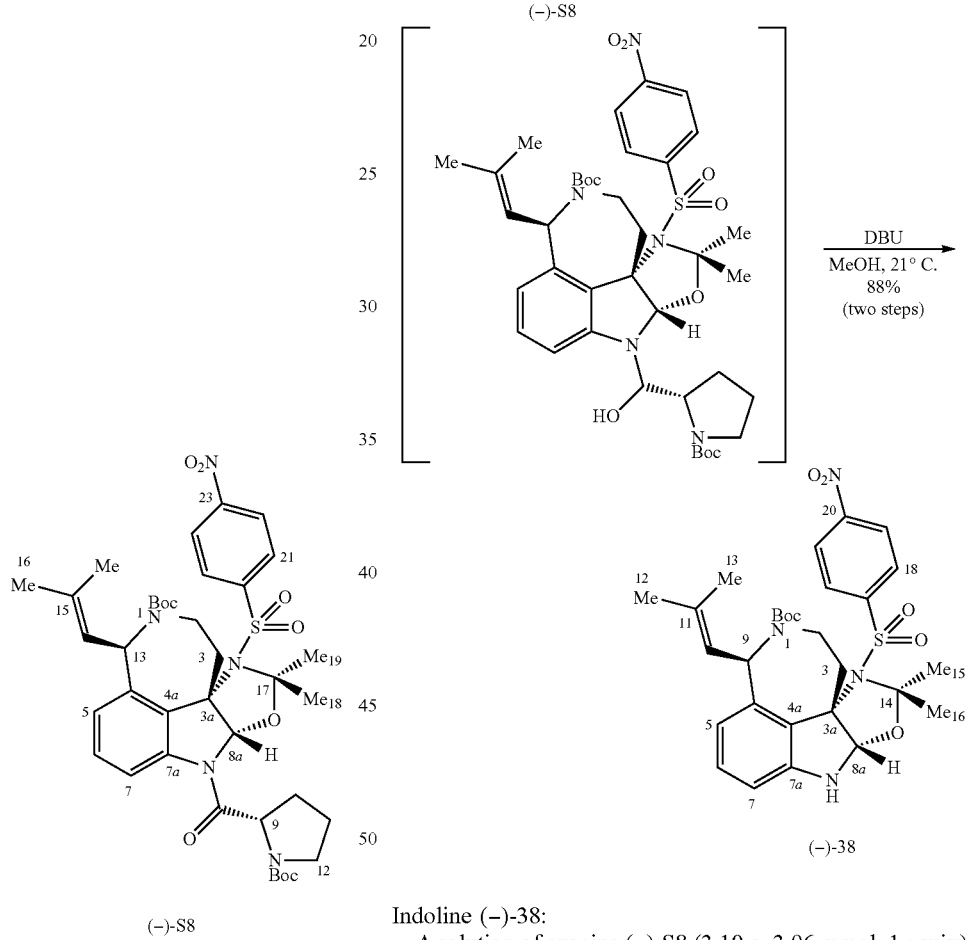

(−)-S8

Indoline (−)-38:

A solution of azepine (−)-S8 (3.10 g, 3.96 mmol, 1 equiv) in tetrahydrofuran (59 mL) was cooled to −20° C. and diisobutylaluminum hydride (1.0 M in hexanes, 11.9 mL, 11.0 mmol, 3.00 equiv) was added dropwise over 10 min. After 2 min, the reaction mixture was warmed to 0° C. and the orange solution was allowed to stir at this temperature. After 3 h, excess reducing agent was quenched cautiously by the dropwise addition of deionized water (11.9 mL). After gas evolution had subsided, an aqueous sodium hydroxide solution (1 N, 60 mL) was added. The resulting mixture was stirred vigorously for 15 min and was then extracted with ethyl acetate (3×120 mL). The combined organic extracts were dried over anhydrous sodium sulfate, were filtered through a pad of Celite, and were concentrated under Azepine (−)-S8:

Acetonitrile (70 mL) was added to a pressure tube containing bis(acetonitrile)-dichloropalladium(II) (190 mg, 720 µmol, 0.15 equiv) and oxazoline (−)-37 (89:11 dr, 3.85 g, 4.81 mmol, 1 equiv). The tube was sealed under an argon atmosphere and was immersed in a pre-heated oil bath at 82° C. After 4 h, the orange solution was cooled to 21° C. and the solvent was then removed under reduced pressure. The orange residue was purified by flash column chromatography on silica gel (eluent: 10%→20% acetone in hexanes) to afford azepine (−)-S8 (3.19 g, 84.8%) as a white powder.

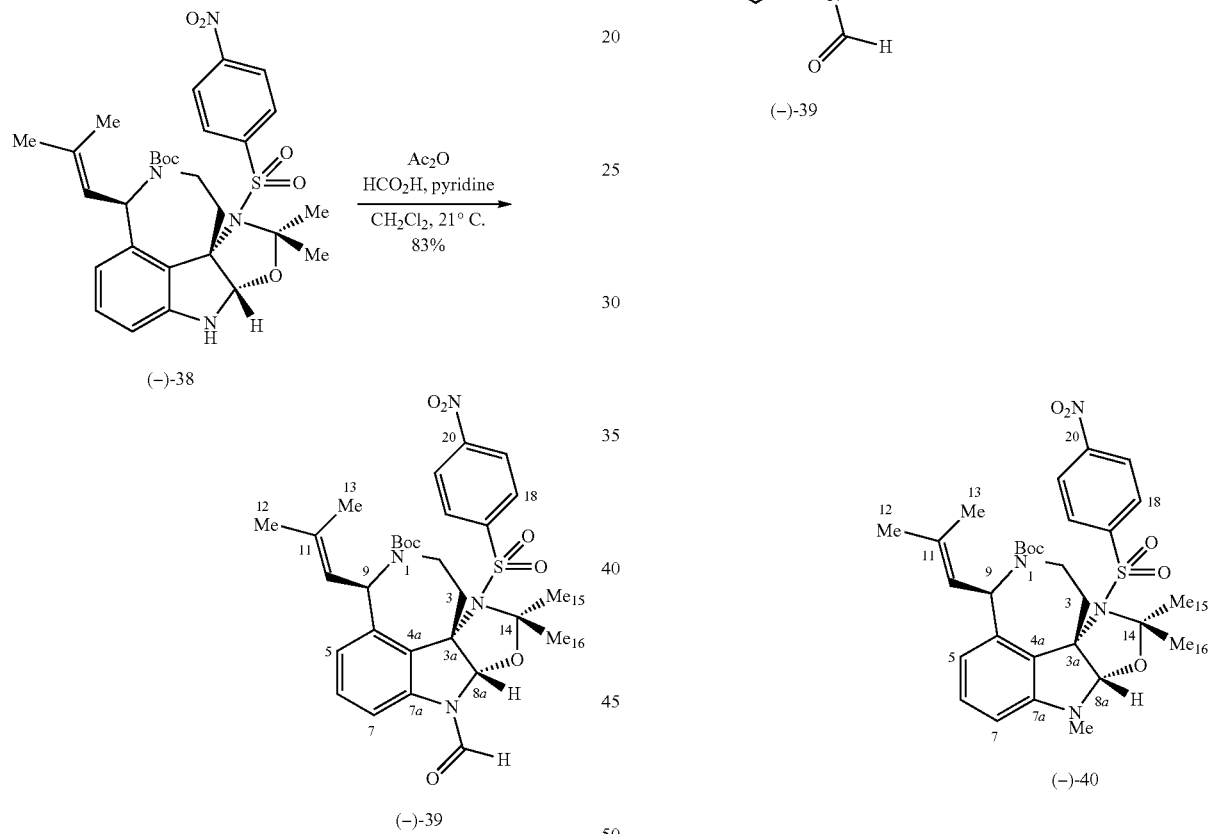

Formamide (−)-39:

A mixture of acetic anhydride (3.20 mL, 34.0 mmol, 10.0 equiv) and formic acid (1.30 mL, 34.0 mmol, 10.0 equiv) was added to a solution of indoline (−)-38 (1.98 g, 3.38 mmol, 1 equiv) and pyridine (274 L, 3.39 mmol, 1.00 equiv) in dichloromethane (13.5 mL) at 0° C.10 The reaction mixture was warmed to 21° C. and stirred vigorously. After 2 h, a saturated aqueous sodium bicarbonate solution (80 mL) was slowly introduced and the resulting mixture was stirred vigorously for 1 h, at which time gas evolution had ceased. The layers were separated and the aqueous layer was extracted with dichloromethane (3×40 mL). The combined organic extracts were dried over anhydrous sodium sulfate, were filtered, and were concentrated under reduced pressure to give a light yellow solid. Purification by flash column chromatography on silica gel (eluent: 10%→40% ethyl acetate in hexanes) afforded formamide (−)-39 as a light yellow solid. This solid was suspended in hexanes (60 mL) and was filtered to provide formamide (−)-39 (1.72 g, 83.1%) as a white solid.

N-Methyl Indoline (−)-40:

A sample of sodium borohydride (643 mg, 16.6 mmol, 6.00 equiv) was added to a solution of formamide (−)-39 (1.70 g, 2.77 mmol, 1 equiv) in tetrahydrofuran (55 mL). The resulting suspension was cooled to 0° C. and trifluoroacetic acid (1.27 g, 16.6 mmol, 6.00 equiv) was then added. After stirring at this temperature for 1.5 h, excess sodium borohydride was quenched by slow addition of a saturated aqueous sodium bicarbonate solution (55 mL). The resulting white suspension was diluted with deionized water (55 mL) and was extracted with ethyl acetate (3×120 mL). The combined organic extracts were dried over anhydrous sodium sulfate, were filtered, and were concentrated under reduced pressure. The residue was purified by flash column chromatography on silica gel (eluent: 20% ethyl acetate in hexanes) to afford N-methyl indoline (−)-40 (1.22 g, 73.5%) as a yellow solid.

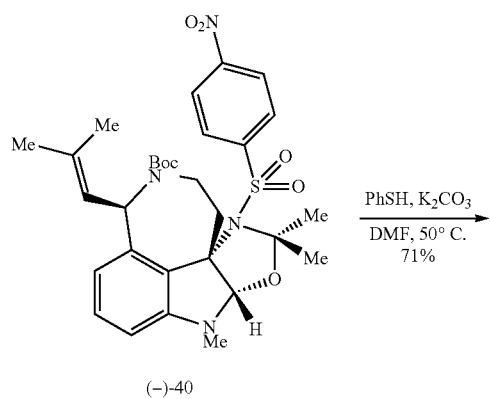

(−)-40

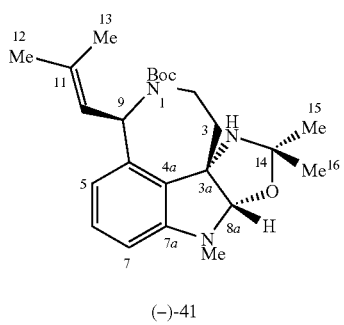

(−)-41

Hemiaminal (−)-41:

Thiophenol (1.0 mL, 10 mmol, 10 equiv) was added to a mixture of N-methyl indoline (−)-40 (0.620 g, 1.00 mmol, 1 equiv) and potassium carbonate (1.43 g, 10.4 mmol, 10.0 equiv) in dimethylformamide (10.4 mL) and the resulting brown suspension was heated to 50° C. After 2 h, the reaction mixture was cooled to 21° C., was diluted with deionized water (100 mL), and was extracted with diethyl ether (4×100 mL). The combined organic extracts were dried over anhydrous sodium sulfate, were filtered, and were concentrated under reduced pressure. The residue was purified by flash column chromatography on silica gel (eluent: 10%→20% ethyl acetate in hexanes). A second chromatographic purification on silica gel (eluent: 0%→10% ethyl acetate in dichloromethane) followed by azeotropic drying of the sticky foam with toluene furnished hemiaminal (−)-41 (304 mg, 70.9%) as a white solid.

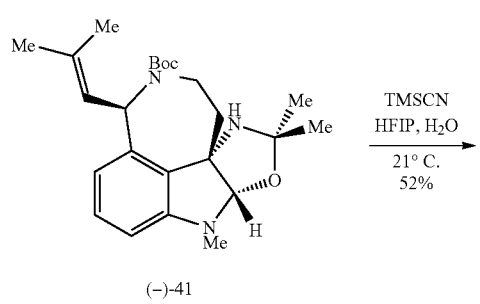

(−)-41

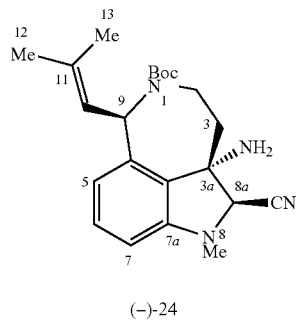

(−)-24

Tricyclic Amine (+)-24:

A Pressure Tube Containing Hemiaminal (−)-41 (62 mg, 0.15 Mmol, 1 Equiv) was Cooled to 0° C. and was charged sequentially with trimethylsilyl cyanide (58 µL, 0.45 mmol, 3.0 equiv), anhydrous hexafluoroisopropanol (58 µL, 0.54 mmol, 3.6 equiv), and water (8.1 µL, 0.45 mmol, 3.0 equiv). The mixture was warmed to 21° C. and the tube was quickly sealed under an argon atmosphere. After 10 days, an aqueous sodium hydroxide solution (1 N, 1.5 mL) was introduced and the resulting mixture was extracted with dichloromethane (3×2 mL). The combined organic extracts were dried over anhydrous sodium sulfate, were filtered, and were concentrated under reduced pressure. The residue was purified by flash column chromatography on silica gel (eluent: 10%→30% ethyl acetate in hexanes) to afford tricyclic amine (+)-24 (30.0 mg, 52.3%, $R_f$: 0.23; 50% ethyl acetate in hexanes) as a white foam and the C8a-epimer (15.0 mg, 26.1%, $R_f$: 0.85; 50% ethyl acetate in hexanes) as a white foam.

Example 3: Representative Synthesis of Formula (V) Compounds

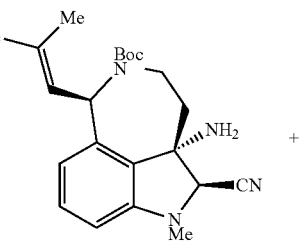

(+)-24

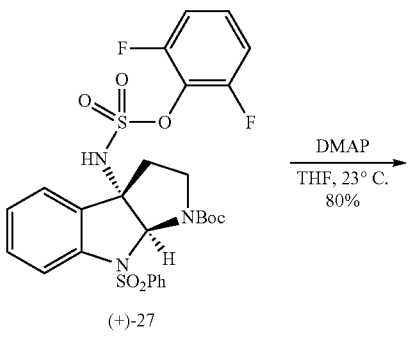

(+)-27

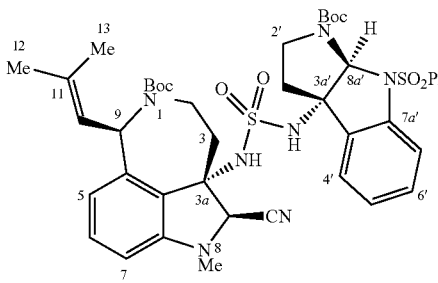

(+)-50

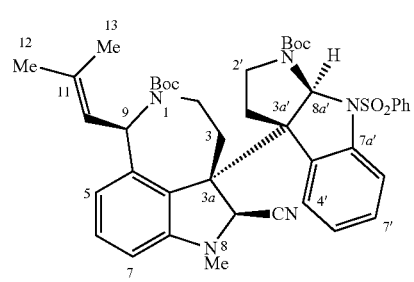

(+)-51

Sulfamide (+)-50:

A sample of 4-(dimethylamino)pyridine (518 mg, 4.24 mmol, 2.50 equiv) was added to a solution of tricyclic amine (+)-24 (662 mg, 1.70 mmol, 1 equiv) and sulfamate ester (+)-27 (1.21 g, 1.98 mmol, 1.17 equiv) in tetrahydrofuran (8.5 mL) at 23° C. After 20 h, deionized water (50 mL) was added and the mixture was extracted with dichloromethane (3×50 mL). The combined organic extracts were washed with a saturated aqueous sodium chloride solution (35 mL), were dried over anhydrous sodium sulfate, were filtered, and were concentrated under reduced pressure. The resulting residue was purified by flash column chromatography on silica gel (eluent: 20%→30% ethyl acetate in hexanes) to afford sulfamide (+)-50 (1.17 g, 80.0%) as an off-white foam.

Heterodimer (+)-51:

To a solution of sulfamide (+)-50 (300 mg, 349 μmol, 1 equiv) in methanol (34.9 mL) in the dark was added N-chloro-N-methylbenzamide16 (S11, 355 mg, 2.09 mmol, 6.00 equiv) followed immediately by resin-bound BEMP (1.90 g, ~2.2 mmol/g on 200-400 mesh polystyrene resin, 4.19 mmol, 12.0 equiv) in a single portion. After 18 min, the suspension was filtered through a pad of Celite, and the filter cake was washed sequentially with dichloromethane (60 mL) and ethyl acetate (60 mL). The light yellow filtrate was concentrated under reduced pressure and the resulting residue was purified by flash column chromatography on silica gel in low light (eluent: 15%→20% ethyl acetate in hexanes) to afford unsymmetrical diazene (+)-23 (157 mg, 56.6%) as a light yellow oil, which slowly solidified under reduced pressure.17 Unsymmetrical diazene (+)-23 was used directly in the next step without further purification. A solution of unsymmetrical diazene (+)-23 (155 mg, 195 μmol, 1 equiv) in dichloromethane (15 mL) was concentrated under reduced pressure in a 200 mL round bottom flask to provide a thin film of diazene (+)-23 coating the flask. The flask was evacuated and backfilled with argon (three cycles) and was then irradiated in a Rayonet photoreactor equipped with 16 radially distributed (r=12.7 cm) 25 W lamps (k=350 nm) at 25° C. After irradiating for 3 h, the lamps were shut off and the resulting residue was purified by flash column chromatography on silica gel (eluent: 20% ethyl acetate in hexanes) to afford an inseparable mixture (~1:1) of heterodimer (+)-51 and cyclotryptamine 28 according to $^1$H NMR analysis (91.4 mg, 38.7% corrected yield of 51) as an off-white foam. This mixture was used directly in the next step without further purification.

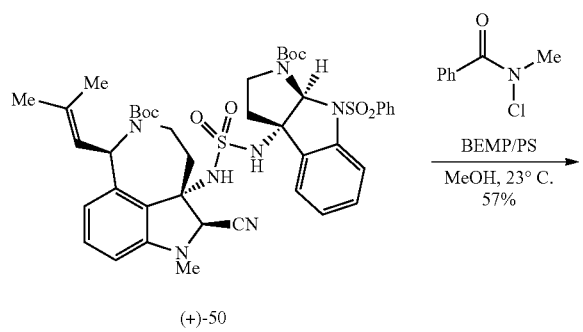

(+)-50

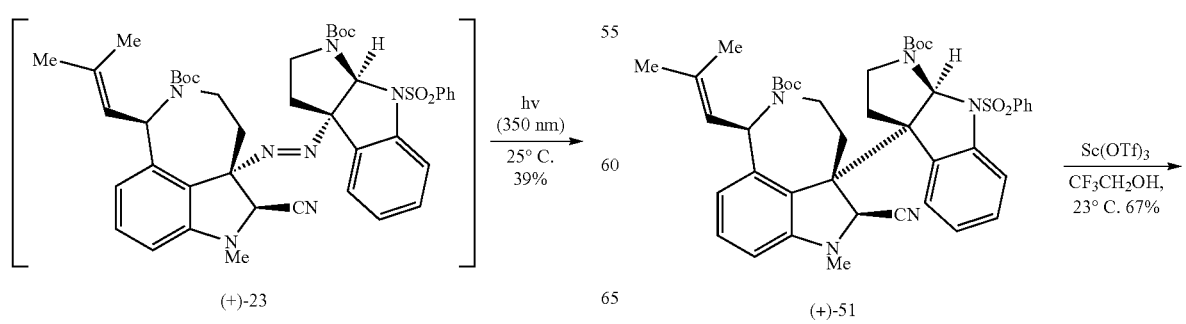

(+)-23

(+)-51

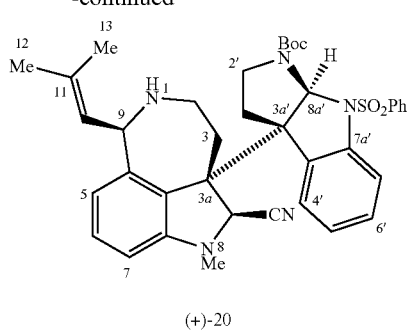

(+)-20

Heterodimeric Diamine (+)-20:

A sample of scandium(III) trifluoromethanesulfonate (223 mg, 452 μmol, 6.00 equiv) was added to an inseparable mixture of heterodimer (+)-51 (57.8 mg, 75.4 μmol, 1 equiv) and cyclotryptamine 28 (31.2 mg, 77.8 μmol, 1.03 equiv) dissolved in 2,2,2-trifluoroethanol (7.50 mL) at 23° C. After 25 min, a saturated aqueous sodium bicarbonate solution (15 mL) was added and the mixture was extracted with dichloromethane (3×15 mL). The combined organic extracts were washed with a saturated aqueous sodium chloride solution (15 mL), were dried over anhydrous sodium sulfate, were filtered, and were concentrated under reduced pressure. The resulting residue was purified by flash column chromatography on silica gel (eluent: 33% acetone, 1% methanol in dichloromethane) to afford heterodimeric diamine (+)-20 (28.4 mg, 66.6%) as a light tan foam.

Example 4. Representative Synthesis of Formula (I) Compounds

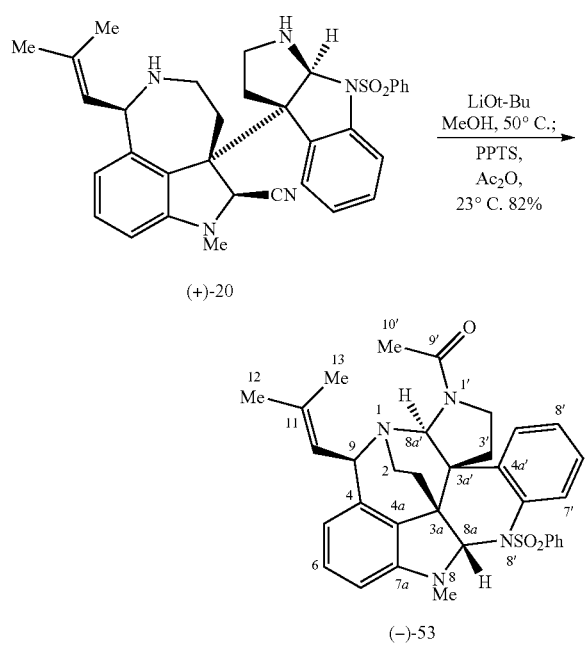

N8'-Benzenesulfonyl Communesin F (−)-53:

A solution of lithium tert-butoxide (0.100 M in MeOH, 1.13 mL, 113 μmol, 10.0 equiv) was added to a solution of heterodimer (+)-20 (6.30 mg, 11.1 μmol, 1 equiv) in methanol (1.13 mL). The vessel was sealed then immersed in a preheated 50° C. oil bath and was allowed to stir under a static atmosphere of argon. After 4 h, the reaction mixture was cooled to 23° C., after which pyridinium p-toluenesulfonate (22.4 mg, 89.1 μmol, 8.00 equiv) and acetic anhydride (9.5 μL, 100 μmol, 9.00 equiv) were added sequentially. After 24 min, a saturated aqueous sodium bicarbonate solution (3 was added and the resulting heterogeneous mixture was diluted with deionized water (5 mL) then extracted with dichloromethane (3×10 mL). The combined organic extracts were washed with a saturated aqueous sodium chloride solution (10 mL), were dried over anhydrous sodium sulfate, were filtered, and were concentrated under reduced pressure. The residue was purified via flash column chromatography (eluent: 25%→30% acetone in hexanes) to afford N8'-benzenesulfonyl communesin F (−)-53 (5.3 mg, 82%) as a white solid.

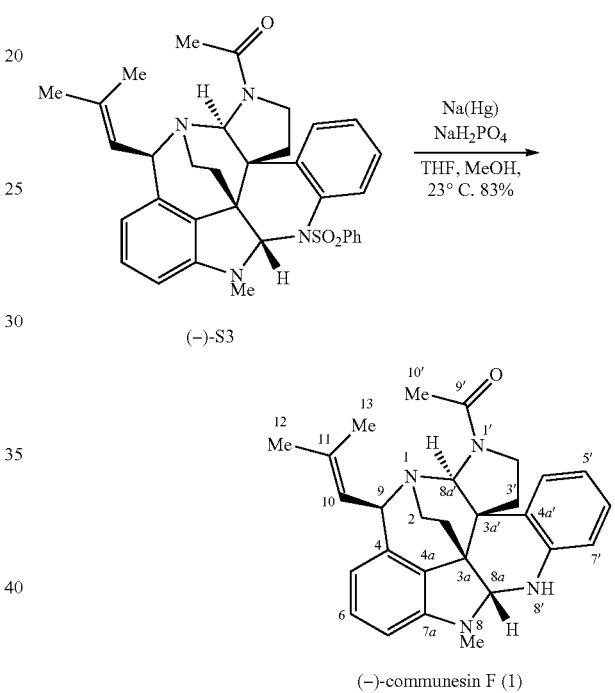

(−)-Communesin F (1):

A sample of sodium amalgam18 (5%-Na, 160 mg, 348 μmol, 20.0 equiv) was added to a suspension of sodium phosphate monobasic monohydrate (52.6 mg, 383 μmol, 22.0 equiv) and N8'-benzenesulfonyl communesin F (−)-53 (10.1 mg, 17.4 μmol, 1 equiv) in tetrahydrofuran (250 μL) and methanol (750 μL) at 23° C. After 20 min, another portion of sodium phosphate monobasic monohydrate (52.6 mg, 383 μmol, 22.0 equiv) and sodium amalgam (5%-Na, 160 mg, 348 μmol, 20.0 equiv) were added sequentially. After an additional 20 min, another portion of sodium phosphate monobasic monohydrate (52.6 mg, 383 μmol, 22.0 equiv) and sodium amalgam (5%-Na, 160 mg, 348 μmol, 20.0 equiv) were added sequentially. After an additional 20 min, a final portion of sodium phosphate monobasic monohydrate (52.6 mg, 383 μmol, 22.0 equiv) and sodium amalgam (5%-Na, 160 mg, 348 μmol, 20.0 equiv) were added sequentially. After 30 min, an aqueous solution of 5% sodium bicarbonate (5 mL) was added and the resulting mixture was extracted with dichloromethane (3×10 mL). The combined organic extracts were washed with a saturated aqueous sodium chloride solution (5 mL), were dried over anhydrous sodium sulfate, were filtered, and were concentrated under reduced pressure. The resulting residue was purified by flash column chromatography on silica gel (eluent: 25%→33% acetone in hexanes) to afford (−)-communesin F (1) (6.40 mg, 83.1%) as a white solid.

What is claimed is:

1. A compound of Formula (I):

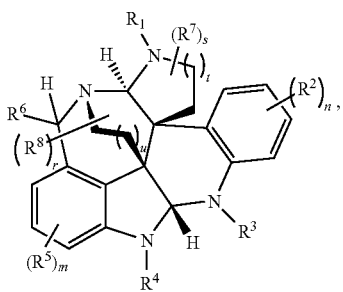

Formula (I)

or a pharmaceutically acceptable salt, tautomer, or stereoisomer thereof, wherein:

$R^1$ and $R^4$ are each independently selected from H, $C_1$-$C_{12}$ alkyl, $C_2$-$C_{12}$ alkenyl, $C_2$-$C_{12}$ alkynyl, —C(=O)$R^9$, —C(=O)N$R^9R^{10}$, —S(=O)$_u R^{12}$, aryl, heteroaryl, carbocyclyl, and heterocyclyl;

$R^3$ is selected from $C_1$-$C_{12}$ alkyl, $C_2$-$C_{12}$ alkenyl, $C_2$-$C_{12}$ alkynyl, —C(=O)$R^9$, —C(=O)N$R^9R^{10}$, —S(=O)$_u R^{12}$, aryl, heteroaryl, carbocyclyl, and heterocyclyl, or $R^3$ and $R^4$ taken together with the atoms to which they are attached form a heteroaryl or heterocyclic ring;

$R^2$ and $R^5$ are each independently selected from F, Cl, Br, I, —OH, —O$R^9$, —OC(=O)$R^9$, —S(=O)$_u R^{12}$, —N$R^9R^{10}$, $C_1$-$C_{12}$ alkyl, $C_2$-$C_{12}$ alkenyl, $C_2$-$C_{12}$ alkynyl, aryl, heteroaryl, carbocyclyl, and heterocyclyl;

$R^6$ is H, —OH, —O$R^9$, —OC(=O)$R^9$, —S(=O)$_u R^{12}$, —N$R^9R^{10}$, $C_1$-$C_{12}$ alkyl, $C_1$-$C_{12}$ alkyl, $C_2$-$C_{12}$ alkenyl, $C_2$-$C_{12}$ alkynyl, aryl, heteroaryl, carbocyclyl, or heterocyclyl;

$R^7$ and $R^8$ are each independently selected from $C_1$-$C_{12}$ alkyl, $C_2$-$C_{12}$ alkenyl, $C_2$-$C_{12}$ alkynyl, —C(=O)$R^9$, —C(=O)N$R^9R^{10}$, —S(=O)$_u R^{12}$, —OH, —O$R^9$, —OC(=O)$R^9$, —N$R^9R^{10}$, aryl, heteroaryl, carbocyclyl, and heterocyclyl, or two $R^7$ or two $R^8$ groups taken together with the carbon atoms to which they are attached form an aryl, heteroaryl, carbocyclic, or heterocyclic ring;

$R^9$ and $R^{10}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, and heterocyclyl, or $R^9$ and $R^{10}$ taken together with the atoms to which they are attached form a heteroaryl or heterocyclic ring;

each instance of $R^{12}$ is independently $C_1$-$C_{12}$ alkyl, $C_2$-$C_{12}$ alkenyl, $C_2$-$C_{12}$ alkynyl, aryl, heteroaryl, carbocyclyl, heterocyclyl, —(CH$_2$)$_n$SiMe$_3$, or —(CH$_2$)$_n R^9$;

m and t are each independently an integer from 0 to 3, inclusive;

n, r, and s are each independently an integer from 0 to 4, inclusive;

u' is 0, 1, or 2;

each instance of u is independently 0, 1, or 2; and each of the $C_1$-$C_{12}$ alkyl, $C_2$-$C_{12}$ alkenyl, $C_2$-$C_{12}$ alkynyl, aryl, heteroaryl, carbocyclyl, carbocyclic ring, heterocyclyl, and heterocyclic ring is independently optionally substituted.

2. The compound of claim 1, or a pharmaceutically acceptable salt, tautomer, or stereoisomer thereof, wherein $R^6$ is H, $C_1$-$C_{12}$ alkyl, $C_1$-$C_{12}$ alkenyl, aryl, heteroaryl, carbocyclyl, or heterocyclyl.

3. The compound of claim 1, or a pharmaceutically acceptable salt, tautomer, or stereoisomer thereof, wherein $R^4$ is H, —C(=O)$R^9$, $C_1$-$C_{12}$ alkyl, aryl, or heteroaryl.

4. The compound of claim 1, or a pharmaceutically acceptable salt, tautomer, or stereoisomer thereof, wherein $R^3$ is $C_1$-$C_{12}$ alkyl or —S(=O)$_u R^{12}$.

5. The compound of claim 1, or a pharmaceutically acceptable salt, tautomer, or stereoisomer thereof, wherein $R^2$ and $R^5$ are each independently F, Br, Cl, I, $C_1$-$C_{12}$ alkyl, aryl, or heteroaryl.

6. The compound of claim 1, or a pharmaceutically acceptable salt, tautomer, or stereoisomer thereof, wherein $R^6$ is

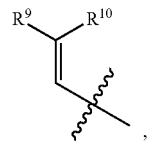

or

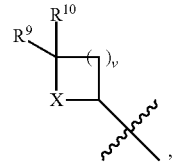

and wherein X is O, N$R^9$, or —S(=O)$_u R^{12}$, and v is an integer from 0 to 4, inclusive.

7. The compound of claim 6, or a pharmaceutically acceptable salt, tautomer, or stereoisomer thereof, wherein $R^1$ is —C(=O)$R^9$.

8. The compound of claim 7, or a pharmaceutically acceptable salt, tautomer, or stereoisomer thereof, wherein $R^9$ is Me, Et, n-Pr,

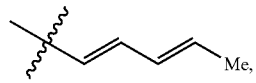 [SMILES: */C=C/C=C/C]

or

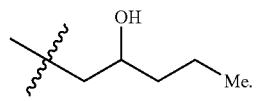 [SMILES: *CC(O)CCC]

9. The compound of claim 8, or a pharmaceutically acceptable salt, tautomer, or stereoisomer thereof, wherein $R^6$ is

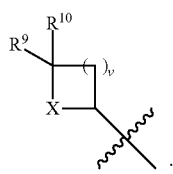

10. A pharmaceutical composition comprising a compound of claim 1, or a pharmaceutically acceptable salt, tautomer, or stereoisomer thereof, and a pharmaceutically acceptable excipient.

11. A method of making a compound of Formula (I):

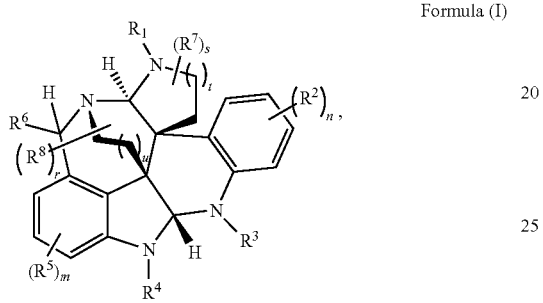

Formula (I)

or a pharmaceutically acceptable salt, tautomer, or stereoisomer thereof, wherein:

$R^1$, $R^3$, and $R^4$ are each independently selected from H, $C_1$-$C_{12}$ alkyl, $C_2$-$C_{12}$ alkenyl, $C_2$-$C_{12}$ alkynyl, —C(=O)$R^9$, —C(=O)$NR^9R^{10}$, —S(=O)$_u R^{12}$, aryl, heteroaryl, carbocyclyl, and heterocyclyl, or $R^3$ and $R^4$ taken together with the atoms to which they are attached form a heteroaryl or heterocyclic ring;

$R^2$ and $R^5$ are each independently selected from F, Cl, Br, I, —OH, —$OR^9$, —OC(=O)$R^9$, —S(=O)$_u R^{12}$, —$NR^9R^{10}$, $C_1$-$C_{12}$ alkyl, $C_2$-$C_{12}$ alkenyl, $C_2$-$C_{12}$ alkynyl, aryl, heteroaryl, carbocyclyl, and heterocyclyl;

$R^6$ is H, —OH, —$OR^9$, —OC(=O)$R^9$, —S(=O)$_u R^{12}$, —$NR^9R^{10}$, $C_1$-$C_{12}$ alkyl, $C_1$-$C_{12}$ alkyl, $C_2$-$C_{12}$ alkenyl, $C_2$-$C_{12}$ alkynyl, aryl, heteroaryl, carbocyclyl, or heterocyclyl;

$R^7$ and $R^8$ are each independently selected from $C_1$-$C_{12}$ alkyl, $C_2$-$C_{12}$ alkenyl, $C_2$-$C_{12}$ alkynyl, —C(=O)$R^9$, —C(=O)$NR^9R^{10}$, —S(=O)$_u R^{12}$, —OH, —$OR^9$, —OC(=O)$R^9$, —$NR^9R^{10}$, aryl, heteroaryl, carbocyclyl, and heterocyclyl, or two $R^7$ or two $R^8$ groups taken together with the carbon atoms to which they are attached form an aryl, heteroaryl, carbocyclic, or heterocyclic ring:

$R^9$ and $R^{10}$ are each independently selected from H, $C_1$-$C_{12}$ alkyl, $C_2$-$C_{12}$ alkenyl, $C_2$-$C_{12}$ alkynyl, aryl, heteroaryl, carbocyclyl, and heterocyclyl, or $R^9$ and $R^{10}$ taken together with the atoms to which they are attached form a heteroaryl or heterocyclic ring;

each instance of $R^{12}$ is independently $C_1$-$C_{12}$ alkyl, $C_2$-$C_{12}$ alkenyl, $C_2$-$C_{12}$ alkynyl, aryl, heteroaryl, carbocyclyl, heterocyclyl, —(CH$_2$)$_n$SiMe$_3$, or —(CH$_2$)$_n$$R^9$;

m and t are each independently an integer from 0 to 3, inclusive;

n, r, and s are each independently an integer from 0 to 4, inclusive;

u' is 0, 1, or 2;

each instance of u is independently 0, 1, or 2; and each of the $C_1$-$C_{12}$ alkyl, $C_2$-$C_{12}$ alkenyl, $C_2$-$C_{12}$ alkynyl, aryl, heteroaryl, carbocyclyl, carbocyclic ring, heterocyclyl, and heterocyclic ring is independently optionally substituted:

with the proviso that the compound is not of the formula:

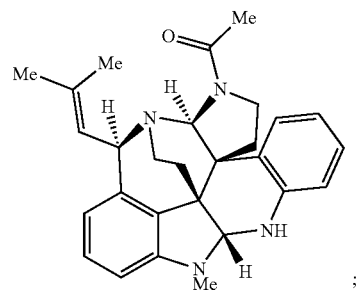

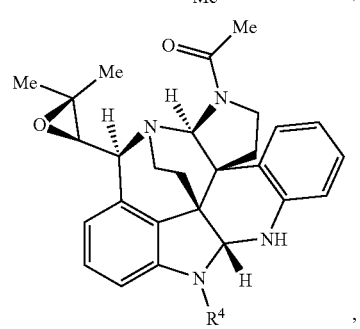

wherein $R^4$ is H or Me

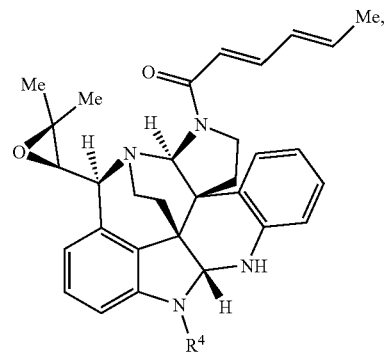

wherein $R^4$ is H, Me, or —CHO

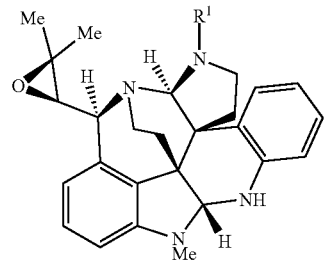

wherein $R^1$ is 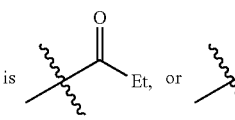 Et, or 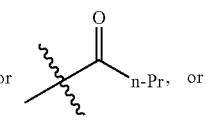 n-Pr, or

-continued

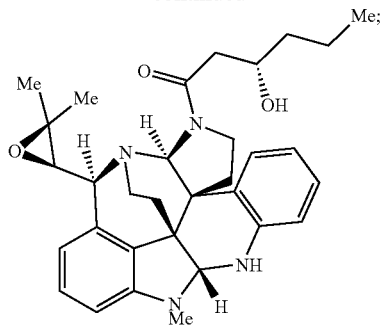

comprising forming a bond between the nitrogen atom at position N1 and the carbon atom at position C$_8$a', and a bond between the nitrogen atom at position N8' and the carbon atom at position C$_8$a in a compound of Formula (V):

Formula (V)

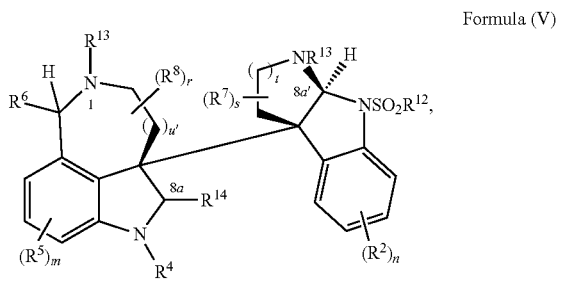

or a pharmaceutically acceptable salt, tautomer, or stereoisomer thereof, wherein R$^{13}$ is

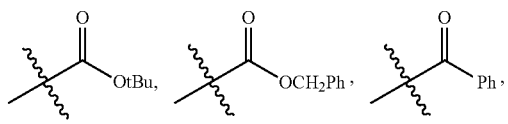

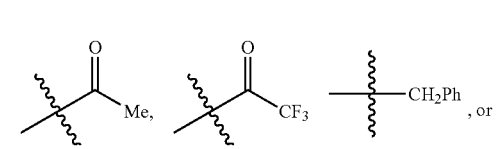

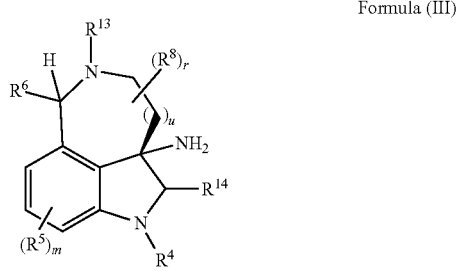

and R$^4$ is —CN, —OH, —OR$^9$, —NR$^9$R$^{10}$, —S(O)$_u$R$^{12}$, or —P(O)(OR$^9$)$_2$.

12. The method of claim 11 further comprising a radical recombination reaction of a compound of Formula (VI):

Formula (VI)

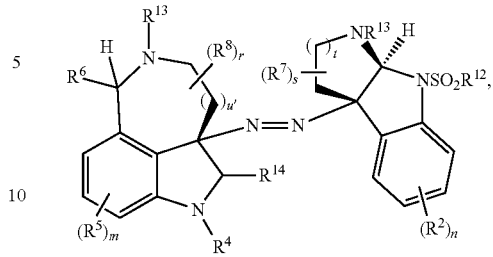

or a pharmaceutically acceptable salt, tautomer, or stereoisomer thereof, to form the compound of Formula (V), or a pharmaceutically acceptable salt, tautomer, or stereoisomer thereof.

13. The method of claim 12 further comprising the extrusion of sulfur dioxide from a compound of Formula (VII):

Formula (VII)

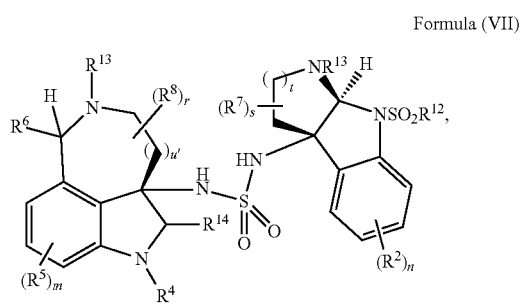

or a pharmaceutically acceptable salt, tautomer, or stereoisomer thereof, to form the compound of Formula (VI), or a pharmaceutically acceptable salt, tautomer, or stereoisomer thereof.

14. The method of claim 13 further comprising reacting a compound of Formula (III), or a pharmaceutically acceptable salt, tautomer, or stereoisomer thereof; and a compound of Formula (VIII), or a pharmaceutically acceptable salt, tautomer, or stereoisomer thereof:

Formula (III)

Formula (VIII)

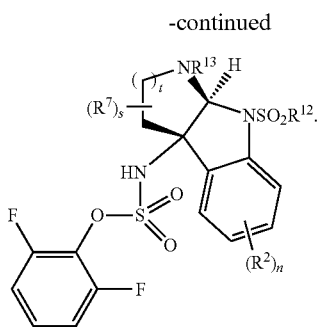

to form the compound of Formula (VII), or a pharmaceutically acceptable salt, tautomer, or stereoisomer thereof.

15. The compound of claim 1, or a pharmaceutically acceptable salt, tautomer, or stereoisomer thereof, wherein $R^6$ is heterocyclyl.

16. The compound of claim 6, or a pharmaceutically acceptable salt, tautomer, or stereoisomer thereof, wherein $R^6$ is

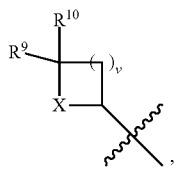

X is O, and v is 0.

17. The compound of claim 1, or a pharmaceutically acceptable salt, tautomer, or stereoisomer thereof, wherein $R^6$ is $C_2$-$C_{12}$ alkenyl.

18. The compound of claim 1, or a pharmaceutically acceptable salt, tautomer, or stereoisomer thereof, wherein $R^6$ is

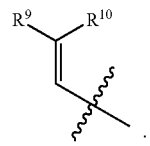

19. The compound of claim 1, or a pharmaceutically acceptable salt, tautomer, or stereoisomer thereof, wherein $R^3$ is $-S(=O)_u R^{12}$.

20. The compound of claim 19, or a pharmaceutically acceptable salt, tautomer, or stereoisomer thereof, wherein u is 2.

21. The compound of claim 20, or a pharmaceutically acceptable salt, tautomer, or stereoisomer thereof, wherein $R^{12}$ is $-(CH_2)_n SiMe_3$.

22. The compound of claim 1, or a pharmaceutically acceptable salt, tautomer, or stereoisomer thereof, wherein $R^4$ is $C_1$-$C_{12}$ alkyl.

23. The compound of claim 1, or a pharmaceutically acceptable salt, tautomer, or stereoisomer thereof, wherein t is 1.

24. The compound of claim 1, or a pharmaceutically acceptable salt, tautomer, or stereoisomer thereof, wherein u' is 1.

* * * * *

UNITED STATES PATENT AND TRADEMARK OFFICE
CERTIFICATE OF CORRECTION

PATENT NO. : 10,918,627 B2
APPLICATION NO. : 15/592090
DATED : February 16, 2021
INVENTOR(S) : Mohammad Movassaghi et al.

Page 1 of 3

It is certified that error appears in the above-identified patent and that said Letters Patent is hereby corrected as shown below:

In the Claims

In Claim 1, at Column 69, Lines 12-22, the formula: 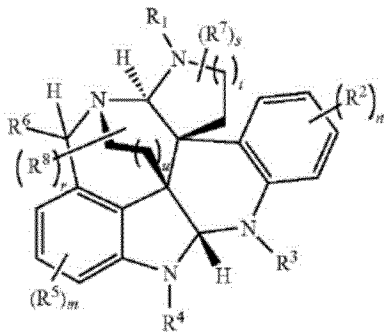 should be replaced with the formula: 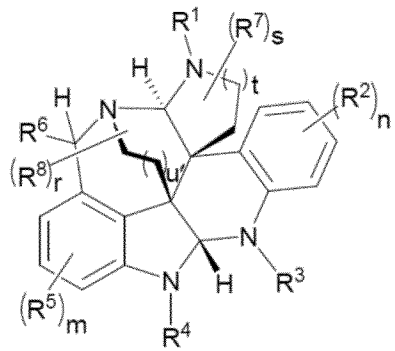 .

Signed and Sealed this
Twenty-second Day of June, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,918,627 B2

In Claim 11, at Column 71, Lines 17-28, the formula: 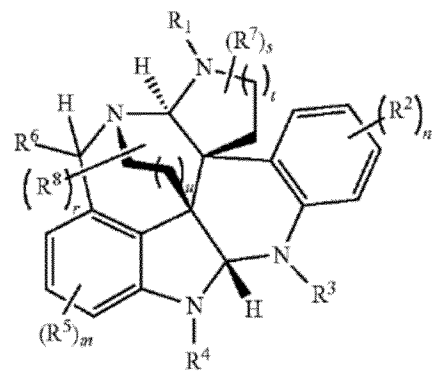 should be replaced with the formula: 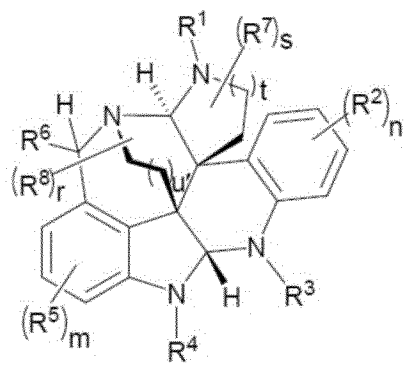 .

In Claim 11, at Column 71, Line 54, the text "ring:" should be replaced with the text --ring;--.

In Claim 11, at Column 73, Line 17, the text "$C_8a'''$" should be replaced with the text --C8a'--.

In Claim 11, at Column 73, Line 19, the text "$C_8a$" should be replaced with the text --C8a--.

In Claim 11, at Column 73, Lines 24-33, the formula: 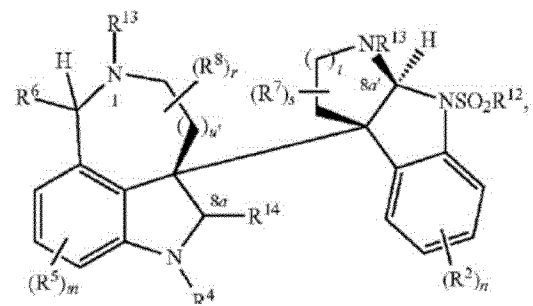

CERTIFICATE OF CORRECTION (continued)
U.S. Pat. No. 10,918,627 B2

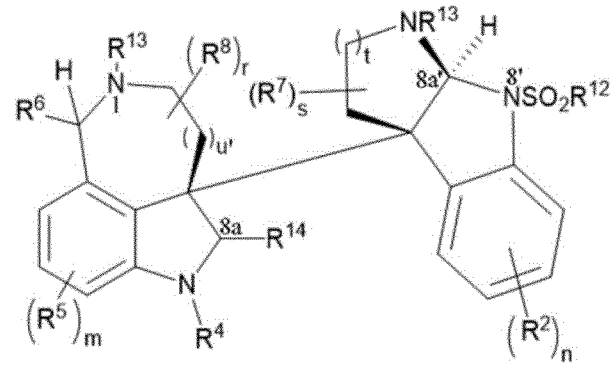

should be replaced with the formula:

In Claim 14, at Column 74, Lines 56-65, the formula: 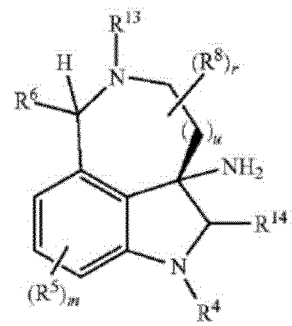 should be replaced with the formula: 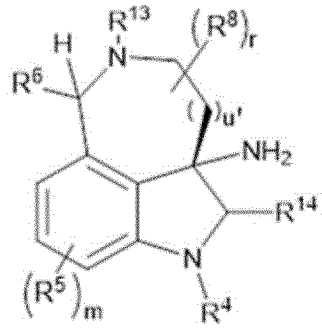 .